(12) United States Patent
Rikihisa et al.

(10) Patent No.: US 10,179,166 B2
(45) Date of Patent: Jan. 15, 2019

(54) EHRLICHIAL INVASIN FOR IMMUNIZATION, DIAGNOSIS, AND CELL DELIVERY

(71) Applicant: OHIO STATE INNOVATION FOUNDATION, Columbus, OH (US)

(72) Inventors: Yasuko Rikihisa, Worthington, OH (US); Dipu Mohan-Kumar, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/362,137

(22) Filed: Nov. 28, 2016

(65) Prior Publication Data
US 2017/0072041 A1    Mar. 16, 2017

Related U.S. Application Data

(62) Division of application No. 14/649,138, filed as application No. PCT/US2013/072850 on Dec. 3, 2013, now Pat. No. 9,526,772.

(60) Provisional application No. 61/810,039, filed on Apr. 9, 2013, provisional application No. 61/732,491, filed on Dec. 3, 2012.

(51) Int. Cl.
| | | |
|---|---|---|
| *A61K 39/00* | (2006.01) | |
| *A61K 39/02* | (2006.01) | |
| *C07K 14/29* | (2006.01) | |
| *A61K 39/385* | (2006.01) | |
| *G01N 33/68* | (2006.01) | |
| *G01N 33/569* | (2006.01) | |
| *A61K 47/64* | (2017.01) | |

(52) U.S. Cl.
CPC ........ *A61K 39/0233* (2013.01); *A61K 39/385* (2013.01); *A61K 47/646* (2017.08); *C07K 14/29* (2013.01); *G01N 33/56911* (2013.01); *G01N 33/6854* (2013.01); *C07K 2319/80* (2013.01); *G01N 2333/29* (2013.01); *G01N 2469/20* (2013.01); *G01N 2800/52* (2013.01)

(58) Field of Classification Search
CPC ................................................ A61K 39/0233
See application file for complete search history.

(56) References Cited

U.S. PATENT DOCUMENTS

| | | |
|---|---|---|
| 6,544,517 B1 | 4/2003 | Rikihisa et al. |
| 2011/0182925 A1 | 7/2011 | Krah, III et al. |

FOREIGN PATENT DOCUMENTS

| | | |
|---|---|---|
| WO | 2001058466 | 8/2001 |
| WO | 200180897 | 11/2001 |
| WO | 2008112007 | 9/2008 |
| WO | 2010126993 | 11/2010 |

OTHER PUBLICATIONS

Alonso, A., & Garcia-del Portillo, F. (2004). Hijacking of eukaryotic functions by intracellular bacterial pathogens. International Microbiology, 7(3), 181-191.
Bao, W., Kumagai, Y., Niu, H., Yamaguchi, M., Miura, K., & Rikihisa, Y. (2009). Four VirB6 paralogs and VirB9 are expressed and interact in Ehrlichia chaffeensis-containing vacuoles. Journal of bacteriology, 191(1), 278-286.
Barnewall, R. E., & Rikihisa, Y. (1994). Abrogation of gamma interferon-induced inhibition of Ehrlichia chaffeensis infection in human monocytes with iron-transferrin. Infection and immunity, 62(11), 4804-4810.
Barnewall, R. E., Rikihisa, Y., & Lee, E. H. (1997). Ehrlichia chaffeensis inclusions are early endosomes which selectively accumulate transferrin receptor. Infection and immunity, 65(4), 1455-1461.
Bierne, H., & Cossart, P. (2002). InIB, a surface protein of Listeria monocytogenes that behaves as an invasin and a growth factor. Journal of cell science, 115(17), 3357-3367.
Cardwell, M. M., & Martinez, J. J. (2009). The Sca2 autotransporter protein from Rickettsia conorii is sufficient to mediate adherence to and invasion of cultured mammalian cells. Infection and immunity, 77(12), 5272-5280.
Cheng, Z., Miura, K., Popov, V. L., Kumagai, Y., & Rikihisa, Y. (2011). Insights into the CtrA regulon in development of stress resistance in obligatory intracellular pathogen Ehrlichia chaffeensis. Molecular microbiology, 82(5), 1217-1234.
Crocquet-Valdes, P. A., Thirumalapura, N. R., Ismail, N., Yu, X., Saito, T. B., Stevenson, H. L., . . . & Walker, D. H. (2011). Immunization with Ehrlichia P28 outer membrane proteins confers protection in a mouse model of ehrlichiosis. Clinical and Vaccine Immunology, 18(12), 2018-2025.
Dawson, J. E., Anderson, B. E., Fishbein, D. B., Sanchez, J. L., Goldsmith, C. S., Wilson, K. H., & Duntley, C. W. (1991). Isolation and characterization of an *Ehrlichia* sp. from a patient diagnosed with human ehrlichiosis. Journal of Clinical Microbiology, 29(12), 2741-2745.
Frutos, Roger, et al. "Comparative genomic analysis of three strains of Ehrlichia ruminantium reveals an active process of genome size plasticity." Journal of bacteriology 188.7 (2006): 2533-2542.
Hotop

(56) References Cited

OTHER PUBLICATIONS

Huang, H., Lin, M., Wang, X., Kikuchi, T., Mottaz, H., Norbeck, A., & Rikihisa, Y. (2008). Proteomic analysis of and immune responses to Ehrlichia chaffeensis lipoproteins. Infection and immunity,76(8), 3405-3414.
International Search Report and Written Opinion of the U.S. International Searching Authority issued in PCT/US2013/072850 dated Mar. 10, 2014.
Kumagai, Y., Huang, H., & Rikihisa, Y. (2008). Expression and porin activity of P28 and OMP-1F during intracellular Ehrlichia chaffeensis development. Journal of bacteriology, 190(10), 3597-3605.
Kuriakose, J. A., Miyashiro, S., Luo, T., Zhu, B., & McBride, J. W. (2011). Ehrlichia chaffeensis transcriptome in mammalian and athropod hosts reveals differential gene expression and post transcriptional regulation. PLoS One, 6(6): e24136.
Kuriakose, J. A., Zhang, X., Luo, T., & McBride, J. W. (2012). Molecular basis of antibody mediated immunity against Ehrlichia chaffeensis involves species-specific linear epitopes in tandem repeat proteins. Microbes and Infection, 14(12), 1054-1063.
Levitzki, A., Willingham, M., & Pastan, I. (1980). Evidence for participation of transglutaminase in receptor-mediated endocytosis. Proceedings of the National Academy of Sciences, 77(5), 2706-2710.
Lin, M., Zhu, M. X., & Rikihisa, Y. (2002). Rapid activation of protein tyrosine kinase and phospholipase C-γ2 and increase in cytosolic free calcium are required by Ehrlichia chaffeensis for internalization and growth in THP-1 cells. Infection and immunity, 70(2), 889-898.
Lin, M., & Rikihisa, Y. (2003). Obligatory intracellular parasitism by Ehrlichia chaffeensis and Anaplasma phagocytophilum involves caveolae and glycosylphosphatidylinositol-anchored proteins. Cellular microbiology, 5(11), 809-820.
Lin M et al. (2011) Global proteomic analysis of two tick-borne emerging zoonotic agents: Anaplasma phagocytophilum and Ehrlichia chaffeensis. Frontiers in Microbiology 2(24), 1-19.
Liu, H., Bao, W., Lin, M., Niu, H., & Rikihisa, Y. (2012). Ehrlichia type IV secretion effector ECH0825 is translocated to mitochondria and curbs ROS and apoptosis by upregulating host MnSOD. Cellular microbiology, 14(7), 1037-1050.
Los, M., Neubüser, D., Coy, J. F., Mozoluk, M., Poustka, A., & Schulze-Osthoff, K. (2000). Functional characterization of DNase X, a novel endonuclease expressed in muscle cells. Biochemistry, 39(25), 7365-7373.
Martinez, J. J., Seveau, S., Veiga, E., Matsuyama, S., & Cossart, P. (2005). Ku70, a component of DNA-dependent protein kinase, is a mammalian receptor for Rickettsia conorii. Cell, 123(6), 1013-1023.
Miura, K., & Rikihisa, Y. (2007). Virulence potential of Ehrlichia chaffeensis strains of distinct genome sequences. Infection and immunity, 75(7), 3604-3613.
Miura, K., Matsuo, J., Rahman, M. A., Kumagai, Y., Li, X., & Rikihisa, Y. (2011). Ehrlichia chaffeensis induces monocyte inflammatory responses through MyD88, ERK, and NF-κB but not through TRIF, interleukin-1 receptor 1 (IL-1R1)/IL-18R1, or Toll-like receptors. Infection and immunity, 79(12), 4947-4956.
Mott J et al. (1999) Human granulocytic ehrlichiosis agent and Ehrlichia chajfeensis reside in different cytoplasmic compartments in HL-60 cells. Infect Immun 67: 1368-1378.
Niu, H., Rikihisa, Y., Yamaguchi, M., & Ohashi, N. (2006). Differential expression of VirB9 and VirB6 during the life cycle of Anaplasma phagocytophilum in human leucocytes is associated with differential binding and avoidance of lysosome pathway. Cellular microbiology, 8(3), 523-534.
Ohashi, N., Zhi, N., Zhang, Y., & Rikihisa, Y. (1998). Immunodominant Major Outer Membrane Proteins ofEhrlichia chaffeensis Are Encoded by a Polymorphic Multigene Family. Infection and immunity, 66(1), 132-139.
Paddock, C. D., & Childs, J. E. (2003). Ehrlichia chaffeensis: a prototypical emerging pathogen. Clinical microbiology reviews, 16(1), 37-64.
Philipp, Mario T., et al. "A decline in C6 antibody titer occurs in successfully treated patients with culture-confirmed early localized or early disseminated Lyme borreliosis." Clinical and diagnostic laboratory immunology 12.9 (2005): 1069-1074.
Popov, V. L., Yu, X. J., & Walker, D. H. (2000). The 120 kDa outer membrane protein of Ehrlichia chaffeensis: preferential expression on dense-core cells and gene expression in *Escherichia coli* associated with attachment and entry. Microbial pathogenesis, 28(2), 71-80.
Rashedi I (2008) The Role of DNase X in Skeletal Muscle Addressed by Targeted Disruption of the Gene in a Mouse Model. Master's of Science Thesis. Department of Biochemistry and Medical Genetics. Winnipeg: University of Manitoba. Winnipeg, Canada. 122 p.
Rikihisa, Y., & Ito, S. (1979). Intracellular localization of Rickettsia tsutsugamushi in polymorphonuclear leukocytes. The Journal of experimental medicine, 150(3), 703-708.
Rikihisa, Y., Ewing, S. A., & Fox, J. C. (1994). Western immunoblot analysis of Ehrlichia chaffeensis, E. canis, or E. ewingii infections in dogs and humans. Journal of clinical microbiology, 32(9), 2107-2112.
Rikihisa, Y. (2010). Anaplasma phagocytophilum and Ehrlichia chaffeensis: subversive manipulators of host cells. Nature Reviews Microbiology, 8(5), 328-339.
Riley, S. P., Goh, K. C., Hermanas, T. M., Cardwell, M. M., Chan, Y. G., & Martinez, J. J. (2010). The Rickettsia conorii autotransporter protein Sca1 promotes adherence to nonphagocytic mammalian cells. Infection and immunity, 78(5), 1895-1904.
Shiokawa, D., & Tanuma, S. I. (2001). Characterization of human DNase I family endonucleases and activation of DNase γ during apoptosis. Biochemistry, 40(1), 143-152.
Shiokawa, D., Matsushita, T., Shika, Y., Shimizu, M., Maeda, M., & Tanuma, S. I. (2007). DNase X is a glycosylphosphatidylinositol-anchored membrane enzyme that provides a barrier to endocytosis-mediated transfer of a foreign gene. Journal of Biological Chemistry, 282(23), 17132-17140.
Telford, S. R., & Dawson, J. E. (1996). Persistent infection of C3H/HeJ mice by Ehrlichia chaffeensis. Veterinary microbiology, 52(1), 103-112.
Thomas, S., Popov, V. L., & Walker, D. H. (2010). Exit mechanisms of the intracellular bacterium Ehrlichia. PLoS One, 5(12), e15775.
Unver, A., Rikihisa, Y., Ohashi, N., Cullman, L. C., Buller, R., & Storch, G. A. (1999). Western and dot blotting analyses of Ehrlichia chaffeensis indirect fluorescent-antibody assay-positive and-negative human sera by using native and recombinant E. chaffeensis and E. canis antigens. Journal of clinical microbiology, 37(12), 3888-3895.
Vlassov, V. V., Laktionov, P. P., & Rykova, E. Y. (2007). Extracellular nucleic acids. Bioessays, 29(7), 654-667.
Wang X et al. (2006) Two monoclonal antibodies with defined epitopes of P44 major surface proteins neutralize Anaplasma phagocytophilum by distinct mechanisms. Infect Immun 74: 1873-1882.
Winslow GM, Yager E, Shilo K, Volk E, Reilly A, et al. (2000) Antibody-mediated elimination of the obligate intracellular bacterial pathogen Ehrlichia chaffeensis during active infection. Infect Immun 68: 2187-2195.
Zhang JZ et al. (2007) The developmental cycle of Ehrlichia chaffeensis in vertebrate cells. Cell Microbial 9: 610-618.
Extended European Search Report, issued in European Application No. 13859849.5, dated Nov. 9, 2016.
Database EMBL [Online] Feb. 23, 2006 (Feb. 23, 2006), "Ehrlichia chaffeensis str. Arkansas hypothetical protein", XP002757837, retrieved from EBI accession No. EMBL:ABD45176.
Database EMBL [Online] Aug. 23, 2005 (Aug. 23, 2005), "Ehrlichia canis str. Jake hypothetical protein", XP002757838, retrieved from EBI accession No. EMBL:AAZ68869.
Database EMBL [Online] Jan. 4, 2005 (Jan. 4, 2005), "Ehrlichia ruminantium str. Welgevonden putative exported protein", XP002757839, retrieved from EBI accession No. EMBL:CAH58531.

(56) References Cited

OTHER PUBLICATIONS

Database UniProt [Online] Mar. 21, 2006 (Mar. 21, 2006), "SubName: Full=Uncharacterized protein {ECO:0000313|EMBL:ABD45176. 1};",retrieved from EBI accession No. UNIPROT:Q2GFG0 Database accession No. Q2GFG0.

Database UniProt [Online] Sep. 27, 2005 (Sep. 27, 2005), "SubName: Full=Uncharacterized protein {ECO:0000313|EMBL:AAZ68869. 1};",retrieved from EBI accession No. UNIPROT:Q3Y0Y6 Database accession No. Q3YQY6.

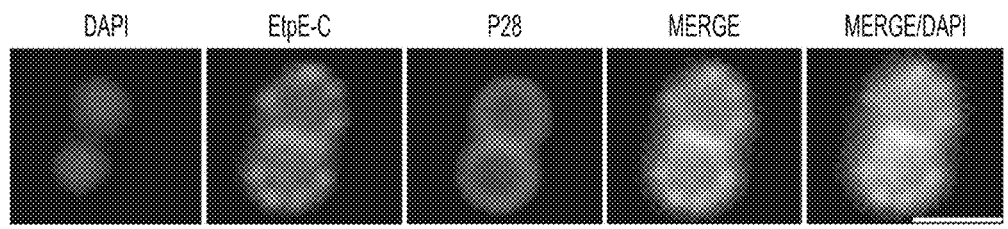
FIG. 1C
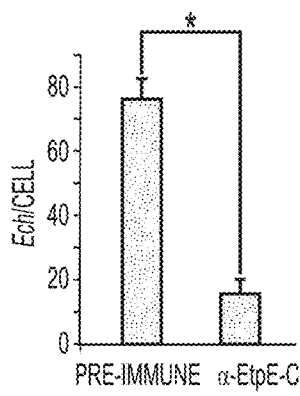 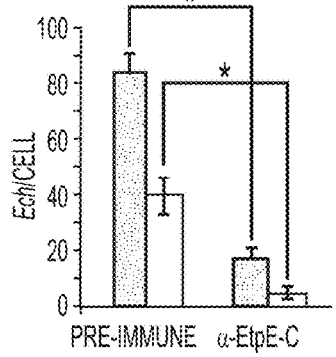 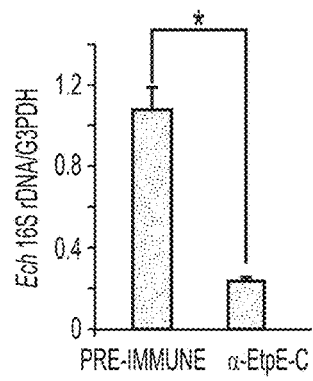
FIG. 1D   FIG. 1E   FIG. 1F
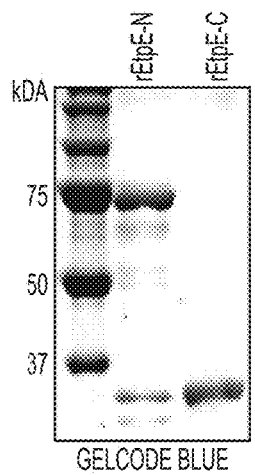
FIG. 2A

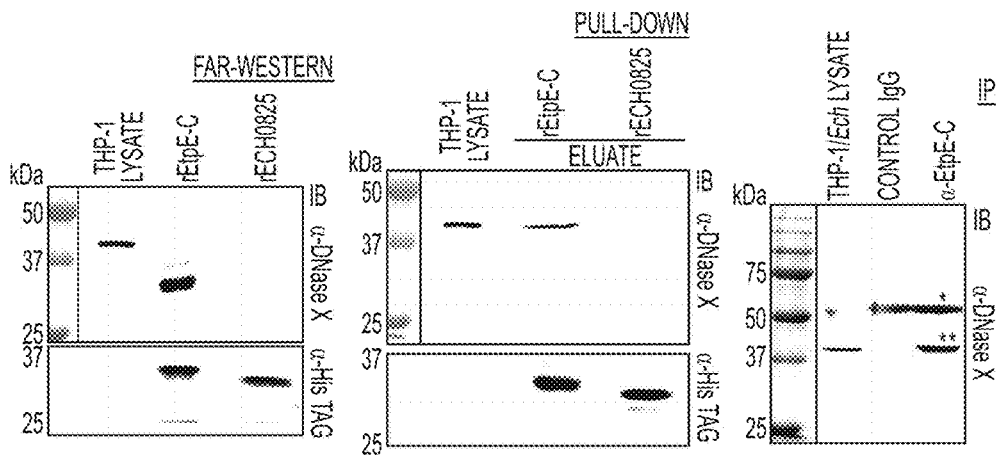
FIG. 5A  FIG. 5B  FIG. 5C
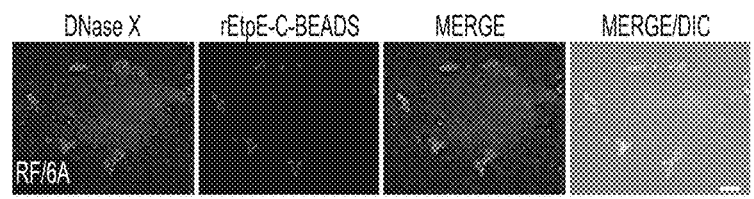
FIG. 5D
FIG. 5E
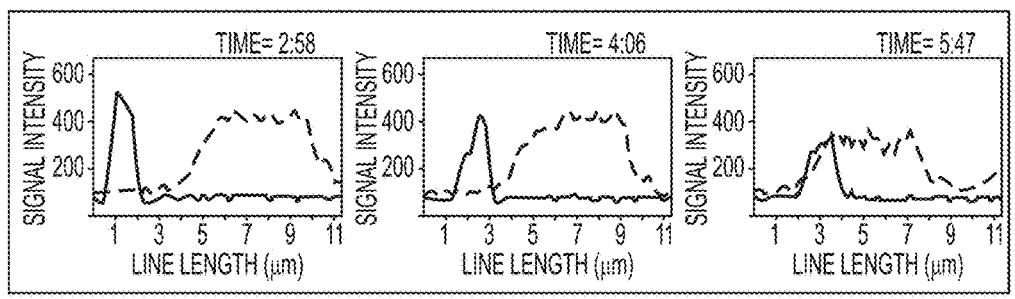
FIG. 5F

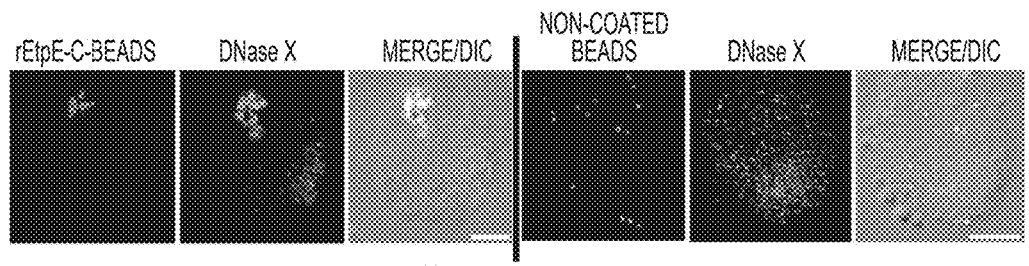
*FIG. 6A*
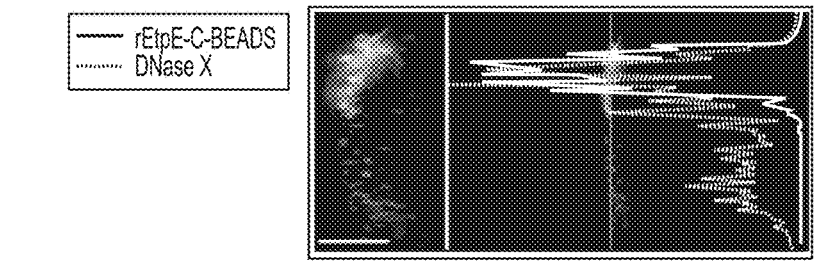
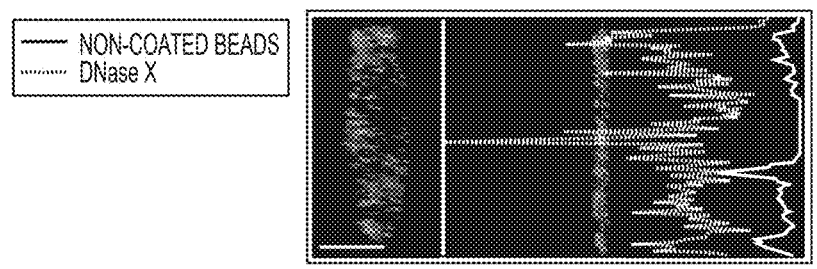
*FIG. 6B*
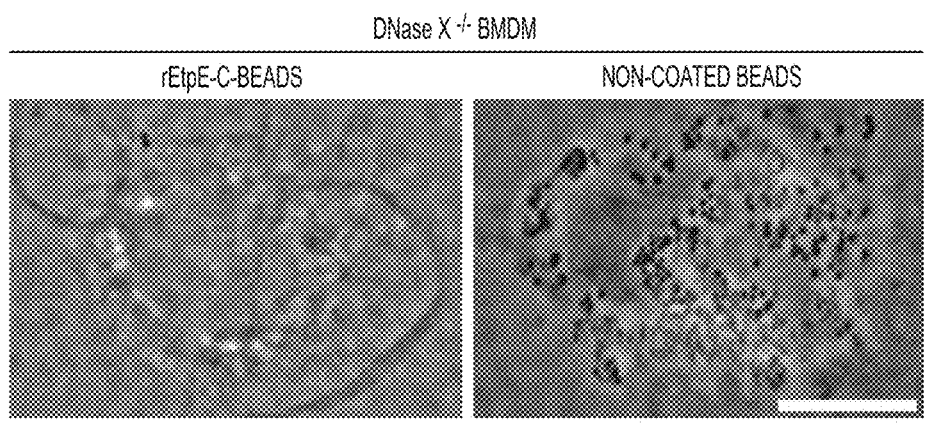
*FIG. 6C*

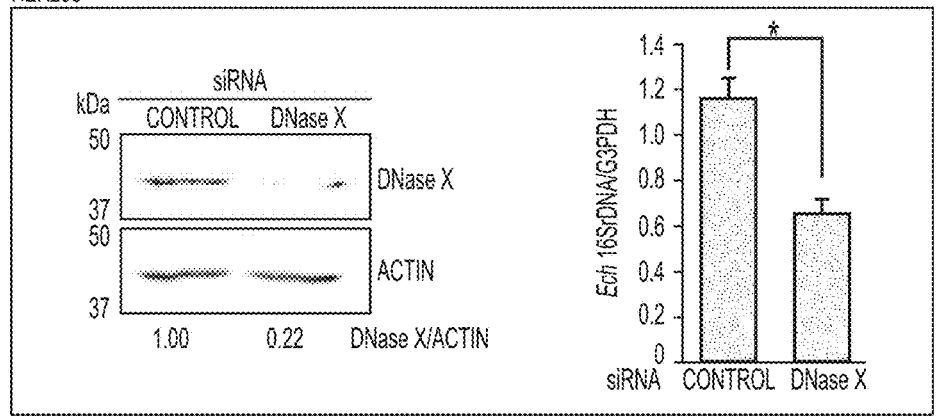
FIG. 7F      FIG. 7G
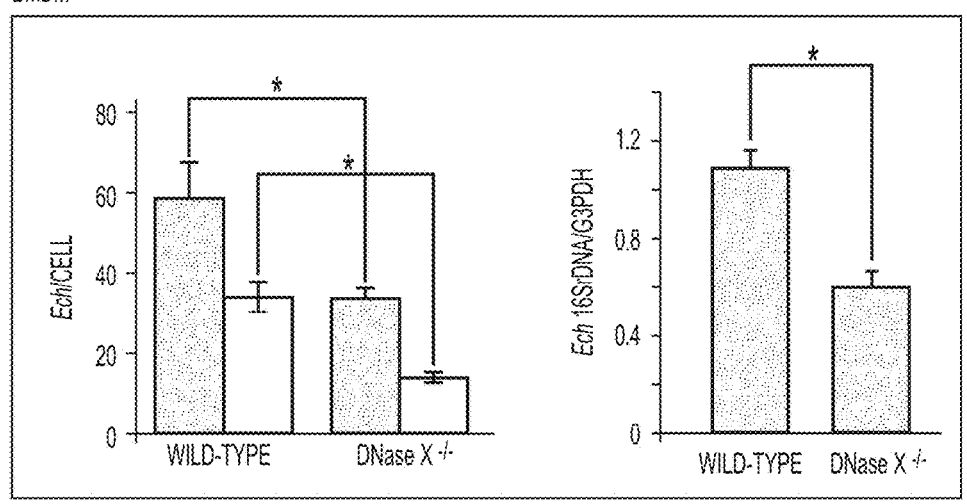
FIG. 7H      FIG. 7I

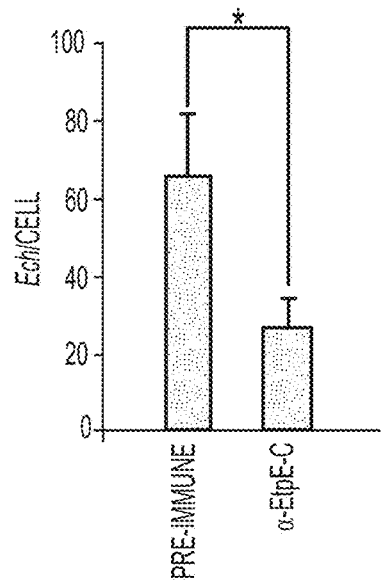
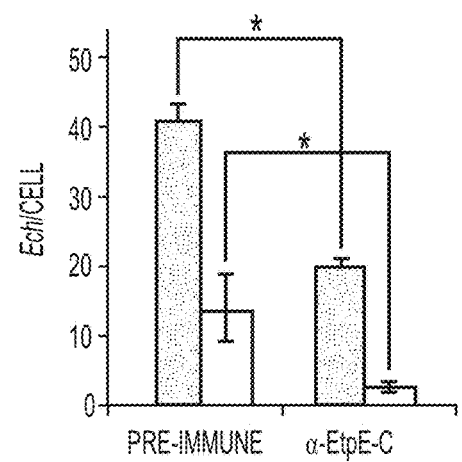
FIG. 10A  FIG. 10B
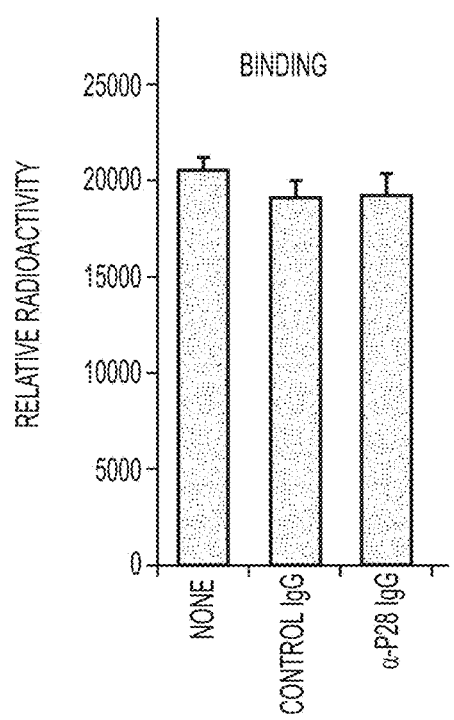
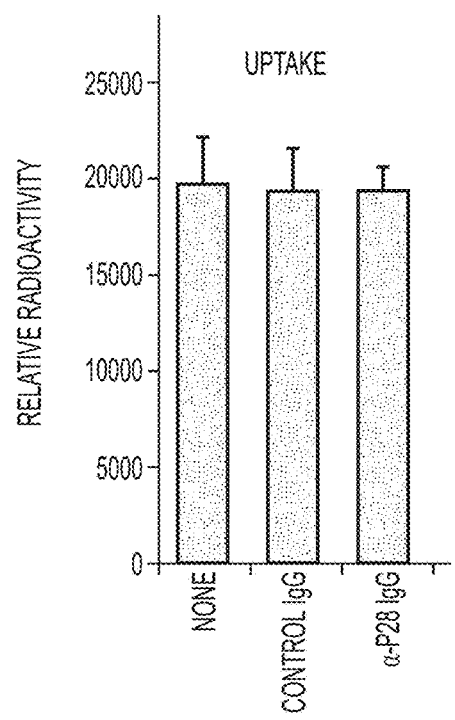
FIG. 11A  FIG. 11B

EHRLICHIAL INVASIN FOR IMMUNIZATION, DIAGNOSIS, AND CELL DELIVERY

CROSS-REFERENCE TO RELATED APPLICATIONS

This application is a divisional of copending application Ser. No. 14/649,138, filed Jun. 2, 2015, which is a 371 of international application number PCT/US2013/072850, filed Dec. 3, 2013, which claims benefit of U.S. Provisional Application No. 61/732,491, filed Dec. 3, 2012, and application Ser. No. 61/810,039, filed Apr. 9, 2013, each of which are hereby incorporated herein by reference in their entirety.

STATEMENT REGARDING FEDERALLY SPONSORED RESEARCH OR DEVELOPMENT

This invention was made with government support under R01 _AI30010 and R01 _AI047885 awarded by the National Institutes of Health. The government has certain rights in the invention.

BACKGROUND

*Ehrlichia chaffeensis* causes human monocytic ehrlichiosis (HME), an emerging tick-borne zoonosis. From the site of infected tick bite on human skin, *E. chaffeensis* infects monocytes and spreads via the bloodstream to various tissues, causing a systemic febrile disease. HME is characterized by fever, headache, myalgia, thrombocytopenia, leucopenia, and elevated liver-enzyme levels, but complications such as pulmonary insufficiency, renal failure, encephalopathy, and disseminated intravascular coagulation can cause death [Paddock C D, et al. (2003) Clin Microbiol Rev 16: 37-64]. Early diagnosis and the proper treatment with doxycycline are critical to prevent complications. The disease is of particular threat to the immunocompromised and the elderly people [Paddock C D, et al. (2003) Clin Microbiol Rev 16: 37-64].

*E. chaffeensis* is a small obligatory intracellular bacterium. It belongs to the family Anaplasmataceae in the order Rickettsiales that includes many understudied pathogens of veterinary and public health importance [Rikihisa Y (2010) Nat Rev Microbiol 8: 328-339]. By electron microscopy, *E. chaffeensis* is a polymorphic bacterium (0.2-2.0 µm in diameter), and can be morphologically categorized as small dense-cored cells (DCs) or large reticulate cells (RCs) [Popov V L, et al. (1995) J Med Microbiol 43: 411-421]. DCs are approximately 0.2-0.5 µm in diameter, which is close to the size of the elementary body of *Chlamydia* and larger viruses such as Vaccinia virus. By light microscopy, it is not possible to distinguish individual RCs and DCs, since *E. chaffeensis* aggregates inside eukaryotic host cells. The characteristic clump of intracellular *E. chaffeensis* organisms is termed as "morula" (mulberry in Latin) [Rikihisa Y (2010) Nat Rev Microbiol 8: 328-339]. However, when they are freshly isolated from host cells and dispersed, smaller bacteria (<0.5 µm) are more densely stained with basic dye than larger bacteria (>0.5 µm); therefore, they were defined as DCs and RCs, respectively [Zhang J Z, et al. (2007) Cell Microbiol 9: 610-618]. DCs are more resistant to strong sonication and more infectious than RCs [Cheng Z, et al. (2008) J Bacteriol 190: 2096-2105]. In cell culture, a biphasic developmental cycle has been reported: initially small infectious DCs bind to and internalize into host cells, which then develop into larger replicating RCs inside a membrane-lined compartment that resembles early endosomes. After replication in expanding inclusions, the mature RCs transform back into DCs prior to release from the host cells [Zhang J Z, et al. (2007) Cell Microbiol 9: 610-618; Cheng Z, et al. (2008) J Bacteriol 190: 2096-2105]. In patients' blood specimens, monocytes were primarily infected with *E. chaffeensis*, and hence, the disease was named as "monocytic ehrlichiosis" to distinguish it from "granulocytic ehrlichiosis" caused by infection with granulocyte-tropic *Ehrlichia* sp. [Paddock C D, et al. (2003) Clin Microbiol Rev 16: 37-64]. *E. chaffeensis* can replicate well in several mammalian cell lines including canine histiocytic leukemia (DH82), human acute leukemia (THP-1), human promyelocytic leukemia (HL-60), human embryonic kidney (HEK293), and monkey endothelial (RF/6A) cells [Mott J, et al. (1999) Infect Immun 67: 1368-1378; Liu H, et al. (2012) Cell Microbiol 14: 1037-1050; Miura K, et al. (2011) Infect Immun 79: 4947-4956].

Entry into the permissive eukaryotic host cells is essential for *E. chaffeensis* to sustain its life, since its small genome of 1.18 Mb lacks a large portion of metabolic genes that are required for free living [Dunning Hotopp J C, et al. (2006) PLoS Genet 2:e21]. *E. chaffeensis* also lacks LPS, peptidoglycan, lipoteichoic acid, and flagella that engage Toll-like or NOD-like receptors, or scavenger receptors [Rikihisa Y (2010) Nat Rev Microbiol 8: 328-339; Rikihisa Y (2010) Nat Rev Microbiol 8: 328-339]. *E. chaffeensis* entry and subsequent infection of THP-1 cells, but not binding are almost completely inhibited by monodansylcadaverine (MDC), a transglutaminase inhibitor [Lin M, et al. (2002) Infect Immun 70: 889-898]. MDC is known to block *Neorickettsia risticii* (formerly *Ehrlichia risticii*) entry and infection of P388D1 cells, vesicular stomatitis virus uptake and receptor-mediated endocytosis of α2-macroglobulin by Swiss 3T3 mouse cells, but not the uptake of latex beads by P388D1 mouse macrophages [Levitzki A, et al. (1980) Proc Natl Acad Sci USA 77: 2706-2710; Messick J B, et al. (1993) Infect Immun 61: 3803-3810; Schlegel R, et al. (1982) Proc Natl Acad Sci USA 79:2291-2295]. *E. chaffeensis* entry into THP-1 cells, leading to productive infection, is dependent on the host-cell surface lipid rafts and glycosylphosphatidyl inositol (GPI)-anchored proteins [Lin M, Rikihisa Y (2003) Cell Microbiol 5: 809-820]. Furthermore, lipid raft-associated protein caveolin-1, but not clathrin localizes to the *E. chaffeensis* entry site [Lin M, Rikihisa Y (2003) Cell Microbiol 5: 809-820]. After entry, *E. chaffeensis* replicates in the membrane-bound compartment resembling an early endosome as it contains early endosome antigen 1 (EEA1), Rab5, and transferrin receptor [Mott J, et al. (1999) Infect Immun 67: 1368-1378]. Several intracellular bacteria are known to enter host cells by using their specific surface protein collectively called as 'invasin' or 'internalin' [Pizarro-Cerda J, et al. (2006) Cell 124: 715-727]. However, detailed mechanisms of *E. chaffeensis* entry were unknown; particularly regarding the involvement of any specific bacterial surface protein that can function as an invasin and its cognitive host-cell receptor [Rikihisa Y (2010) Nat Rev Microbiol 8: 328-339].

The importance of *E. canis* as a veterinary pathogen in conjunction with the recent identification of *E. chaffeensis* as the cause of an emerging tick-borne zoonosis has highlighted the need for improved diagnostics and vaccines for both veterinary and human ehrlichioses, and thus the need for identification of immunoreactive proteins.

SUMMARY

The comparative genome hybridization study of *E. chaffeensis* strains identified a protein (referred to herein as "entry triggering protein of *Ehrlichia*" or "EtpE") with highly conserved N- and C-terminal segments flanking its strain-variable central region. As disclosed herein, EtpE, particularly its C-terminal conserved region ("EtpE-C"), is critical for *Ehrlichia* sp. binding, entry, and infection of several different host cell types. Immunization with rEtpE-C is also shown to protect mice against *Ehrlichia* sp. challenge. Further, antibodies to both the EtpE-C and the N-terminal region ("EtpE-N") can be found in subjects infected with *Ehrlichia* sp. Importantly, the EtpE-N is highly conserved across *Ehrlichia* sp. Therefore, disclosed herein are vaccines, diagnostics, and cell delivery polypeptides and uses therefore that take advantage of these unique properties of EtpE.

In particular, a vaccine is disclosed that comprises one or more polypeptides representing the EtpE from an *Ehrlichia* sp. and a pharmaceutically acceptable adjuvant. For example, the one or more polypeptide can comprise the amino acid sequence SEQ ID NO:1 (EtpE from *Ehrlichia chaffeensis* str. Arkansas; Accession No. YP_507823.1), SEQ ID NO:3 (EtpE from *Ehrlichia canis* str. Jake; Accession No. AAZ68869.1), or SEQ ID NO:5 (EtpE from *Ehrlichia ruminantium* str. Welgevonden; Accession No. YP_180660.1). Additional sequences for EtpE orthologues include *Ehrlichia* HF strain (*Ixodes ovatus Ehrlichia*) (Accession No. ABM69271.1), *Ehrlichia chaffeensis* Sapulpa strain (Accession No. ZP_00544864.1 and ZP_00544886.1), and *Ehrlichia ruminantium*, Gardel strain (Accession No. YP_196760.1). EtpE homologues/orthologues from other *Ehrlichia* sp. can also be identified and used to improve species cross-reactivity.

In some embodiments, the vaccine contains an immunogenic fragment of an EtpE protein that is capable of eliciting an immune response against an *Ehrlichia* sp. Preferably, the immunogenic fragment comprises at least a portion of the conserved region ("EtpE-C"). For example, the one or more polypeptide can comprise the amino acid sequence SEQ ID NO:2 (residues 1656-1963 of SEQ ID NO:1), SEQ ID NO:4 (residues 1408-1510 of SEQ ID NO:3), SEQ ID NO:6 (residues 1410-1710 of SEQ ID NO:5), or a an immunogenic fragment thereof capable of eliciting an immune response against an *Ehrlichia* sp.

The vaccine can alternatively contain an immunogenic variant of an EtpE protein, or fragment thereof, that is capable of eliciting an immune response against an *Ehrlichia* sp. For example, the vaccine can comprise one or more polypeptides having an amino acid sequence with at least 70% identity to an amino acid sequence selected from the group consisting of SEQ ID NO:1, SEQ ID NO:3, SEQ ID NO:5, or an immunogenic fragment thereof capable of eliciting an immune response against an *Ehrlichia* sp. The vaccine can comprise one or more polypeptides having an amino acid sequence with at least 7% identity to SEQ ID NO:2, SEQ ID NO:4, SEQ ID NO:6, or a an immunogenic fragment thereof capable of eliciting an immune response against an *Ehrlichia* sp.

The vaccine comprises polypeptides representing the EtpE from at least one *Ehrlichia* sp. However, to improve cross-reactivity, the vaccine can contain polypeptides representing the EtpE from at least 2, 3, 4, 5, 6, or more *Ehrlichia* sp. These polypeptides can be in a single amino acid sequence, such as fusion protein. The polypeptides can also be conjugated together on a single carrier molecule. For example, the polypeptides can be used in a multiple antigen peptide system (MAPS).

In some embodiments, the vaccine is capable of eliciting an immune response against any combination of *Ehrlichia chaffeensis, Ehrlichia canis*, and *Ehrlichia ruminantium*. The vaccine can also be capable of eliciting an immune response against other species, such as *Ehrlichia muris, Ehrlichia ewingil*, or a combination thereof. The EtpE homologue from these and other species and strains can be identified and used as immunogens as described herein.

Also disclosed is a recombinant vector that contains a nucleic acid sequence encoding any of the one or more immunogenic polypeptides disclosed herein, operatively linked to a heterologous promoter.

Also disclosed is a vaccine containing any of the disclosed recombinant vectors in a pharmaceutically acceptable vehicle, diluent or excipient. The vaccine can further contain a pharmaceutically acceptable adjuvant.

Also disclosed is a method for vaccinating a subject against *Ehrlichia* sp, that comprises administering to the subject a composition comprising any of the disclosed vaccines. The subject can be any mammal at risk for *Ehrlichia* sp. infection. In particular, the subject can be a human, canine, feline, bovine, ovine, or caprine subject. The method provides a protective immune response against at least one *Ehrlichia* sp. selected from the group consisting of *Ehrlichia chaffeensis, Ehrlichia canis*, and *Ehrlichia ruminantium*. However, in preferred embodiments, the vaccine elicits a protective immune response in the subject against at least 2, 3, 4, 5, 6, or more *Ehrlichia* sp.

Also disclosed is a method for diagnosing Ehrlichiosis in a subject that comprising assaying a biological sample (e.g., blood, serum, or plasma sample) from the subject for the presence of an antibody that specifically binds an EtpE polypeptide. In particular, assaying for antibodies that specifically bind an EtpE-N provides pan-diagnosis of *Ehrlichia* sp. infection since the N-terminal domain is highly conserved across species. Therefore, in some embodiments, the presence of the antibody is an indication that the subject has been infected with an *Ehrlichia* sp. selected from the group consisting of *Ehrlichia chaffeensis, Ehrlichia canis, Ehrlichia ruminantium*, or any combination thereof. Therefore, the method can involve assaying a biological sample from the subject for the presence of an antibody that specifically binds SEQ ID NO:7 (amino acid residues 29-708 of SEQ ID NO:1), SEQ ID NO:8 (amino acid residues 43-736 of SEQ ID NO:3), SEQ ID NO:9 (amino acid residues 39-730 of SEQ ID NO:5), or a conservative variant thereof having at least 70% identity to SEQ ID NO:7, SEQ ID NO:8, or SEQ ID NO:9, wherein the presence of the antibody is an indication that the subject has been infected with an *Ehrlichia* sp.

In some embodiments, the method provides a pan-diagnostic so that one test can be used for multiple species of *Ehrlichia*. However, in some embodiments, the method also diagnoses the specific *Ehrlichia* sp. In these embodiments, the EtpE-C polypeptide can be used to detect antibodies that selectively bind the C-terminal region of an EtpE from a specific species of *Ehrlichia*.

The disclosed methods can further comprise treating the subject for Ehrlichiosis if the antibody is detected. For example, the method can comprise treating the subject with an effective amount and duration of doxycycline if the antibody is detected. This should be done as early as possible, since at later stage of infection antibiotic became less effective in clearing bacteria or clinical signs. Therefore, early detection by the disclosed methods can improve treatment efficacy.

Also disclosed is a method for monitoring the treatment of a subject for Ehrlichiosis that comprises assaying a biological sample from the subject for levels of an antibody that specifically binds a polypeptide comprising SEQ ID NO:7, SEQ ID NO:8, or SEQ ID NO:9, or a conservative variant thereof having at least 70% identity to SEQ ID NO:7, SEQ ID NO:8, or SEQ ID NO:9. In these methods, an at least 2-, 3-, or 4-fold titer reduction in antibody levels is an indication that the treatment is effective. Of course, with chronic stage disease, this can take several months. Therefore, the method can involve assaying a sample from the subject every 1, 2, 3, 4, 5, or 6 weeks to monitor the treatment. Once antibody levels are no longer detectable, the method can further involve ceasing treatment. Alternatively, if antibody levels do not decrease as expected, then the method can further comprising altering the treatment, such as by increasing dosages or selecting an alternative antibiotic.

Also disclosed is a method for delivering a therapeutic or diagnostic agent to a cell in a subject that involves conjugating the agent, or a delivery vehicle comprising the agent, to a EtpE-C polypeptide. For example, the method can comprise administering to the subject a composition comprising the agent, wherein the agent, or a delivery vehicle comprising the agent, is conjugated to a delivery polypeptide comprising an amino acid sequence having at least 70% identity to SEQ ID NO:2, SEQ ID NO:4, SEQ ID NO:6, or a fragment thereof capable of binding DNase X, or to a nucleic acid encoding the polypeptide operably linked to a promoter. In these embodiments, the polypeptide can comprise at least 100, 101, 102, 103, 104, 105, 110, 120, 130, 140, 150, 160, 170, 180, 190, or 200 amino acids of SEQ ID NO:2, SEQ ID NO:4, or SEQ ID NO:6. In some embodiments, the polypeptide comprises at least residues 1658 to 1761 of SEQ ID NO:1, or a conservative variant thereof. In some embodiments, the polypeptide comprises at least residues 1408 to 1510 of SEQ ID NO:3, or a conservative variant thereof. In some embodiments, the polypeptide comprises at least residues 1410 to 1510 of SEQ ID NO:5, or a conservative variant thereof. The disclosed method can be used to deliver the agent to any cell expressing DNase X. In addition to leukocyte, endothelial cells, and kidney cells, DNase X is highly expressed in heart, brain, and placenta. Cells from these tissues can be targeted for EtpE-C-DNase X-mediated gene or drug delivery.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1F show that EtpE-C is exposed at the bacterial surface, and anti-EtpE-C neutralizes *E. chaffeensis* infection in vitro. FIG. 1A is a Western blot analysis of *E. chaffeensis*-infected (Ech) and uninfected DH82 cells at 60 h pi using anti-EtpE-N (a-EtpE-N) and anti-EtpE-C (a-EtpE-C). FIG. 1B shows double immunofluorescence labeling of *E. chaffeensis*-infected human primary macrophages derived from peripheral blood monocytes at 56 h pi. Cells were fixed with PFA, permeabilized with saponin, and labeled with anti-EtpE-C and anti-*E. chaffeensis* major outer membrane protein P28. The white dashed line denotes the macrophage contour. The boxed region indicates the area enlarged in the smaller panels to the right. Merge/DIC: Fluorescence images merged with Differential interference contrast image (DIC). A single z-plane (0.4 mm thickness) was shown. Scale bar, 2 mm. FIG. 1C shows *E. chaffeensis* incubated with DH82 cells for 30 min and double immunofluorescence labeled using anti-EtpE-C and anti-*E. chaffeensis* P28 without permeabilization. DAPI was used to label DNA. Scale bar, 1 mm. FIG. 1D is a bar graph showing numbers of *E. chaffeensis* bound to RF/6A cells at 30 min pi. Host cell-free *E. chaffeensis* was pretreated with anti-EtpE-C or preimmune mouse serum and incubated with RF/6A cells for 30 min. Unbound *E. chaffeensis* was washed away, cells were fixed with PFA, and *E. chaffeensis* labeled with anti-P28 without permeabilization. *E. chaffeensis* in 100 cells were scored. FIG. 1E is a bar graph showing numbers of *E. chaffeensis* internalized into RF/6A cells at 2 h pi. *E. chaffeensis* was pretreated with anti-rEtpE-C or preimmune mouse serum and incubated with RF/6A cells for 2 h. To distinguish intracellular from bound *E. chaffeensis*, unbound *E. chaffeensis* was washed away and cells were processed for two rounds of immunostaining with anti-P28; first without permeabilization to detect bound but not internalized *E. chaffeensis* (AF555-conjugated secondary antibody) and second round with saponin permeabilization to detect total *E. chaffeensis*, i.e., bound plus internalized (AF488-conjugated secondary antibody). *E. chaffeensis* in 100 cells was scored. The black bar represents total *E. chaffeensis* and the white bar represents internalized *E. chaffeensis* (total minus bound) (see also FIG. 9). FIG. 1F is a bar graph showing qPCR for *E. chaffeensis* 16S rDNA in RF/6A cells infected with *E. chaffeensis* at 48 h pi. *E. chaffeensis* was pretreated with anti-EtpE-C or preimmune mouse serum and used to infect RF/6A cells; cells were harvested at 48 h pi. qPCR for *E. chaffeensis* 16S rDNA was normalized with G3PDH DNA. Data represent the mean and standard deviation of triplicate samples and are representative of three independent experiments. *Significantly different ($P<0.05$).

FIGS. 2A-2C show EtpE is expressed by *E. chaffeensis* in HME patients and infected dogs, and immunization with rEtpE-C protects mice against *E. chaffeensis* challenge. FIG. 2A shows SDS-PAGE analysis and GelCode Blue staining of rEtpE-N (lane 1) and rEtpE-C (lane 2) (5 mg/lane). rEtpE-N was partially cleaved after its expression in *E. coli* and thus is visualized as multiple bands. FIG. 2B shows Western blot analysis of rEtpE-N (lane 1) and rEtpE-C (lane 2) (5 μg/lane) with HME patient sera (ID: 72088, MRL1-22, MRL1-40) or control human serum (Control), or sera from dogs experimentally infected with *E. chaffeensis* (ID: CTU-ALJ, 3918815, 1425) or control dog serum. The relative band intensity for rEtpE-N/rEtpE-C (75 kDa and 34 kDa bands) assessed by densitometry was shown beneath the panels. FIG. 2C shows dot-plot analysis of *E. chaffeensis* load of the blood samples from rEtpE-C-immunized and placebo-immunized mice at 5 days after *E. chaffeensis* challenge. qPCR of *E. chaffeensis* 16S rDNA normalized to mouse G3PDH DNA. *Significantly different ($P<0.05$).

FIG. 3A is an image showing latex beads coated with rEtpE-C by anti-EtpE-C labeling under fluorescence microscopy. Scale bar, 1 μm. FIG. 3B shows fluorescence and phase contrast merged images of rEtpE-C-coated beads incubated with mouse BMDMs. Cells were pretreated with DMSO (solvent control), MDC, genistein, or PI-PLC for 45 min followed by trypsin treatment to remove beads that were not internalized. Scale bar, 10 μm. FIGS. 3C and 3D are bar graphs showing numbers of internalized rEtpE-C-coated (C) and non-coated (D) beads/cell incubated with mouse BMDMs pretreated with MDC, genistein, or PI-PLC, relative to DMSO treatment (solvent control) set as 100. Data represent the mean and standard deviation of triplicate samples and are representative of three independent experiments. *Significantly different (P<0.05).

FIG. 4A shows rEtpE-C-coated beads (arrows), but not rEtpE-N, rECH0825, or rGroEL-coated beads, bind and enter HEK293 cells at 1 h pi. Scale bar, 10 μm. FIG. 4B is a bar graph showing quantitation of similar experiment as (A) by scoring beads in 100 cells. Data represent the mean and standard deviation of triplicate samples and are representative of three independent experiments. *Significantly different (P<0.05). FIG. 4C is a scanning electron micrograph of rEtpE-C-coated beads on the surface of RF/6A cells at 2 h pi. Note filopodia-like extensions embracing the beads (arrows). Scale bar, 1 μm. FIG. 4D is a transmission electron micrograph of rEtpE-C-coated beads being engulfed (left panel) and internalized (right panel) into RF/6A cells at 8 h pi. Note filopodia-like extensions embracing the beads (arrow). Scale bars, 0.5 μm (left) and 1 μm (right). FIG. 4E contains fluorescence and DIC images of rEtpE-C-coated beads in RF/6A cells. RF/6A cells were pretreated with DMSO (solvent), MDC, verapamil, or genistein for 30 min at 37° C., then incubated with rEtpE-C-coated beads for 8 h in the presence of compounds, washed and treated with trypsin to remove beads bound on the surface. A single z-plane (0.4 μm thickness) by deconvolution microscopy is shown here. Scale bar, 10 μm. FIG. 4F is a bar graph showing numbers of internalized rEtpE-C-coated beads/cell of similar experiments as (E), relative to the number in DMSO treatment set as 100. Data represent the mean and standard deviation of triplicate samples and are representative of three independent experiments. *Significantly different (P<0.05). FIG. 4G contains fluorescence and DIC merged images of RF/6A cells incubated with rEtpE-C-coated beads immunostained at 1 h pi with anti-EEA1 after permeabilization. Arrows indicate beads surrounded with EEA1. The boxed region is enlarged to the right. A single z-plane (0.2 μm thickness) by deconvolution microscopy is shown here. Scale bar, 5 μm.

FIGS. 5A-5F show EtpE-C binds DNase X. FIG. 5A shows far-Western blotting of renatured rEtpE-C and rECH0825 on a nitrocellulose membrane incubated with THP-1 cell lysate. Native DNase X was detected with anti-DNase X (α-DNase X), and recombinant proteins were detected with anti-histidine-tag (α-His tag). FIG. 5B shows Western blotting of THP-1 cell lysate following affinity pull-down with rEtpE-C bound to Ni-silica matrix. Bound proteins were eluted with imidazole and labeled with α-DNase X or α-His tag. FIG. 5C shows Western blot analysis of E. chaffeensis-infected THP-1 cell lysate immunoprecipitated with anti-EtpE-C (α-EtpE-C) or control IgG. THP-1 cells were incubated with E. chaffeensis for 30 min, followed by lysis, and immunoprecipitated with α-EtpE-C or control mouse IgG-bound protein A agarose. The precipitates were subjected to Western blotting with α-DNase X. ** DNase X, * mouse IgG heavy chain. FIG. 5D shows immunofluorescence labeling of rEtpE-C-coated latex beads incubated with RF/6A cells for 1 h with α-DNase X without permeabilization. Note a cluster of beads colocalizes with host cell-surface DNase X. Scale bar, 5 μm. FIG. 5E shows selected time-lapse images (0 to 6:38 min) of rEtpE-C-coated beads attached to RF/6A cells expressing DNase X-GFP at 4° C., and time 0 min was set upon raising the temperature to 37° C. The white dashed line denotes the RF/6A cell contour. A single z-plane (0.4 μm thickness) by deconvolution microscopy was shown. Scale bar, 2 μm. FIG. 5F shows line intensity profile analysis of rEtpE-C-beads and DNase X-GFP signal along the length of the line (slanted white line in the image 5E).

FIGS. 6A-6D show internalization of rEtpE-C-coated beads is dependent on DNase X. FIG. 6A shows immunofluorescence labeling of rEtpE-C-coated or noncoated beads incubated with human macrophages derived from peripheral blood monocytes. At 30 min pi, cells were labeled with α-DNase X without permeabilization. rEtpE-C-coated beads cluster and colocalize with DNase X on the cell surface, but non-coated beads do not. A single z-plane (0.4 μm thickness) by deconvolution microscopy was shown. Scale bar, 5 μm (see also FIG. 13). FIG. 6B is a selected image showing the orthogonal view of macrophage incubated with rEtpE-C-coated (left panel) or non-coated (right panel) beads in (A). The orthogonal view was obtained from the reconstituted 3-D view of serial z-stack images (combined z-section width of 7.2 μm). Scale bar, 5 μm. The fluorescence intensity profiles of DNase X and beads signals were shown. FIG. 6C shows fluorescence and phase contrast merged images of rEtpEC-coated and non-coated beads incubated with BMDMs from DNase X$^{-/-}$ and wild-type mice. Cells and beads were incubated for 45 min followed by trypsin treatment to remove non-internalized beads. Scale bar, 10 μm. FIG. 6D shows numbers of internalized rEtpE-C-coated beads/cell of similar experiment as (C), relative to the number of non-coated beads set as 100. Data represent the mean and standard deviation of triplicate samples and are representative of three independent experiments. *Significantly different (P<0.05) (see also FIG. 14).

FIGS. 7A-7J show that DNase X mediates E. chaffeensis binding, entry, and infection. FIG. 7A shows double immunofluorescence labeling with α-P28 and α-DNase X, without permeabilization, of E. chaffeensis bound on DH82 cells at 45 min pi at MOT of 10:1. The white dashed line denotes the DH82 cell contour. The arrow indicates the area enlarged in the smaller panels to the right. DNase X at the host-cell surface clusters to bound E. chaffeensis (arrows). Scale bar, 5 μm. FIG. 7B is a confocal image of double immunofluorescence labeled E. chaffeensis on human macrophages derived from peripheral blood monocytes at 30 min pi at MOT of 10:1, with α-P28 and α-DNase X without permeabilization. DNase X colocalizes with the sites of E. chaffeensis binding (arrow, the region enlarged in the smaller panels to the right). Scale bar, 5 μm. FIG. 7C shows numbers of E. chaffeensis bound to DH82 cells pretreated with α-DNase X or mouse IgG at 30 min pi. Immunofluorescence labeling with α-P28 was performed without permeabilization and the numbers of E. chaffeensis on 100 cells were scored. Data represent the mean and standard deviation of triplicate samples and are representative of three independent experiments. *Significantly different (P<0.05). FIG. 7D shows numbers of E. chaffeensis internalized into DH82 cells pretreated with α-DNase X or mouse IgG at 2 h pi. Cells were processed for two rounds of immunostaining with α-P28 as described in FIG. 1E. The black bar represents total E. chaffeensis, and the white bar represents internalized E. chaffeensis (total minus bound). E. chaffeensis in 100 cells were scored. Data represent the mean and standard deviation of triplicate samples and are representative of three independent experiments. *Significantly different (P<0.05). FIG. 7E shows E. chaffeensis load in DH82 cells pretreated with α-DNase X or mouse IgG at 48 h pi. qPCR for E. chaffeensis 16S rDNA normalized with canine G3PDH DNA. Data represent the mean and standard deviation of triplicate samples and are representative of three independent experiments. *Significantly different (P<0.05). FIG. 7F shows Western blot analysis of DNase X in HEK293 cells transfected with DNase X siRNA or scrambled control siRNA. Actin was used as a protein loading control. FIG. 7G shows *E. chaffeensis* load in HEK293 cells treated with DNase X siRNA or scrambled control siRNA at 48 h pi. qPCR for *E. chaffeensis* 16S rDNA normalized with human G3PDH DNA. Data represent the mean and standard deviation of triplicate samples and are representative of three independent experiments. *Significantly different (P<0.05). FIG. 7H is a bar graph showing numbers of total cell-associated and internalized *E. chaffeensis* in DNase $X^{-/-}$ or wild-type BMDMs at 4 h pi. Cells were processed for two rounds of immunostaining with a-P28 as described in FIG. 1E. The total numbers of *E. chaffeensis* in 100 cells were scored. Data represent the mean and standard deviation of triplicate samples and are representative of three independent experiments. The black bar represents total *E. chaffeensis*, and the white bar represents internalized *E. chaffeensis* (total minus external). *Significantly different (P<0.05) FIGS. 7I and 7J show *E. chaffeensis* load in BMDMs from DNase $X^{-/-}$ mice and wild-type mice at 56 h pi (I) or in the blood at 5 days post-infection from DNase $X^{-/-}$ mice and wild-type mice (J). qPCR for *E. chaffeensis* 16S rDNA was performed and normalized with mouse G3PDH DNA. Data represent the mean and standard deviation of triplicate samples and are representative of three independent experiments. *Significantly different (P<0.05).

FIGS. 10A-10B show that anti-EtpE-C neutralizes *E. chaffeensis* binding and entry into THP-1 cells, related to FIG. 1D-F. FIG. 10A is a bar graph showing numbers of *E. chaffeensis* (Ech) bound to THP-1 cells at 30 min pi. *E. chaffeensis* was pretreated with anti-EtpE-C or preimmune mouse serum and incubated with THP-1 cells for 30 min. Unbound *E. chaffeensis* was washed away, cells were fixed with PFA and *E. chaffeensis* was labeled with anti-P28 without permeabilization. *E. chaffeensis* in 100 cells was scored. FIG. 10B is a bar graph showing numbers of *E. chaffeensis* internalized into THP-1 cells at 2 h pi. Purified host cell-free *E. chaffeensis* was pretreated with anti-rEtpE-C or preimmune mouse serum and incubated with THP-1 cells for 2 h. To distinguish intracellular from bound *E. chaffeensis*, unbound *E. chaffeensis* was washed away, and cells were processed for two rounds of immunostaining with anti-P28: first without permeabilization to detect bound but not internalized *E. chaffeensis* (AF555-conjugated secondary antibody), and another round with saponin permeabilization to detect total *E. chaffeensis*, i.e., bound plus internalized (AF488-conjugated secondary antibody). The black bar represents total *E. chaffeensis*, and the white bar represents internalized *E. chaffeensis* (total minus bound). *E. chaffeensis* in 100 cells was scored. qPCR for *E. chaffeensis* 16S rDNA was normalized with human G3PDH DNA. Data represent the mean and standard deviation of triplicate samples and are representative of three independent experiments. *Significantly different (P<0.05).

FIGS. 11A-11B show that anti-P28 does not inhibit binding or uptake of *E. chaffeensis* by THP-1 cells, related to FIG. 1D-F. FIG. 11A is a bar graph showing relative radioactivity representing numbers of *E. chaffeensis* bound to THP-1 cells. Host cell-free radiolabeled *E. chaffeensis* preincubated with Fab fragment of rabbit anti-P28 IgG or pre-immune rabbit IgG were incubated with THP-1 cells for 2 h at 4° C. Unbound *E. chaffeensis* was washed away, and radioactivity of bound *E. chaffeensis* was measured. FIG. 11B is a bar graph showing relative radioactivity representing numbers of *E. chaffeensis* internalized into THP-1 cells. Host cell-free radiolabeled *E. chaffeensis* preincubated with Fab fragment of rabbit anti-P28 IgG or pre-immune rabbit IgG was incubated with THP-1 cells for 3 h at 37° C. Bound uninternalized *E. chaffeensis* was removed by pronase E treatment, radioactivity of internalized *E. chaffeensis* measured. Data represent the mean and standard deviation of triplicate samples and are representative of two independent experiments.

FIG. 12A is a bar graph showing *E. chaffeensis* 16S rDNA in RF/6A cells infected with *E. chaffeensis*. *E. chaffeensis* was pretreated with anti-EtpE-N or preimmune rabbit serum and used to infect RF/6A cells; cells were harvested at 48 h pi. qPCR for *E. chaffeensis* 16S rDNA was normalized with monkey G3PDH DNA. Data represent the mean and standard deviation of triplicate samples and are representative of three independent experiments. *Significantly different (P<0.05). FIG. 12B shows immunofluorescence labeling of live host cell-free *E. chaffeensis*. Unfixed *E. chaffeensis* was first incubated with anti-EtpE-C, EtpE-N, or P28 (ECHP28); then fixed and labeled with AF555-conjugated secondary antibodies. Scale bar, 10 μm.

FIG. 15A contains fluorescence and DIC merged images of rEtpE-C-coated, rECH0825-coated and non-coated beads incubated with BMDMs from wild-type and DNase X$^{-/-}$ mice. Beads were incubated with cells for 30 min at 4° C. followed by rigorous washing with PBS to remove unbound or loosely-adherent beads. Scale bar, 5 µm. FIG. 15B is a bar graph showing numbers of internalized rEtpE-C-coated beads/cell of similar experiment as (A), relative to the number of rECH0825-coated beads bound to wild-type BMDM set as 100. Data represent the mean and standard deviation of triplicate samples and are representative of three independent experiments. *Significantly different (P<0.05).

DETAILED DESCRIPTION

Figure 1A:
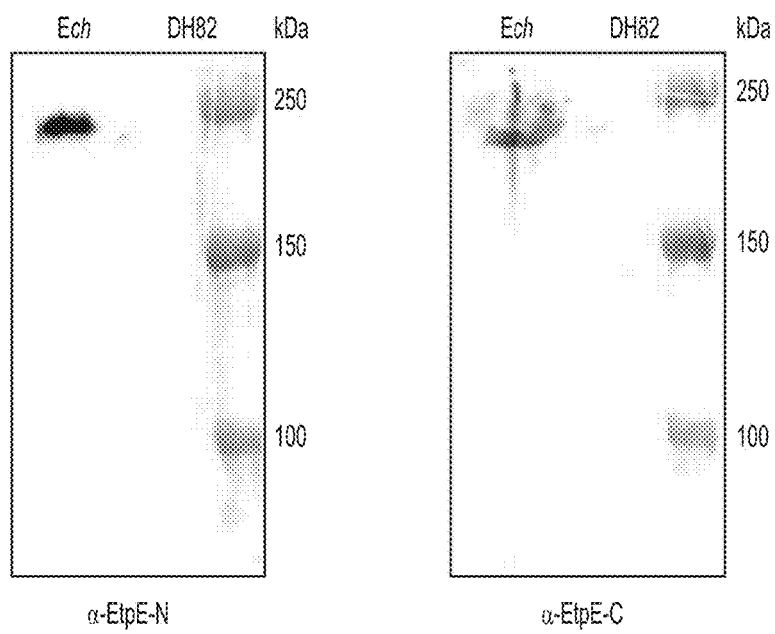

The comparative genome hybridization study of *E. chaffeensis* strains revealed that a hypothetical protein, ECH1038, consists of highly conserved N- and C-terminal segments flanking its strain-variable central region. ECH1038 expression is up-regulated in the DC stage of *E. chaffeensis*. As disclosed herein, ECH1038 (here named as entry triggering protein of *Ehrlichia*, EtpE), particularly its C-terminal conserved region (EtpE-C), is critical for *E. chaffeensis* binding, entry, and infection of several different host cell types. DNase X, a host cell surface GPI-anchored protein, is the receptor of EtpE-C mediating the entry of *E. chaffeensis* into several mammalian cell types permissive to its replication. Moreover, immunization with rEtpE-C is also shown herein to protect mice against *Ehrlichia* sp. challenge. Further, antibodies to both the EtpE-C and the N-terminal region ("EtpE-N") can be found in subjects infected with *Ehrlichia* sp. Importantly, the EtpE-N is highly conserved across *Ehrlichia* sp. Therefore, disclosed herein are vaccines, diagnostics, and cell delivery polypeptides and uses therefore that take advantage of these unique properties of EtpEs.

Immunogenic polypeptides are disclosed that contain all or part of an EtpE protein from an *Ehrlichia* sp. This encompasses active fragments and variants of the immunogenic polypeptide. Thus, the term "immunogenic or antigenic polypeptide" further contemplates deletions, additions and substitutions to the disclosed sequences, so long as the polypeptide functions to produce an immunological response as defined herein.

For example, the immunogenic polypeptide can comprise the amino acid sequence SEQ ID NO:1 (EtpE from *Ehrlichia chaffeensis* str. Arkansas; Accession No. YP_507823.1), SEQ ID NO:3 (EtpE from *Ehrlichia canis* str. Jake; Accession No. AAZ68869.1), or SEQ ID NO:5 (EtpE from *Ehrlichia ruminantium* str. Welgevonden; Accession No. YP_180660.1). EtpE homologues from other *Ehrlichia* sp. can also be identified and used to improve species cross-reactivity.

Importantly, genome sequencing has resulted in nomenclature changes and in some cases reclassification of both genus and species in the past. It is therefore possible, that members of the *Ehrlichia* genus could be reclassified as a different species sometime in the future. Less likely, but still possible, is the future reclassification of a species in or out of the *Ehrlichia* genus. Therefore, while reference to species and genus is meaningful, it is also understood that genus classification is less important than the presence of homologous/orthologous EtpE proteins in the related organism, which can be identified and confirmed independently from genus/species classification.

In some embodiments, the vaccine contains an immunogenic fragment of an EtpE protein that is capable of eliciting an immune response against an *Ehrlichia* sp. Preferably, the immunogenic fragment comprises at least a portion of the conserved region ("EtpE-C"). For example, the one or more polypeptide can comprise the amino acid sequence SEQ ID NO:2 (residues 1656-1963 of SEQ ID NO:1), SEQ ID NO:4 (residues 1408-1510 of SEQ ID NO:3), SEQ ID NO:6 (residues 1410-1710 of SEQ ID NO:5), or a an immunogenic fragment thereof capable of eliciting an immune response against an *Ehrlichia* sp.

The vaccine can alternatively contain an immunogenic variant of an EtpE protein, or fragment thereof, that is capable of eliciting an immune response against an *Ehrlichia* sp. For example, the vaccine can comprise one or more polypeptides having an amino acid sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to an amino acid sequence selected from the group consisting of SEQ ID NO:1, SEQ ID NO:3, SEQ ID NO:5, or an immunogenic fragment thereof capable of eliciting an immune response against an *Ehrlichia* sp. The vaccine can comprise one or more polypeptides having an amino acid sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:2, SEQ ID NO:4, SEQ ID NO:6, or a an immunogenic fragment thereof capable of eliciting an immune response against an *Ehrlichia* sp.

The vaccine comprises polypeptides representing the EtpE from at least one *Ehrlichia* sp. However, to improve cross-reactivity, the vaccine can contain polypeptides representing the EtpE from at least 2, 3, 4, 5, 6, or more *Ehrlichia* sp. These polypeptides can be in a single amino acid sequence, such as fusion protein. The polypeptides can also be conjugated together on a single carrier molecule. For example, the polypeptides can be used in a multiple antigen peptide system (MAPS).

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography). Chimeric proteins can also be manufactured with toxins or anti-bodies attached to them in order to study disease development.

Alternatively, internal ribosome entry sites (IRES) elements can be used to create multigene, or polycistronic, messages. IRES elements are able to bypass the ribosome scanning model of 5' methylated Cap dependent translation and begin translation at internal sites. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In some embodiments, the vaccine is capable of eliciting an immune response against at least *Ehrlichia chaffeensis*. In these embodiments at least one of the one or more polypeptides comprise SEQ ID NO:1, SEQ ID NO:2, or an immunogenic variant or fragment thereof capable of eliciting an immune response against *Ehrlichia chaffeensis*.

In some embodiments, the vaccine is capable of eliciting an immune response against at least *Ehrlichia canis*. In these embodiments at least one of the one or more polypeptides comprise SEQ ID NO:3 or an immunogenic variant or fragment thereof capable of eliciting an immune response against *Ehrlichia canis*.

In some embodiments, the vaccine is capable of eliciting an immune response against at least *Ehrlichia ruminantium*. In these embodiments at least one of the one or more polypeptides comprise SEQ ID NO:5 or an immunogenic variant or fragment thereof capable of eliciting an immune response against *Ehrlichia ruminantium*.

In some embodiments, the vaccine is capable of eliciting an immune response against any combination of *Ehrlichia chaffeensis*, *Ehrlichia canis*, and *Ehrlichia ruminantium*. The vaccine can also be capable of eliciting an immune response against other species, such as *Ehrlichia muris*, *Ehrlichia ewingii*, or a combination thereof. The EtpE homologue from these and other species and strains can be identified and used as immunogens as described herein.

Adjuvants suitable for use with the disclosed vaccine are known and include Quil A, aluminum salts, squalene, virosomes, and combinations thereof. Likewise, immune stimulants suitable for use with the disclosed vaccine are known and include cytokines, growth factors, chemokines, and combinations thereof.

Also disclosed is a recombinant vector that contains a nucleic acid sequence encoding any of the one or more immunogenic polypeptides disclosed herein, operatively linked to a heterologous promoter. Suitable vectors for propagating and/or expressing the nucleic acid sequence encoding any of the one or more immunogenic polypeptides are known in the art. In some embodiments, the vector is a plasmid selected from the group consisting of pcDNA3, pCI, VR1020, VR1012, and VR1055. These are mammalian expression plasmids which usually consist of a strong viral promoter to drive the in vivo transcription and translation of the gene (or complementary DNA) and include a strong polyadenylation/transcriptional termination signal. For example, VR1055 vector contains HCMV promotor, intron A (to improve mRNA stability) and multicloning site, mRBG (minimal rabbit globin terminator) and kanamycin selection marker. A bacterial DNA sequence codon-optimized for mammalian expression is inserted at the multicloning site.

In some embodiments, the vector is a recombinant viral vector. For example, the recombinant viral vector can be selected from the group consisting of poxvirus, adenovirus, adeno-associated virus, lentivirus, and herpesvirus. A live virus vector vaccine uses a weakened replication defective virus to transport genes encoding bacterial DNA sequence to elicit immune response to the bacterial protein. For example, a modified ACAM2000 vaccinia virus (VACV) that is further reduced of its virulence potential through deletion of thymidine kinase (TK; J2R) and IL-18 binding protein (IL18BP; C12L). The inactivation of the TK gene greatly reduces VACV virulence. In fact, a TK-null VACV, JX-594, was shown to be safe as an oncolytic virus for cancer patients in phase I clinical trial. Since viral envelop proteins elicit strong B- and T-cell immune responses, a fusion protein of viral envelop protein such as D8 and the bacterial protein is constructed and inserted into viral genome to produce a recombinant virus.

Suitable promoters for driving expression of nucleic acids encoding the disclosed polypeptides are also known and can be selected, for example, from the group consisting of human or murine cytomegalovirus major immediate early (IE) promoter (CMV-IE), the early/late promoter of the SV40 virus, and the LTR promoter of the Rous sarcoma virus. In some embodiments, a viral promoter can be used to drive a downstream gene encoding a fusion between a part of viral protein (for example, the transmembrane domain of D8 of VACV and EtpE-C (codon optimized).

Also disclosed is a vaccine containing any of the disclosed recombinant vectors in a pharmaceutically acceptable vehicle, diluent or excipient. The vaccine can further contain a pharmaceutically acceptable adjuvant. Suitable adjuvants for use with DNA vaccines are known and include, for example, an oligonucleotide comprising a CpG motif, or a vector encoding one or more growth factors, cytokines, chemokine, or combination thereof. For example, the growth factor can be granulocyte macrophage colony-stimulating factor (GM-CSF).

Also disclosed is a method for vaccinating a subject against *Ehrlichia sp*, that comprises administering to the subject a composition comprising any of the disclosed vaccines. The subject can be any mammal at risk for *Ehrlichia sp*. infection. In particular, the subject can be a human, canine, feline, bovine, ovine, or caprine subject. The method provides a protective immune response against at least one *Ehrlichia sp*. selected from the group consisting of *Ehrlichia chaffeensis*, *Ehrlichia canis*, and *Ehrlichia ruminantium*. However, in preferred embodiments, the vaccine elicits a protective immune response in the subject against at least 2, 3, 4, 5, 6, or more *Ehrlichia sp*.

Also disclosed is a method for diagnosing Ehrlichiosis in a subject that comprising assaying a biological sample (e.g., blood, serum, or plasma sample) from the subject for the presence of an antibody that specifically binds an EtpE polypeptide. In particular, assaying for antibodies that specifically bind an EtpE-N provides pan-diagnosis of *Ehrlichia sp*. infection since the N-terminal domain is highly conserved across species. Therefore, in some embodiments, the presence of the antibody is an indication that the subject has been infected with an *Ehrlichia* sp. selected from the group consisting of *Ehrlichia chaffeensis*, *Ehrlichia canis*, *Ehrlichia ruminantium*, or any combination thereof. Therefore, the method can involve assaying a biological sample from the subject for the presence of an antibody that specifically binds SEQ ID NO:7 (amino acid residues 29-708 of SEQ ID NO:1), SEQ ID NO:8 (amino acid residues 73-736 of SEQ ID NO:3), SEQ ID NO:9 (amino acid residues 39-730 of SEQ ID NO:5), or a conservative variant thereof having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:7, SEQ ID NO:8, or SEQ ID NO:9, wherein the presence of the antibody is an indication that the subject has been infected with an *Ehrlichia* sp.

In some aspects, the method is an immunoassay. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In some embodiments, the method provides a pan-diagnostic so that one test can be used for multiple species of *Ehrlichia*. However, in some embodiments, the method also diagnoses the specific *Ehrlichia* sp. In these embodiments, the EtpE-C polypeptide can be used to detect antibodies that selectively bind the C-terminal region of an EtpE from a specific species of *Ehrlichia*. This is useful since prognosis (choronic vs. acute disease) and zoonotic potential are different depending on the species of *Ehrlichia*. Although all of these species can infect humans, levels of zoonosis potential is in the order of *E. chaffeensis*>*E. ewingii*>*E. muris*>*E. canis*>*E. ruminantium*. *E. chaffeensis* infection in humans is acute, and can be fatal. *E. canis* infection is chronic and debilitating febrile illness in dogs (infection for life if not treated at early stage of infection). Clinical signs of *E. canis* infection in humans is generally mild, but can be severe. *E. canis* can also infect cats, and clinical signs of cats are similar to those in infected dogs. *E. ewingii* infection in humans is acute, and some case is associated with infection of pet dogs (*E. chaffeensis* is not, since its major reservoir is wild deer). *E. ewingii* infection of dogs is chronic. Wild rodents are the reservoir of *E. muris* (chronic infection), and clinical signs of human infection without underlining other diseases is relatively mild, and has been transmitted between humans via blood transfusion of contaminated blood. *E. ruminantium* causes acute and chronic debilitating disease accompanied with neurological signs (heart water, often fatal) of ruminants (cattle, goat, sheep) in Africa and Caribbean countries. Only rare cases of human infection with *E. ruminantium* (severe, acute) have been reported.

The disclosed methods can further comprise treating the subject for Ehrlichiosis if the antibody is detected. For example, the method can comprise treating the subject with an effective amount and duration of doxycycline if the antibody is detected. This should be done as early as possible, since at later stage of infection antibiotic becomes less effective in clearing bacteria or clinical signs. Therefore, early detection by the disclosed methods can improve treatment efficacy.

Also disclosed is a method for monitoring the treatment of a subject for Ehrlichiosis that comprises assaying a biological sample from the subject for levels of an antibody that specifically binds a polypeptide comprising SEQ ID NO:7, SEQ ID NO:8, or SEQ ID NO:9, or a conservative variant thereof having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:7, SEQ ID NO:8, or SEQ ID NO:9. In these methods, an at least 2-, 3-, or 4-fold titer reduction in antibody levels is an indication that the treatment is effective. Of course, with chronic stage disease, this can take several months. Therefore, the method can involve assaying a sample from the subject every 1, 2, 3, 4, 5, or 6 weeks to monitor the treatment. Once antibody levels are no longer detectable, the method can further involve ceasing treatment. Alternatively, if antibody levels do not decrease as expected, then the method can further comprising altering the treatment, such as by increasing dosages or selecting an alternative antibiotic.

Also disclosed is a method for delivering a therapeutic or diagnostic agent to a cell in a subject that involves conjugating the agent, or a delivery vehicle comprising the agent, to a EtpE-C polypeptide. For example, the method can comprise administering to the subject a composition comprising the agent, wherein the agent, or a delivery vehicle comprising the agent, is conjugated to a delivery polypeptide comprising an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:2, SEQ ID NO:4, SEQ ID NO:6, or a fragment thereof capable of binding DNase X, or to a nucleic acid encoding the polypeptide operably linked to a promoter.

In some embodiments, the polypeptide comprises at least 100, 101, 102, 103, 104, 105, 110, 120, 130, 140, 150, 160, 170, 180, 190, or 200 amino acids of SEQ ID NO:2, SEQ ID NO:4, or SEQ ID NO:6.

In some embodiments, the polypeptide comprises at least residues 1658 to 1761 of SEQ ID NO:1, including residues 1658 to 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1842, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, or 1963 of SEQ ID NO:1, or a conservative variant thereof.

In some embodiments, the polypeptide comprises at least residues 1408 to 1510 of SEQ ID NO:3. In some embodiments, the polypeptide comprises at least residues 1410 to 1510 of SEQ ID NO:5, including residues 1408 to 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1542, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1961, 1662, 1663, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, or 1710 of SEQ ID NO:5.

The therapeutic or diagnostic agent can be any pharmaceutically acceptable substance for which delivery to a cell in a subject is desired. The agent can be a therapeutic drug (e.g., small molecule) or biologic (e.g., antibody, peptide, growth factor). The diagnostic agent can be a molecule detectable in the body of a subject by an imaging technique such as X-ray radiography, ultrasound, computed tomography (CT), single-photon emission computed tomography (SPECT), magnetic resonance imaging (MRI), positron emission tomography (PET), Optical Fluorescent Imaging, Optical Visible light imaging, and nuclear medicine including Cerenkov Light Imaging. For example, the diagnostic agent can comprise a radionuclide, paramagnetic metal ion, or a fluorophore. Fluorophores emit energy throughout the visible spectrum; however, the best spectrum for in vivo imaging is in the near-infrared (NIR) region (650 nm-900 nm). Unlike the visible light spectrum (400-650 nm), in the NIR region, light scattering decreases and photo absorption by hemoglobin and water diminishes, leading to deeper tissue penetration of light. Furthermore, tissue auto-fluorescence is low in the NIR spectra, which allows for a high signal to noise ratio. There is a range of small molecule organic fluorophores with excitation and emission spectra in the NIR region. Some, such as indocyanine green (ICG) and cyanine derivatives Cy5.5 and Cy7, have been used in imaging for a relatively long time. Modern fluorophores are developed by various biotechnology companies and include: Alexa dyes; IRDye dyes; VivoTag dyes and HylitePlus dyes. In general, the molecular weights of these fluorophores are below 1 kDa. In some embodiments, the diagnostic agent comprises a radiocontrast agent. Examples of suitable radiocontrast agents include iohexol, iodixanol and ioversol.

The disclosed delivery polypeptide can be conjugated to agents using known techniques, depending on the type of agent selected. For example, where the agent is a polypeptide, the composition can be a fusion protein that contains both the agent and the delivery polypeptide. Likewise, the composition can comprises a DNA expression vector encoding a fusion protein comprising the agent and the delivery polypeptide operably linked to a promoter. In some embodiments, the composition comprises a nanoparticle, microparticle, or microsphere encapsulating the agent. In these embodiments, the delivery polypeptide can be positioned on the surface of the nanoparticle, microparticle, or microspheres to facilitate delivery. For example, the microsphere can comprise lactide-co-glycoid or a polyanhydride. In some embodiments, the composition comprises a biodegradable polymer conjugated to the delivery polypeptide.

The disclosed method can be used to deliver the agent to any cell expressing DNase X. In addition to leukocyte, endothelial cells, and kidney cells, DNase X is highly expressed in heart, brain, and placenta. Cells from these tissues can be targeted for EtpE-C-DNase X-mediated gene or drug delivery. A key premise for the success of cardiac gene therapy is the development of powerful gene transfer vehicles that can achieve highly efficient and persistent gene transfer specifically in the heart. For example, the delivery mechanism can be used to deliver vascular endothelial growth factor DNA to stimulate stem cells of cardiac and skeletal muscles in vivo or to grow the cells in cell culture system to transplant matured muscle cells to regenerate the damaged tissue. Leukemia cells can be treated through autologous transplantation of hematopoietic stem cells gene-modified in vitro by delivering a normal gene into hematopoietic stem cells.

Disclosed are pharmaceutical compositions containing therapeutically effective amounts of one or more of the disclosed polypeptides, nucleic acids, or vaccines and a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. Pharmaceutical carriers suitable for administration of the molecules provided herein include any such carriers known to those skilled in the art to be suitable for the particular mode of administration.

The polypeptides, nucleic acids, or vaccines can be formulated for a variety of routes of administration and/or applications. Suitable dosage forms for parenteral administration include solutions, suspensions, and emulsions. Typically, the polypeptides, nucleic acids, or vaccines are dissolved or suspended in a suitable solvent such as, for example, water, Ringer's solution, phosphate buffered saline (PBS), or isotonic sodium chloride. The formulation may also be a sterile solution, suspension, or emulsion in a nontoxic, parenterally acceptable diluent or solvent such as 1,3-butanediol. Formulations may further include one or more additional excipients. Representative excipients include solvents, diluents, pH modifying agents, preservatives, antioxidants, antinfective agents, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions. In some cases, formulations can include one or more tonicity agents to adjust the isotonic range of the formulation. Suitable tonicity agents are well known in the art and include glycerin, mannitol, sorbitol, sodium chloride, and other electrolytes. In some cases, the formulations can be buffered with an effective amount of buffer necessary to maintain a pH suitable for parenteral administration. Suitable buffers are well known by those skilled in the art and some examples of useful buffers are acetate, borate, carbonate, citrate, and phosphate buffers. In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

The exact amount of the disclosed compositions administered to a subject will vary from subject to subject, depending on the nature of the diagnostic or therapeutic agent, the species, age, weight and general condition of the subject, the mode of administration and the like. Effective dosages and schedules for administering the compositions may be determined empirically, and making such determinations is within the skill in the art. The dosage ranges for the administration of the compositions are those large enough to produce the desired effect (e.g., a therapeutic result or a suitable diagnostic result). The dosage should not be so large as to cause adverse side effects, such as unwanted cross-reactions, anaphylactic reactions, and the like. The dosage can be adjusted by the individual physician in the event of any counterindications.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "transformation" and "transfection" mean the introduction of a nucleic acid, e.g., an expression vector, into a recipient cell including introduction of a nucleic acid to the chromosomal DNA of said cell.

As used herein, the term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

Variants also include allelic variants. The term "allelic variant" refers to a polynucleotide or a polypeptide containing polymorphisms that lead to changes in the amino acid sequences of a protein and that exist within a natural population (e.g., a virus species or variety). Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the disclosed polypeptides and nucleic acids.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "immunogenic" as used herein refers to a composition that is able to provoke an immune response against it.

The term "immune response" as used herein refers to the reaction of the immune system to the presence of an antigen by making antibodies to the antigen. In further specific embodiments, immunity to the antigen may be developed on a cellular level, by the body as a whole, hypersensitivity to the antigen may be developed, and/or tolerance may be developed, such as from subsequent challenge. In specific embodiments, an immune response entails lymphocytes identifying an antigenic molecule as foreign and inducing the formation of antibodies and lymphocytes capable of reacting with it and rendering it less harmful.

The term "immunoreactive" as used herein refers to a composition being reactive with antibodies from the sera of an individual. In specific embodiments, a composition is immunoreactive if an antibody recognizes it, such as by binding to it.

The term "ortholog" as used herein refers to a polynucleotide from one species that corresponds to a polynucleotide in another species; the two polynucleotides are related through a common ancestral species (a homologous polynucleotide). However, the polynucleotide from one species has evolved to become different from the polynucleotide of the other species.

The term "vaccine" as used herein refers to a composition that provides immunity to an individual upon challenge.

The term "subunit vaccine" as used herein refers to a vaccine wherein a polypeptide or fragment thereof is employed, as opposed to an entire organism.

A number of embodiments of the invention have been described. Nevertheless, it will be understood that various modifications may be made without departing from the spirit and scope of the invention. Accordingly, other embodiments are within the scope of the following claims.

EXAMPLES

Example 1

ECH1038 (EtpE) is Highly Expressed by *E. chaffeensis* in Mammalian Cells

Materials and Methods

*E. chaffeensis* and host cell culture. *E. chaffeensis* Arkansas type strain was propagated in DH82 cells, and host cell-free *E. chaffeensis* was obtained by controlled sonication as described [Rikihisa Y, et al. (1994) J Clin Microbiol 32: 2107-2112; Barnewall R E, et al. (1994) Infect Immun 62: 4804-4810]. Human peripheral blood monocytes were derived from buffy coats; HEK293, RF/6A and THP-1 cells were cultured as previously described [Liu H, et al. (2012) Cell Microbiol 14: 1037-1050; Miura K, et al. (2011) Infect Immun 79: 4947-4956; Barnewall R E, et al. (1994) Infect Immun 62: 4804-4810]. BMDMs were established from wild-type and DNase X$^{-/-}$ mice as described [Miura K, et al. (2011) Infect Immun 79: 4947-4956].

Production of recombinant proteins rEtpE-N and rEtpE-C, and antisera against them. DNA fragments encoding EtpE-C and EtpE-N were amplified by PCR with Phusion high-fidelity DNA polymerase (NEB) using E. chaffeensis chromosomal DNA as template. The fragments were cloned into pET33b(+) vector (Novagen); recombinant proteins were expressed in E. coli BL21 (DE3) and purified by Ni-affinity chromatography. The antibody against rEtpE-C was produced in ICR mice (Harlan), and the antibody against rEtpE-N was produced in rabbits.

Statistical analysis. Statistical analysis was performed by unpaired two-tailed Student's t-test. $P<0.05$ was considered to be significant.

Results

ECH1038 (GenBank accession no. YP_507823, EtpE) consists of 1963 amino acid residues (Mr 222,638, pI: 7.0) and is predicted to be an outer membrane protein with an N-terminal secretion signal by PSORT analysis [Miura K, Rikihisa Y (2007) Infect Immun 75: 3604-3613]. Although EtpE is variable in the central approximately 950 residues, the N-terminal approximately 700 residues and C-terminal approximately 300 residues are conserved among multiple E. chaffeensis strains of distinct virulence, suggesting that these two regions are indispensable for E. chaffeensis. The amino acid sequence of EtpE orthologs in the three strains of E. chaffeensis, Arkansas, Wakulla, and Liberty are provided in SEQ ID NO:1 (YP_507823), SEQ ID NO:10 (Accession No. DQ924562), and SEQ ID NO:11 (Accession No. DQ924563), respectively. Amino acid sequence alignment of EtpE orthologs among three genome-sequenced Ehrlichia species, E. chaffeensis Arkansas, E. canis Jake and E. ruminantium Welgevonden, revealed that while most of the N-terminal proximal region was conserved also among Ehrlichia species, the C-terminal region was not.

To begin probing EtpE function, N-terminal (residues 29-708) and C-terminal (residues 1656-1963) of EtpE were cloned as C-terminal histidine-tagged fusion proteins (rEtpE-N and rEtpE-C) and antisera were prepared against rEtpE-N and rEtpE-C. Western blot analysis using these antibodies showed that full-length EtpE was expressed by E. chaffeensis in DH82 cells (FIG. 1A). DH82 cells were initially used, since this cell line has been successfully used to culture isolate E. chaffeensis from the blood of HME patients [Dawson J E, et al. (1991) J Clin Microbiol 29: 2741-2745; Paddock C D, et al. (1997) J Clin Microbiol 35: 2496-2502].

Figure 1B:
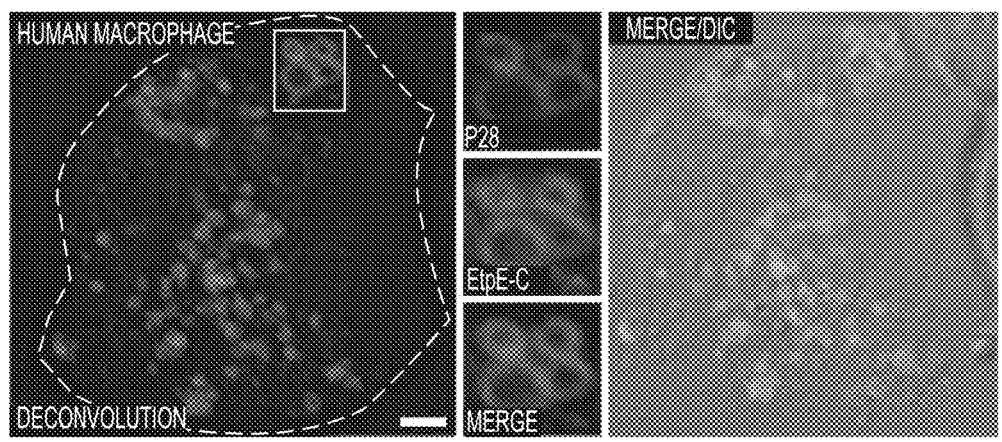

To determine whether EtpE is expressed by E. chaffeensis in human monocytes, the pathogen's primary in vivo target cells, EtpE expression was determined in E. chaffeensis cultured in human primary macrophages derived from peripheral blood monocytes by double immunofluorescence labeling after paraformaldehyde (PFA) fixation and saponin permeabilization. E. chaffeensis major outer membrane protein P28 [Ohashi N, et al. (1998) Infect Immun 66: 132-139] was used as positive control to label the bacterial membrane. The results showed that EtpE was abundantly expressed by E. chaffeensis in human macrophages, and localized at bacterial membrane like P28 [Ohashi N, et al. (1998) Infect Immun 66: 132-139] (FIG. 1B).

Example 2

EtpE is Exposed on the E. chaffeensis Surface, and Anti-EtpE-C Inhibits E. chaffeensis Binding, Entry, and Infection Materials and Methods Binding and internalization assay of E. chaffeensis and immunostaining of host cell-free E. chaffeensis. Coverslip cultures of DH82, HEK293, RF/6A cells, or macrophages differentiated from human peripheral blood monocytes or established from bone-marrow of DNase X$^{-/-}$ or congenic wild-type mice and suspension culture of THP-1 cells were incubated with E. chaffeensis freshly isolated from infected cells at approximate multiplicity of infection (MOI) of 200, unless otherwise noted, for 30 to 45 min for binding assays or 2 to 4 h for internalization assays at 37° C. in 5% $CO^2$/95% air. Cells were washed with phosphate-buffered saline (PBS: 137 mM NaCl, 2.7 mM KCl, 8.1 mM $Na_2HPO_4$, 1 mM $KH_2PO_4$, pH 7.4) to remove unbound bacteria and labeled with antibodies as described [Wang X, et al. (2006) Infect Immun 74: 1873-1882]. For binding assay cells were fixed with 3% PFA and labeled with mouse monoclonal anti-DNase X (Abcam), rabbit anti-E. chaffeensis P28 [Ohashi N, et al. (1998) Infect Immun 66: 132-139], mouse anti-rEtpE-C, or dog anti-E. chaffeensis [Barnewall R E, et al. (1997) Infect Immun 65:1455-1461] as primary antibodies and Alexa Fluor (AF) 488-conjugated goat anti-mouse IgG, AF555-conjugated goat anti-rabbit IgG (Invitrogen), or Texas Red-conjugated goat anti-dog IgG (Jackson ImmunoLab) as secondary antibodies. For internalization assays, two steps of labeling of fixed cells with anti-P28 were carried out as described: the first labeling step was performed without saponin permeabilization using AF488-conjugated goat anti-rabbit IgG, and the second labeling was performed with permeabilization using AF555-conjugated goat anti-rabbit IgG [Niu H, et al. (2006) Cell Microbiol 8: 523-534]. Fluorescent images were acquired using a Nikon Eclipse E400 fluorescence microscope with a xenon-mercury light source (Nikon), Deltavision deconvolution microscope (Applied Precision) with 0.2 or 0.4-µm step size along the z-axis of the cells, or an LSM 510 laser-scanning confocal microscope (Carl Zeiss). For immunostaining of live bacteria, host cell-free E. chaffeensis was incubated with anti-EtpE-C, anti-EtpE-N or E. chaffeensis P28 for 1 h at room temperature followed by fixing with 3% PFA and labeling with AF555-conjugated goat anti-mouse or anti-rabbit antibodies. To further demonstrate the surface exposure of EtpE, host cell-free E. chaffeensis was incubated with either pronase E (Sigma) at a concentration of 2 mg/ml in PBS or vehicle control for 15 min at 37° C. [Yoshiie K, et al. (2000) Infect Immun 68: 1125-1133]; pronase E was inactivated by adding 10% fetal bovine serum (FBS), followed by washing in PBS twice. The bacteria were cytospun onto glass slides, fixed with 3% PFA, followed by quenching in PBS containing 0.1 M glycine, washed with PBS and labeled sequentially with anti-EtpE-C and anti-CtrA [Cheng Z, et al. (2011) Mol Microbiol 82: 1217-1234] with or without saponin permeabilization followed by AF488 or AF555-conjugated goat anti-mouse or anti-rabbit antibodies.

[$^{35}$S]methionine-labeled E. chaffeensis binding and uptake. Approximately $10^6$ cells of E. chaffeensis-infected THP-1 cells/ml in 2 ml of methionine cysteine-deficient RPMI 1640 medium (ICN Biomedicals) supplemented with 10% FBS and 2 mM L-Gln were incubated with cycloheximide (Sigma) at 10 µg/ml at 37° C. for 1 h. A metabolic labeling reagent (Tran $^{35}$S-Label; 11.7 mCi/ml [1,100 Ci/mmol]; 100 µl; ICN Biomedicals) was added and the mixture was incubated further at 37° C. for 24 h. The radiolabeled *E. chaffeensis* was released by sonication and washed by centrifugation at 10,000×g for 10 min. To study the effect of rabbit anti-P28 on *E. chaffeensis* binding and entry, radiolabeled *E. chaffeensis* cells (40,000 cpm/200 µl) preincubated with Fab fragment of anti-P28 IgG [0.5 mg/ml, prepared using Immobilized papain (Pierce) from IgG affinity purified with AffiPack Immobilized Protein A column (Pierce)] or Fab fragment of normal rabbit IgG (0.5 mg/ml) were added to 1×10$^6$ THP-1 cells in 0.4 ml of RPMI 1640 medium containing 10% FBS and 2 mM L-Gln and incubated at 4° C. for 2 h. The uptake of *E. chaffeensis* was evaluated following removal of bound *E. chaffeensis* cells by incubation with pronase E at 2 mg/ml in PBS at 37° C. for 10 min after incubation of *E. chaffeensis* with THP-1 cells at 37° C. for 3 h. THP-1 cells were washed by centrifugation at 375×g for 5 min, the cells then were dissolved in 0.6 N NaOH and 0.5% SDS, and the radioactivity was measured in a scintillation counter.

Results

Figure 9:
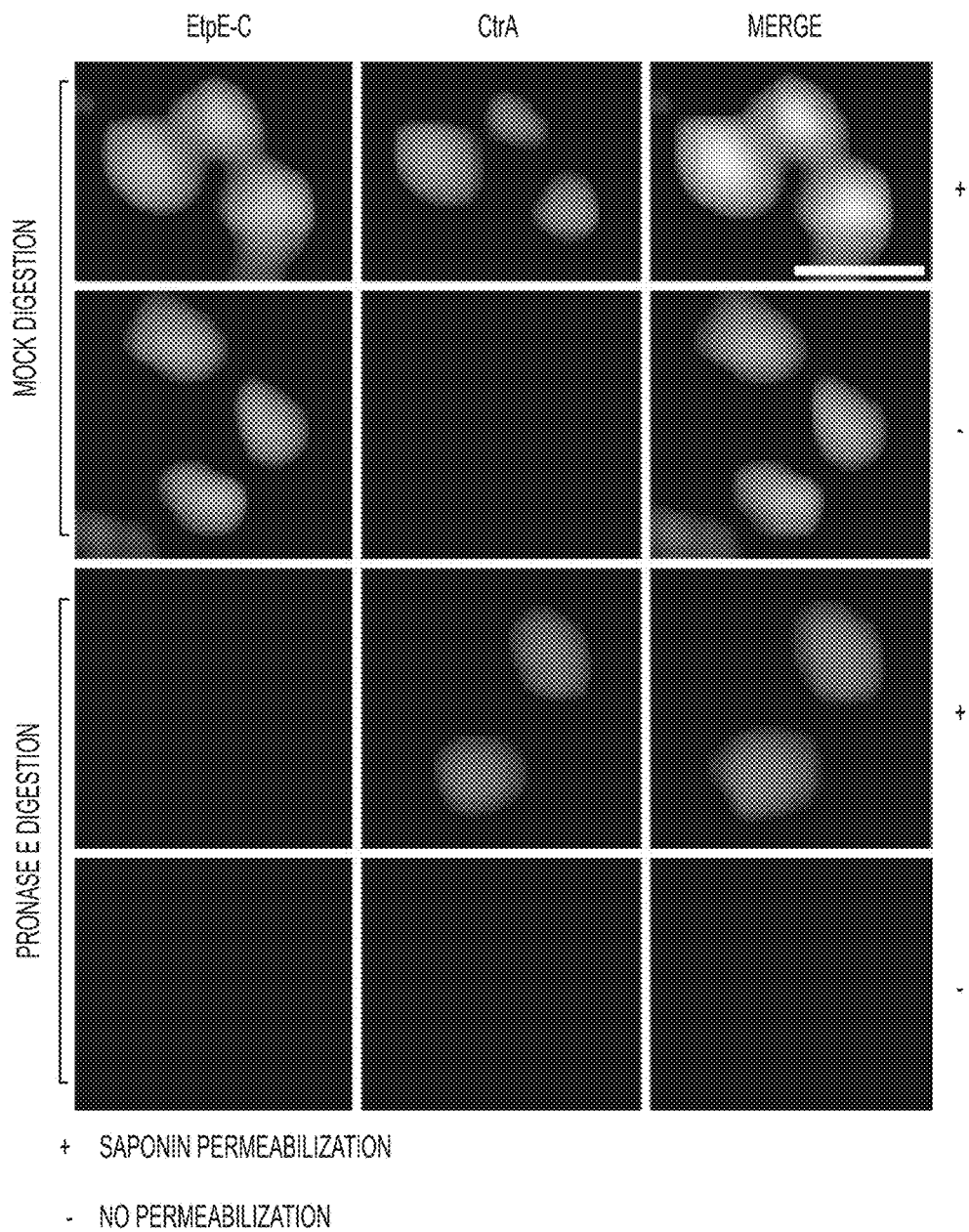
FIG. 9 contains immunofluorescence image showing host cell-free *E. chaffeensis* that was either treated with pronase E or PBS control. Cells were processed for double immunostaining with anti-EtpE-C and anti-CtrA with or without saponin permeabilization as described to distinguish extracellular and internalized bacteria. When bacteria were treated with pronase E, the surface immunofluorescence staining of EtpE was abolished completely, but not that of the internal control CtrA. Scale bar, 1 μm.

P28 is bacterial surface exposed [Ohashi N, et al. (1998) Infect Immun 66: 132-139] and is a β-barrel protein that functions as porin [Kumagai Y, et al. (2008) J Bacteriol 190: 3597-3605]. To determine whether EtpE is exposed on the bacterial surface, double immunofluorescence labeling with anti-EtpE-C and anti-P28 was performed after PFA fixation without saponin permeabilization using *E. chaffeensis* bound to the surface of DH82 cells. Unlike methanol or acetone fixation, PFA fixation does not allow antibody penetration across biological membranes unless with subsequent permeabilization, thereby limiting antibody staining to molecules exposed to the cell surface [Wang X, et al. (2006) Infect Immun 74: 1873-1882]. The result showed labeling of both EtpE and P28 (FIG. 1C). Of note, labeled EtpE on *E. chaffeensis* had a beaded (rosary-like) pattern encircling individual bacterium, in contrast to P28 that had a uniform ring pattern (FIG. 1C). When host cell-free bacteria were treated with pronase E, the surface immunofluorescence staining of EtpE was abolished, but not of CtrA which is an *E. chaffeensis* cytosolic response regulator of a two-component system [Cheng Z, et al. (2011) Mol Microbiol 82: 1217-1234] (FIG. 9). These data indicate the surface exposure of EtpE. In contrast to the punctate labeling pattern of EtpE in host cell-bound bacteria, homogeneous labeling of EtpE was observed on host cell-free bacteria (FIG. 9).

Given the surface exposure of EtpE on *E. chaffeensis*, experiments were conducted to determine whether the antibody against EtpE inhibits binding, entry, and infection of *E. chaffeensis*. Among the several host cell types used in this study, primary monocytes, macrophages, and myelocytic leukemia cell lines (DH82 and THP-1 cells) are referred to as phagocytes. Phagocytes are very efficient in bacteria and particle uptake as they have an array of dedicated phagocytic receptors, including pathogen pattern recognition receptors, mannose receptors, scavenger receptors, receptors for immunoglobulin (FcR) and complement (CR3) that utilize opsonins for ingestion, to name a few [Krieger M (1997) Curr Opin Lipidol 8: 275-280; Aderem A, et al. (1999) Annu Rev Immunol 17: 593-623]. The other two cell lines used in this study, RF/6A endothelial and HEK293 epithelial cells, are referred to as non-phagocytes, since they lack these features. Non-phagocytes were first used to study the effect of in vitro antibody neutralization of EtpE as they lack the response to opsonization and will not readily take-up opsonized particles. *E. chaffeensis* was pre-incubated with mouse anti-EtpE-C or preimmune mouse sera, and then incubated with RF/6A cells. Binding and entry were determined by immunofluorescence labeling of *E. chaffeensis* with anti-P28 at 30 min and 2 h post-incubation/infection (pi), respectively. Infection was determined at 48 h pi by quantitative realtime PCR (qPCR). Anti-EtpE-C blocked *E. chaffeensis* binding, entry, and subsequently infection by approximately 80% compared to preimmune serum (FIG. 1D-1F). Similar level of inhibition of binding and entry was observed using mouse anti-EtpE-C in phagocytic cells such as human THP-1 cells (FIGS. 10A and 10B) and canine DH82 cells. This suggests that human or canine FcR-mediated entry of *E. chaffeensis* opsonized with mouse anti-EtpE-C was negligible in this experiment. Immunization of mice with recombinant P28, which functions as a porin [Kumagai Y, et al. (2008) J Bacteriol 190: 3597-3605], protects mice from *E. chaffeensis* challenge [Ohashi N, et al. (1998) Infect Immun 66: 132-139]. Additionally, in a mouse model of HME, immunization of mice with *Ehrlichia muris* P28 conferred protection from *E. muris* challenge [Crocquet-Valdes P A, et al. (2011) Clin Vaccine Immunol 18: 2018-2025]. As another control, to rule out the possibility that inhibition of binding is a general property of antibody neutralization of any *E. chaffeensis* cell surface proteins, experiments were conducted to determine whether antibody against P28 blocks *E. chaffeensis* binding and entry. The result showed antibody (Fab fragment) against P28 did not block binding or entry of *E. chaffeensis* (FIGS. 11A and 11B). Taken together, these results suggest that EtpE-C potentially serves as an invasin to trigger *E. chaffeensis* entry in both phagocytes and non-phagocytes.

Figure 12A:
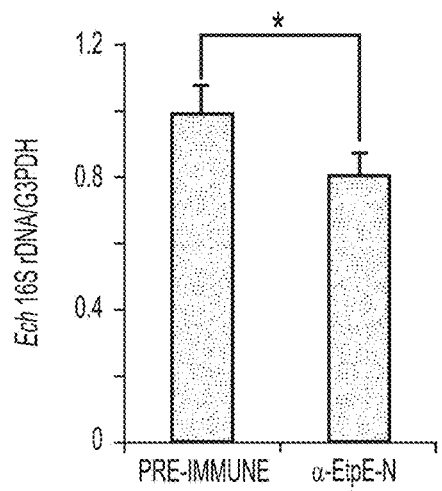
FIGS. 12A-12B show that anti-EtpE-N is not effective in neutralizing *E. chaffeensis* infection in vitro and N-terminus of EtpE is less surface-accessible in live *E. chaffeensis* than its C-terminus, related to FIG. 1.
Figure 12B:
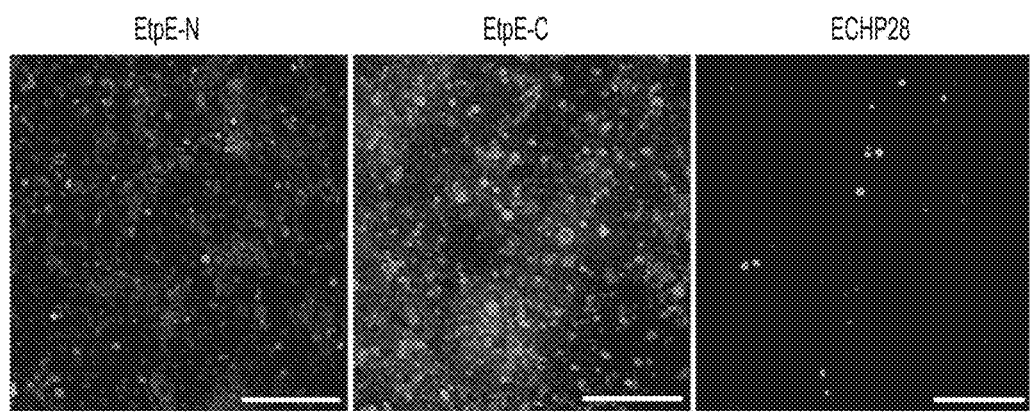

EtpE is predicted to be anchored on the bacterial outer membrane at its N-terminus, based on analysis using the PREDTMBB webserver [Miura K, Rikihisa Y (2007) Infect Immun 75: 3604-3613; Bagos P G, et al. (2004) Nucleic Acids Res 32: W400-404]. In contrast to anti-EtpE-C, anti-EtpE-N-pretreatment reduced *E. chaffeensis* infection by only 20% (FIG. 12A). Since both anti-EtpE-N and anti-EtpE-C reacted with native EtpE protein from *E. chaffeensis* equally well by Western blot analysis, accessibility of anti-EtpE-N to EtpE molecules was tested on live *E. chaffeensis* surface. For this purpose, the host cell-free *E. chaffeensis* was freshly prepared and incubated with the antibodies without pre-fixation. The result showed that *E. chaffeensis* was not as readily labeled with anti-EtpE-N as with anti-EtpE-C (FIG. 12B), suggesting that the antibody access to the N-terminal conserved region might be limited in the native conformation of EtpE in live *E. chaffeensis*.

Example 3

EtpE is Expressed in HME Patients and Infected Dogs, and Immunization with rEtpE-C Suppresses *E. chaffeensis* Infection in Mice Materials and Methods Western blot analysis with sera from HME patients and *E. chaffeensis*-infected dogs. Affinity-purified rEtpE-C and rEtpE-N (5 µg each) were subjected to SDS-PAGE, transferred to a nitrocellulose membrane, and incubated with sera from *E. chaffeensis*-infected dogs (CTUALJ, 3918815, 1425) [Huang H, et al. (2008) Infect Immun 76: 3405-3414], HME patients (ID: MRL1-22, MRL1-40, 72088) [Unver A, et al. (1999) J Clin Microbiol 37: 3888-3895], or control sera. After washing, the membranes were incubated with horseradish peroxidase-conjugated goat anti-dog or anti-human IgG (KPL). Reacting bands were visualized with enhanced chemiluminescence (ECL), images were captured and densitometric analysis was performed using an LAS3000 image documentation system (FUJIFILM Medical Systems).

Mouse infection studies. Two groups of C3H/HeJ mice (4-week-old females; 4 mice per group) (Jackson Laboratories) received either minced SDS-polyacrylamide gel containing 50 µg of rEtpE-C or minced gel alone, with Quil A (Accurate Chemicals) as adjuvant for a total of three times at 14-day intervals. E. chaffeensis challenge was performed 10 days following the last immunization as described [Ohashi N, et al. (1998) Infect Immun 66: 132-139]. DNase $X^{-/-}$ [Rashedi I (2008) The Role of DNase X in Skeletal Muscle Addressed by Targeted Disruption of the Gene in a Mouse Model. Winnipeg: University of Manitoba. 122] and congenic wild-type C57BL/6 mice (5- to 6-week-old females; 5 mice per group) were inoculated intraperitoneally with E. chaffeensis-infected THP-1 cells (>90% cells infected; $6 \times 10^5$ cells/mouse). DNA was extracted from blood samples using a QIAamp blood kit (Qiagen), and subjected to qPCR using E. chaffeensis 16S rDNA and mouse glyceraldehyde 3-phosphate dehydrogenase (G3PDH) gene primers.

Results

Figure 2B:
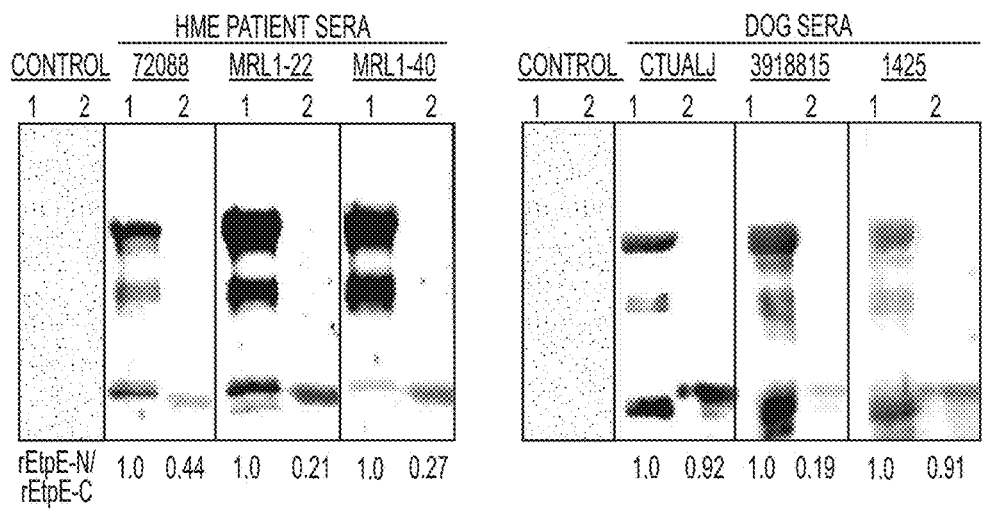

Because EtpE is highly expressed by E. chaffeensis in mammalian cells in vitro, experiments were conducted to determine whether EtpE is expressed in vivo by Western blot analysis of defined HME patient sera [Unver A, et al. (1999) J Clin Microbiol 37: 3888-3895]. Equal quantities of rEtpE-N and rEtpE-C (GelCode Blue staining shown in FIG. 2A) were used as antigens in the assay. Patient sera recognized both rEtpE-N and rEtpE-C, whereas the control serum from a healthy individual in an HME non-endemic region did not react with the recombinant proteins (FIG. 2B). Similarly, sera from dogs experimentally infected with E. chaffeensis [Huang H, et al. (2008) Infect Immun 76: 3405-3414], that were previously shown to recognize E. chaffeensis OmpA [Cheng Z, et al. (2011) Mol Microbiol 82: 1217-1234] and other E. chaffeensis lipoproteins [Huang H, et al. (2008) Infect Immun 76: 3405-3414], recognized both rEtpE-N and rEtpE-C, but the control dog serum did not (FIG. 2B). These data indicated that EtpE is expressed by E. chaffeensis in vivo during infection of its natural hosts, humans and dogs, and that an antibody (humoral) response is mounted against this protein during infection and disease.

Figure 2C:
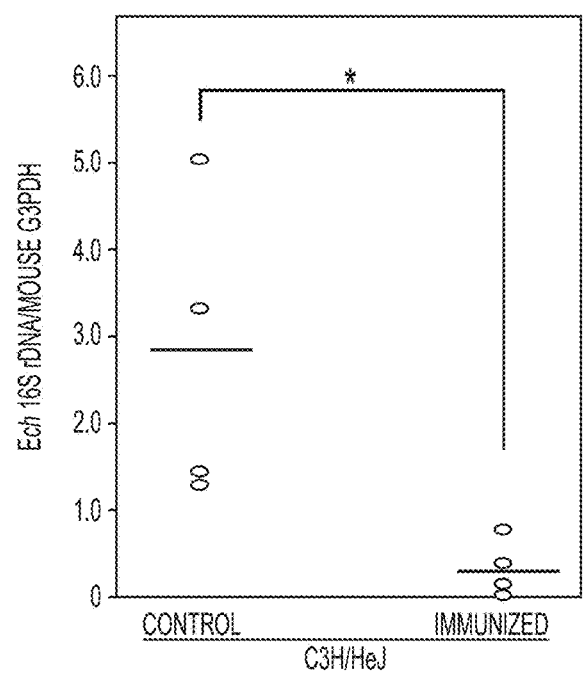

Antibodies contribute to immunity against E. chaffeensis in immunocompetent mice [Yager E, et al. (2005) Infect Immun 73: 8009-8016]. Given the facts that anti-EtpE-C neutralized E. chaffeensis binding, consequently entry and infection in vitro, EtpE was expressed by E. chaffeensis in vivo and that a humoral immune response was mounted in infected mammals, experiments were conducted to examine whether rEtpE-C immunization could confer protection in mice from E. chaffeensis challenge. C3H/HeJ strain of mice was used, since this strain was reported to serve as a useful model for studying E. chaffeensis infection [Telford S R (1996) Vet Microbiol 52: 103-112]. At 10 days after the last immunization, all mice were challenged intraperitoneally with E. chaffeensis. The E. chaffeensis load in the blood from rEtpE-C-immunized mice at 5 days post challenge was significantly lower than that of nonimmunized mice (FIG. 2C). These results indicate that rEtpE-C is a protective immunogen relevant in E. chaffeensis infection in vivo.

Example 4

Entry of rEtpE-C-Coated Beads into Macrophages is Blocked by Compounds that Block E. chaffeensis Invasion Materials and Methods Binding and internalization of latex beads. Sulfate-modified fluorescent red polystyrene beads (0.5 µm diameter; Sigma) at $3-4 \times 10^6$ beads in 200 µl of 25 mM 2-(N-morpholino)ethanesulfonic acid (MES) buffer, pH 8.0 were incubated with 1 mg of rEtpE-C or rEtpE-N proteins in 5-7 µl 7 M urea in 50 mM sodium phosphate buffer, pH 7.2 at 4° C. overnight with mixing at 20 rpm. MES buffer (150 ml) was sequentially added to the mixture every 15 min and incubated at room temperature, rotating at 20 rpm eventually diluting to around 200 times the original volume of urea buffer. rECH0825 and rGroEL were treated similarly, but without urea. The coated beads were collected by low speed centrifugation, washed twice in MES buffer and re-suspended in complete DMEM or advanced MEM media, then gently sonicated to disperse the beads. Protein coating of the beads were confirmed by dot blot assay and/or immunofluorescence labeling. Freshly prepared protein-coated or non-coated beads were added at a multiplicity of approximately 50 beads per cell for colocalization studies and 500 beads per cell for quantitation of binding and internalization studies. The beads were incubated with HEK293 or RF/6A cells for 1 h at 37° C. Unbound beads were removed by washing and cells were fixed for immunofluorescence labeling to detect the localization of DNase X or EEA1 (anti-EEA1, BD). To study the effect of MDC, genistein, or verapamil on bead internalization, RF/6A cells were incubated with these chemicals at a final concentration of 100 mM or 0.1% DMSO solvent control for 30 min, then with rEtpE-C-coated beads for 8 h at 37° C. BMDMs from wild-type mice were pre-incubated with MDC or genistein (100 mM), PI-PLC (5 U/ml) or 0.1% DMSO for 30 min and then incubated with rEtpE-C-coated or non-coated beads for 45 min at 37° C. PI-PLC-treated cells were washed prior to addition of rEtpE-C-coated beads. The cells were washed and treated with 0.25% trypsin at 37° C. for 10 min to remove surface-bound beads. The detached cells were further washed by low-speed centrifugation and later cytocentrifuged onto a glass slide and fixed with 3% PFA to observe internalized beads. To estimate the number of bound beads, a similar procedure for observing internalized beads was followed except that the beads were incubated with BMDM for 30 min at 4° C. and following incubation the cells were washed to remove loosely bound beads and directly fixed with 3% PFA without trypsin treatment. For scanning electron microscopy, rEtpE-C-coated beads were incubated with RF/6A cells for 2 h at 37° C. and processed as described previously [Thomas S, et al. (2010) PLoS One 5: e15775]. For transmission electron microscopy, coated beads were incubated with RF/6A cells for 8 h at 37° C. and processed as described previously [Rikihisa Y, et al. (1979) J Exp Med 150: 703-708]. The 3D orthogonal view of the cell to show spatial distribution of DNase X with beads was obtained by using the volume viewer function of SoftWoRx DeltaVision image acquisition software from Applied Precision.

Live-cell imaging. RF/6A cells were cultured in 35-mm glass bottom dishes (Wilco), transfected with DNase X-GFP, and incubated with rEtpE-C-coated beads at 4° C. for 1 h to facilitate bead binding, but prevent internalization. Unbound beads were washed off, cells were replenished with medium lacking phenol red, and the samples moved to a controlled environmental chamber at 37° C. with under 5% $CO^2$/95% air. Time-lapse images were acquired at an interval of 10 s for 5 to 20 min through a 60×1.42 NA oil immersion lens with an inverted Olympus IX-70 microscope, in 0.4-μm steps in the z-axis using the attached Applied Precision motorized stage (DeltaVision deconvolution microscope). All stacks of images were deconvoluted using SoftWoRx software and the time-lapse images of a single focal plane of 0.4-μm focal depth at the cell surface were exported as a video.

Results

Figure 3A:
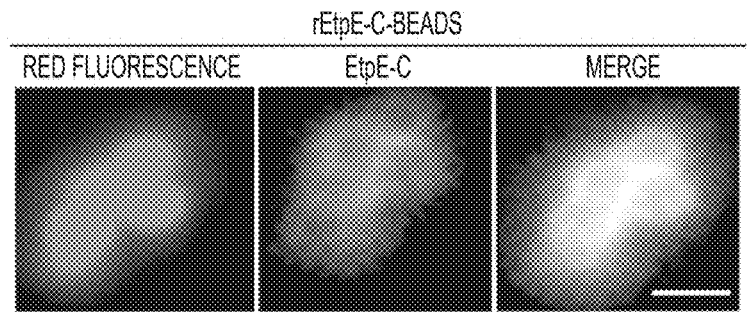
FIGS. 3A-3D show rEtpE-C-coated beads enter macrophages by a pathway similar to one that mediates *E. chaffeensis* entry.
Figure 3B:
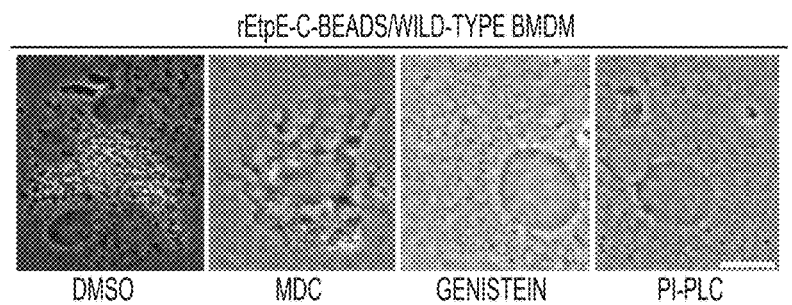
Figure 3C:
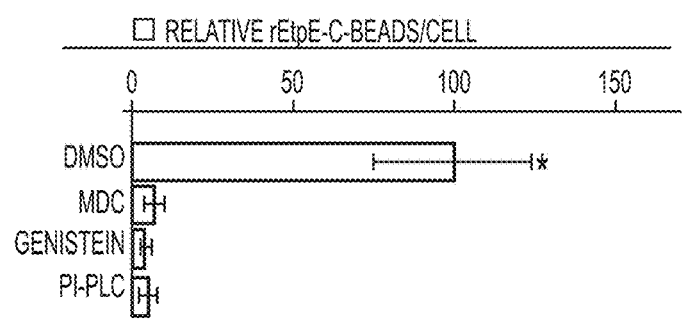
Figure 3D:
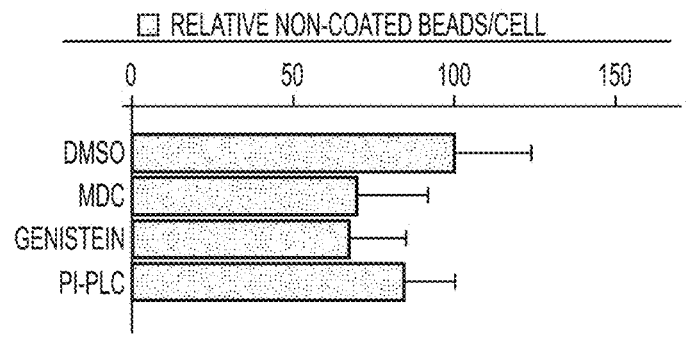

Bacterial surface exposure of EtpE-C and effectiveness of EtpE-C as the target for both in vitro and in vivo neutralization suggest that EtpE-C may mediate *E. chaffeensis* invasion. To investigate this possibility, fluorescent latex beads of average size of 0.5 μm (similar to the size of infectious DCs of *E. chaffeensis*) were coated with rEtpE-C protein. The presence of rEtpE-C on beads was confirmed by dot-blot analysis and immunofluorescence labeling with antiserum against EtpE-C (FIG. 3A). Beads were incubated with mouse bone marrow-derived macrophages (BMDMs) for 45 min followed by trypsin treatment to remove beads that were not internalized. Mouse BMDMs were used here, also to serve as the wild-type control for the later studies using BMDMs from mutant mice. rEtpE-C-coated beads entered BMDMs (FIGS. 3B and 3C). Treatment with MDC, genistein (broad-spectrum protein tyrosine kinase inhibitor), or phosphatidylinositol-specific phospholipase C (PI-PLC that removes GPI-anchored proteins from the cell surface) blocks *E. chaffeensis* entry and infection of THP-1 cells [Lin M, et al. (2002) Infect Immun 70: 889-898; Lin M, Rikihisa Y (2003) Cell Microbiol 5: 809-820]. The entry of rEtpE-C-coated beads into BMDMs was almost completely blocked by these treatments (FIGS. 3B and 3C), suggesting rEtpE-C-coated beads enter BMDMs by the same signaling pathway as *E. chaffeensis* does. The latex bead is well-known to be taken up by macrophages and has been used as a model to study phagocytosis [Werb Z, et al. (1972) J Biol Chem 247: 2439-2446]. In striking contrast, entry of non-coated beads into BMDMs was not blocked by any of these treatments (FIG. 3D).

Example 5 rEtpE-C-coated Beads Enter Non-phagocytes

Results

Figure 4A:
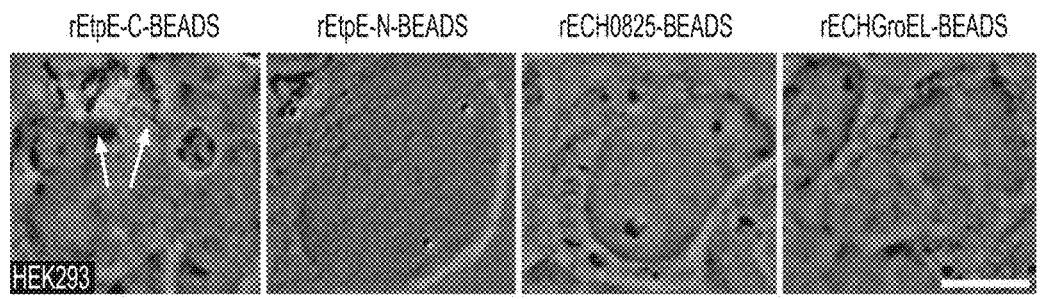
FIGS. 4A-4G show rEtpE-C-coated latex beads bind and enter non-phagocytic host cells.
Figure 4B:
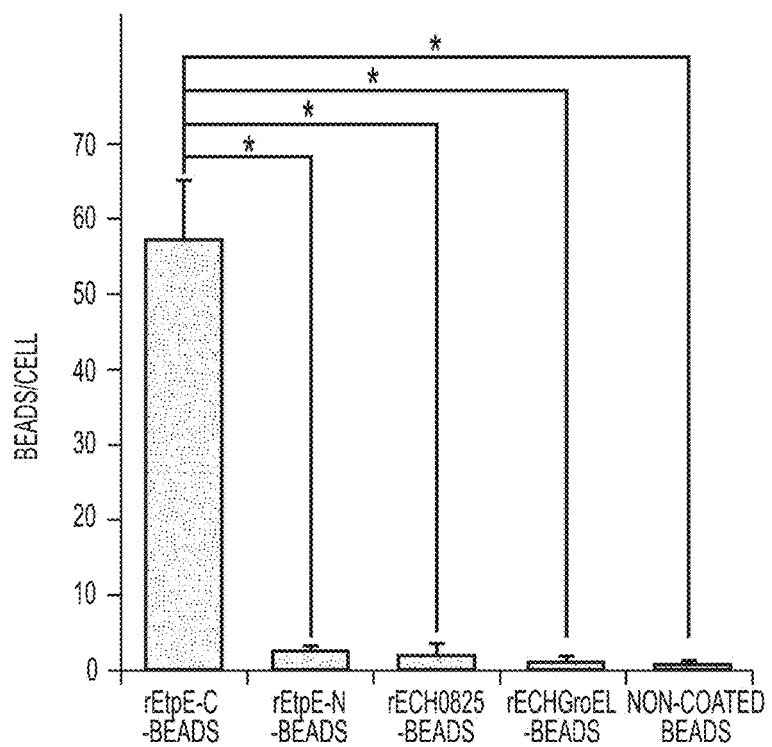
Figure 4C:
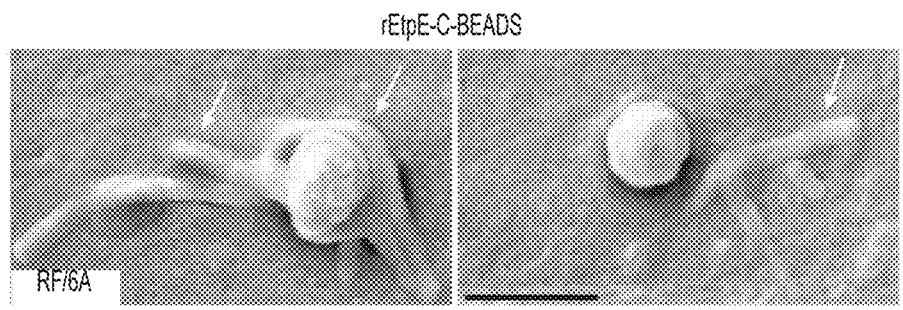
Figure 4D:
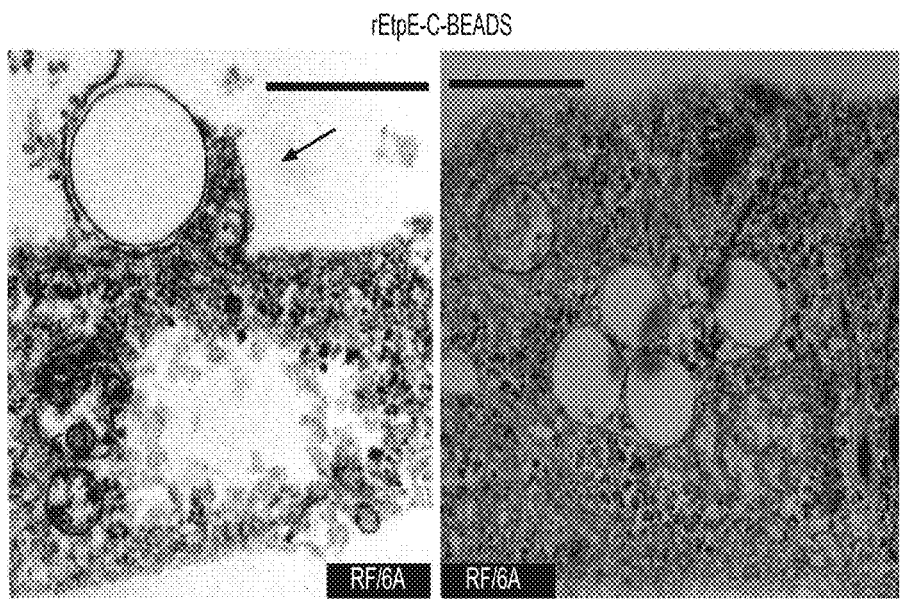
Figure 4E:
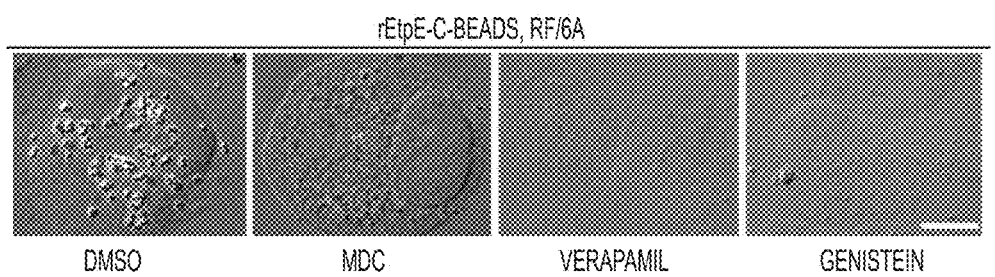
Figure 4F:
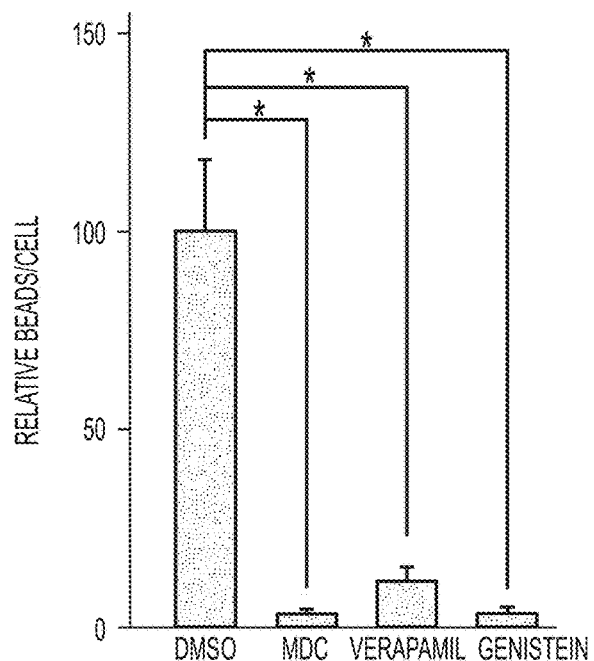
Figure 4G:
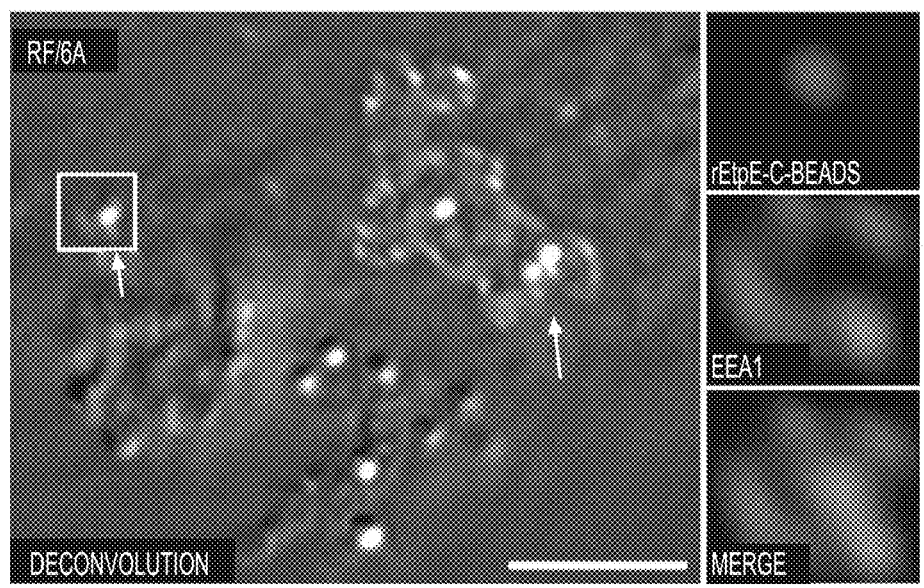
Figure 13:
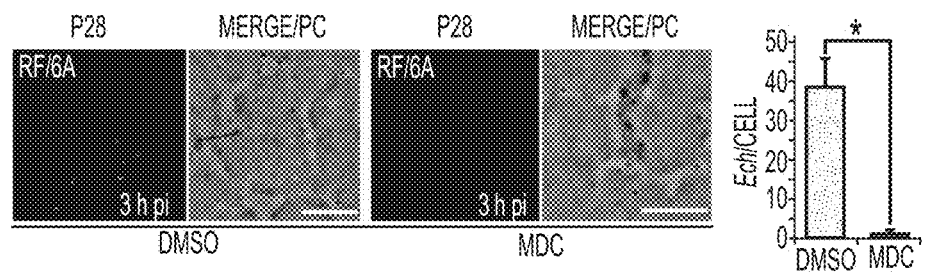
FIG. 13 shows that MDC blocks entry of *E. chaffeensis* into nonphagocytic RF/6A cells, related to FIG. 4E. Immunofluorescence labeling of *E. chaffeensis* incubated with RF/6A cells pretreated with MDC or DMSO control. At 3 h pi, cells were treated with trypsin to remove un-internalized *E. chaffeensis* and then labeled with anti-P28. Scale bar, 10 μm. Bar graph shows quantitation by scoring *E. chaffeensis* (Ech) in 100 cells (right panel). Data represent the mean and standard deviation of triplicate samples and are representative of three independent experiments. * Significantly different (P<0.05).

Non-coated beads did not bind or enter RF/6A and HEK293 non-phagocytic cells (HEK293 cell data are shown in FIG. 4B). Remarkably, rEtpE-C-coated beads did readily bind and enter non-phagocytes (HEK293 data are shown in FIGS. 4A and 4B). Beads coated with other recombinant *E. chaffeensis* proteins including rEtpE-N, rECH0825 (a type IV secretion effector protein) [Liu H, et al. (2012) Cell Microbiol 14: 1037-1050] or rECH0365 (GroEL) did not bind HEK293 cells (FIGS. 4A and 4B), indicating binding and entry of beads into nonphagocytes was due to specific coating with EtpE-C. Scanning and transmission electron microscopy revealed that rEtpE-C-coated beads bound to RF/6A cells were associated with filopodia-like membrane projections (FIGS. 4C and 4D left panel) similar to those surrounding *E. chaffeensis* bound to DH82 cells [Zhang J Z, et al. (2007) Cell Microbiol 9: 610-618]. Transmission electron microscopy of RF/6A cells incubated with rEtpE-coated beads verified that the beads were indeed internalized into RF/6A cells (FIG. 4D right panel). MDC, genistein, and verapamil (a $Ca^{2+}$ channel blocker) that block *E. chaffeensis* entry into THP-1 cells [Lin M, et al. (2002) Infect Immun 70: 889-898], also blocked *E. chaffeensis* entry into RF/6A cells (FIG. 13). Treatment with any of these compounds almost completely blocked the entry of rEtpE-coated beads into RF/6A cells (FIGS. 4E and 4F). Once internalized, *E. chaffeensis*-containing vacuoles acquire characteristics of early endosomes [Mott J, et al. (1999) Infect Immun 67: 1368-1378]. To determine whether rEtpE-C-coated beads were delivered to early endosomes, immunofluorescence labeling was used to visualize the spatial relationship of the early endosomal marker, EEA1 with the rEtpE-C-coated beads, and observed by deconvolution microscopy. Individual as well as multiple beads were seen encased by EEA1-labeled membranous compartment, suggesting that some beads were in endosomes (FIG. 4G). These results indicate that EtpE-C is an invasin, and even in the absence of any other *E. chaffeensis* factors, EtpE-C alone is sufficient to mediate the binding and entry of EtpE-C-coated beads into non-phagocytic cells.

Example 6

EtpE-C Binds DNase X

Materials and Methods

Yeast two-hybrid screening. Yeast two-hybrid screening was performed using Matchmaker Two-Hybrid System (Clontech) according to manufacturer's instructions. The bait plasmid pGBKT7-EtpE-C was constructed by the fusion of EtpE-C with the GAL4 DNA-binding domain in pGBKT7 (Clontech) by PCR. EtpE-C coding sequence was amplified using the forward primer 5'-AATCCATGGA ATT-GTTGTCA TTAGTTGGTG GGCATCG-3' (SEQ ID NO:12) and reverse primer 5'-TCGACGGATC CAATC-CCCTT CCAGCATTAA TTTTATCAAA GG-3' (SEQ ID NO:13), and the product was ligated into pGBKT7. pGBKT7-EtpE-C was transformed into *Saccharomyces cerevisiae* strain AH109 and selected by the ability to grow on SD agar plates lacking tryptophan. The expression of bait protein EtpE-C in yeast was examined by Western blotting. The human bone marrow MATCHMAKER cDNA library (Clontech) that was fused with GAL4-activating domain in pGADT7 was transformed in *S. cerevisiae* strain Y187 (Clontech). Library clones expressing interacting prey proteins were screened with yeast mating. Positive clones were selected by their ability to grow on SD quadruple drop-out (SD/QDO) plates lacking adenine, histidine, leucine, and tryptophan, and verified on SD/QDO plates containing X-gal. Positive clones were then isolated, and the prey plasmids were purified and sequenced after they were transformed into *E. coli* TOP10F9 competent cells (Invitrogen). The interaction was confirmed by re-shuttling the purified prey plasmid into *S. cerevisiae* AH109 transformed with bait plasmid and by nutritional selection in SD/QDO plates.

Far-Western blotting, protein affinity pull-down and coimmunoprecipitation. Far-Western blotting was performed using 5 μg of rEtpE-C and rECH0825 that were separated by SDS-PAGE, transferred to a nitrocellulose membrane and renatured with serial guanidinium-HCl treatment followed by incubation with THP-1 cell lysate in NP-40 lysis buffer (150 mM NaCl, 50 mM Tris-HCl pH 7.4, 1% w/v NP-40, supplemented with 1% protease inhibitor cocktail set III [Calbiochem]) as described [Bao W, et al. (2009) J Bacteriol 191: 278-286]. After stringent washing, the membrane was incubated with anti-DNase X and peroxidase-conjugated goat anti-mouse antibodies (KPL). The membrane was stripped with Restore Western Blot Stripping Buffer (Thermo scientific) and re-probed with peroxidase-conjugated anti-histidine antibody (Sigma). For protein pull-down, His-tagged rEtpE-C was bound to and renatured on the Ni-affinity matrix (Promega). THP-1 cell lysate in NP-40 lysis buffer was applied to the matrix and incubated for 8 h at 4° C. After washing off the unbound or non-specifically bound proteins from the matrix, rEtpE-C and bound protein complex were eluted with 250 mM imidazole. The eluate and the post-elution Ni-matrix were resuspended in 26 SDS-sample buffer and subjected to Western blotting with anti-DNase X antibody. For co-immunoprecipitation assay, THP-1 cells were incubated with *E. chaffeensis* for 30 min and lysed in NP-40 lysis buffer. The lysate was immunoprecipitated with anti-EtpEC (2 μg)-bound protein A agarose or control mouse IgG (2 μg)-bound agarose beads. The precipitate was re-suspended in 2×SDS-sample buffer and subjected to Western blotting with anti-DNase X antibody.

Results

Since EtpE-C could mediate binding and entry of EtpE-C-coated beads, Experiments were conducted to search for the potential host-cell receptor for EtpE-C. EtpE-C was cloned into the yeast two-hybrid bait vector and a human bone marrow cDNA prey library was screened to identify interacting proteins. Of the 5 clones detected and sequenced, all of them encoded a protein, deoxyribonuclease 1-like 1 (DNase 1L1, DN1L1, or DNase X on chromosome Xq28, GenBank accession no: X90392, 302 residues). One of the clones contained an additional plasmid encoding S-adenosyl methionine-dependent methyltransferase but the coding sequence was out-of-frame; this prey construct alone did not support yeast growth when co-transformed with bait vector to test their interaction. All sequence hits corresponded to the C-terminal fragment of DNase X (residues 105-302). DNase X, one of the human DNase I-family endonucleases, is expressed on the cell surface as a GPI-anchored protein and also localized at early endocytic vesicles, endoplasmic reticulum, and Golgi [Shiokawa D, et al. (2001) Biochemistry 40: 143-152; Shiokawa D, et al. (2007) J Biol Chem 282:17132-17140].

To confirm EtpE-C binding to the native human DNase X, far-Western blot analysis was performed. DNase X from the THP-1 cell lysate bound to renatured rEtpE-C on a nitrocellulose membrane, whereas DNase X did not bind the control rECH0825 (FIG. 5A). Next, a protein pull-down assay was used wherein THP-1 cell lysate was applied to rEtpE-C bound to and renatured on a Ni-affinity matrix. Western blotting showed that native DNase X from the lysate bound to rEtpE-C, but not to the control rECH0825 (FIG. 5B). In addition, co-immunoprecipitation showed that anti-EtpE-C, but not the control mouse IgG pulled down native DNase X from the lysate of THP-1 cells incubated with *E. chaffeensis* for 30 min (FIG. 5C). Taken together, these results indicate that EtpE-C can bind to DNase X.

RF/6A or HEK293 cells incubated with rEtpE-C-coated beads were fixed, and without membrane permeabilization, immunofluorescence labeled cell surface-exposed DNase X was conducted. DNase X localized to the areas on the surface of cells where rEtpE-C-coated beads were present (RF/6A cell image shown in FIG. 5D). Timelapse live-cell image analysis of rEtpE-C-coated beads bound to RF/6A cells ectopically expressing DNase X-GFP at 4° C. showed that, upon warming up to 37° C., the initially separated DNase X-GFP signal and beads became closer and overlapped within 5 min (FIG. 5E). The fluorescence intensity profile analysis of red (rEtpE-C-coated beads) and green (DNase X-GFP) signal along the length of the line also revealed that the signals separated at initial time points converged in a few min after warming-up (FIG. 5F).

Example 7

Binding and Internalization of rEtpE-C-coated Beads is Dependent on DNase X

Results

Figure 6D:
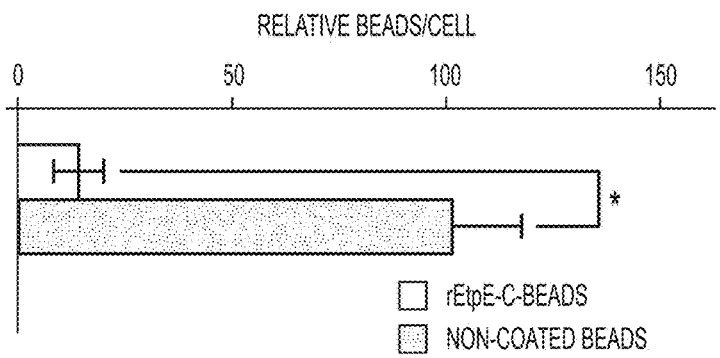
Figure 14A:
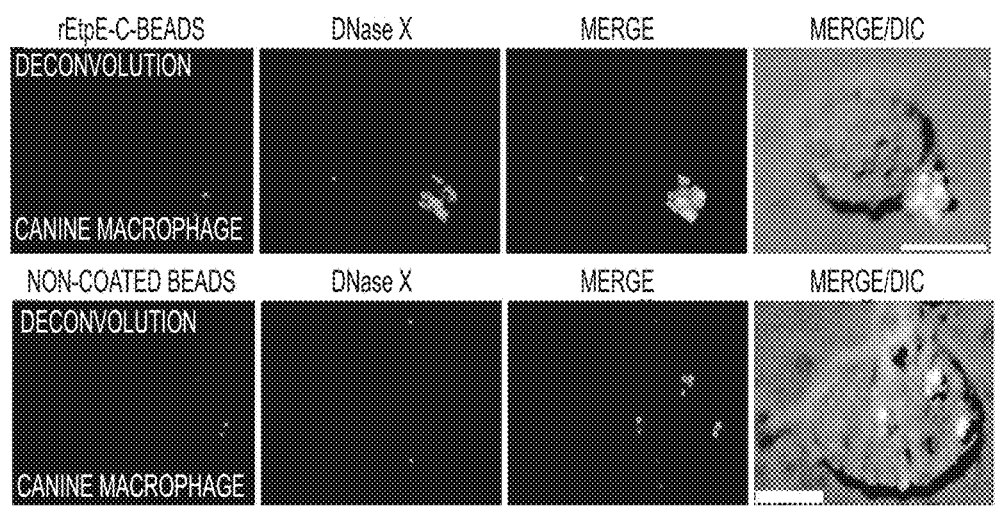
FIGS. 14A-14B show that rEtpE-C-coated beads recruit DNase X to the areas of binding, related to FIG. 6. rEtpE-C-coated or noncoated latex beads were incubated with canine primary macrophages derived from peripheral blood monocytes (A) or DH82 cells (B) at 37° C. for 30 min, and labeled with anti-DNase X without permeabilization. rEtpE-C-coated beads recruited surface exposed DNase X to their sites of binding and clustered, whereas non-coated beads did not colocalize with DNase X on the cell surface. A single z-plane, of an optical section thickness of 0.4-µm, at cell surface by deconvolution microscopy was shown. Scale bar, 5 µm.
Figure 14B:
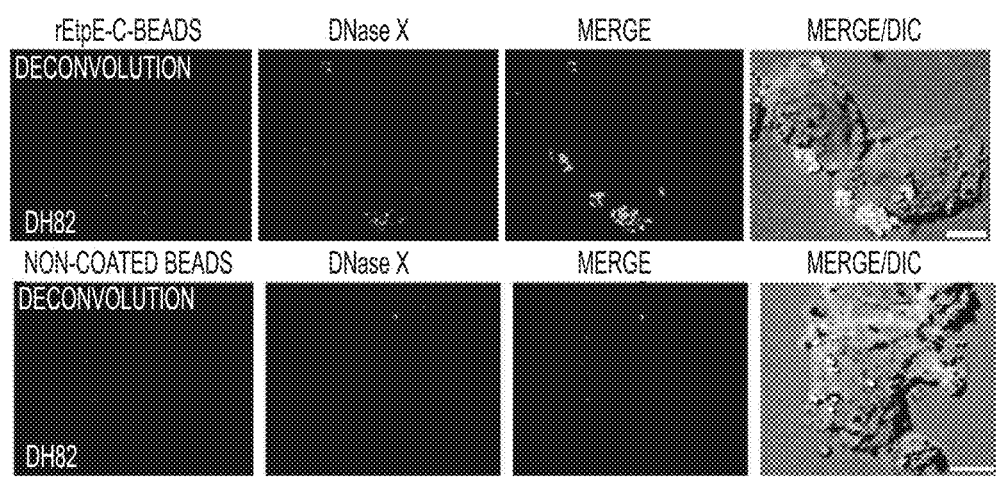
Figure 15A:
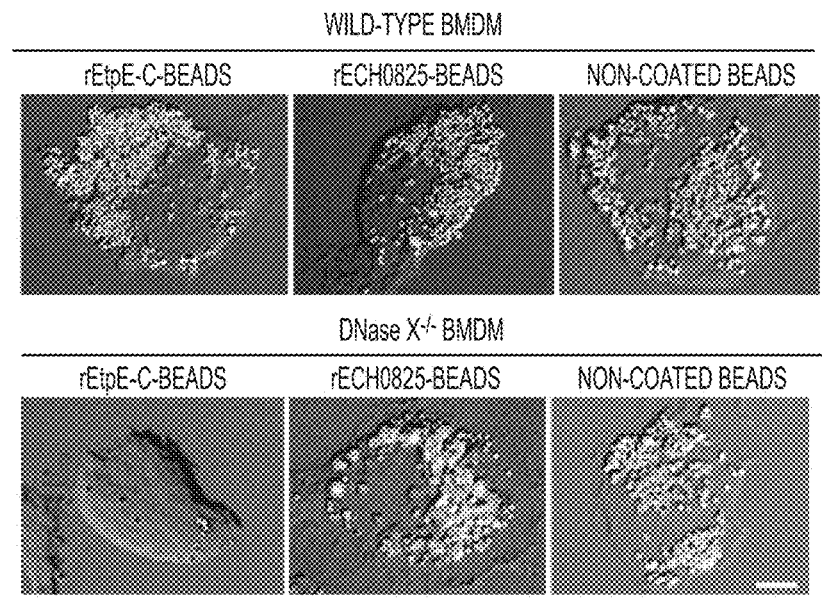
FIGS. 15A-15B show that binding of rEtpE-C-coated beads is dependent on DNase X, related to FIGS. 6C and D.
Figure 15B:
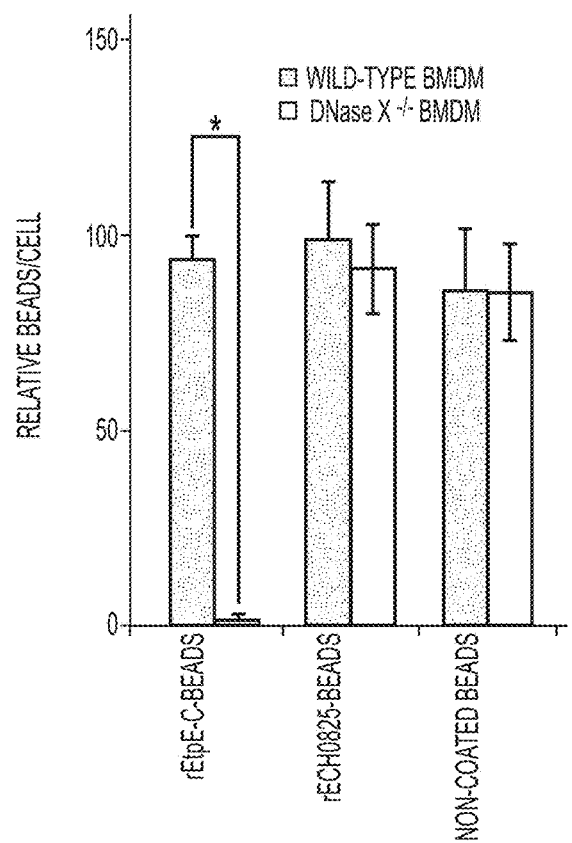

Since DNase X localized to EtpE-C-coated beads in nonphagocytes, this phenomenon was next examined in phagocytes. Human primary macrophages derived from peripheral blood monocytes were incubated with rEtpE-C-coated or non-coated beads, cell surface exposed DNase X was immunofluorescence-labeled without permeabilization and the distribution of beads and DNase X was examined by deconvolution microscopy. Surface DNase X was seen clustered with rEtpE-C-coated beads; whereas both surface DNase X and beads were randomly dispersed with non-coated beads (image in a single z-plane shown in FIG. 6A). Orthogonal views of the cell from the reconstructed 3D view of serial z-stack images unequivocally demonstrated colocalization of DNase X with rEtpE-C-coated beads (FIG. 6B left panel), whereas DNase X did not colocalize with non-coated beads (FIG. 6B right panel). The intensity profile analysis of green (DNase X) and red (beads) signals of a single optical section showed that DNase X coincided with rEtpE-C-coated beads, but not with noncoated beads (FIG. 6B right panels). Similar results were observed with canine primary macrophages derived from peripheral blood monocytes and DH82 cells (FIG. 14). These results indicate DNase X localizes to rEtpE-C-coated beads in primary human and canine macrophages, the pathogen's in vivo target cells.

rEtpE-C-coated beads entered wild-type mouse BMDMs as shown in FIGS. 3B and 3C. Therefore, experiments were conducted to determine whether rEtpE-C-coated beads can enter BMDMs from congenic DNase $X^{-/-}$ mice. Beads were incubated with BMDMs from DNase $X^{-/-}$ mice for 45 min followed by trypsin treatment to remove beads that were not internalized. Results showed rEtpE-C-coated beads did not enter DNase $X^{-/-}$ BMDMs (FIGS. 6C and 6D). In striking contrast, non-coated beads freely entered DNase $X^{-/-}$ BMDMs (FIGS. 6C and 6D). This lack of entry of rEtpE-C-coated beads into DNase $X^{-/-}$ BMDM, but not into the wild-type BMDM, was a direct consequence of its failure to bind DNase $X^{-/-}$ BMDM (FIG. 15). This phenomenon was specific to rEtpE-C-coated beads, because neither the non-coated beads nor the rECH0825-coated beads showed any defect in binding DNase $X^{-/-}$ BMDMs (FIG. 15). Taken together, these results indicate that rEtpE-C coating dictates the latex bead binding and entry via DNase X-dependent pathway.

Example 8

DNase X Mediates *E. chaffeensis* Binding, Entry, and Infection

Materials and Methods

In vitro neutralization and RNA interference. *E. chaffeensis* preincubated with 25 μg/ml of mouse anti-rEtpEC, rabbit anti-rEtpE-N, or preimmune mouse or rabbit sera for 1 h at 4° C. were used to infect THP-1, RF/6A, or DH82 cells. Alternatively, *E. chaffeensis* was added to DH82 cells preincubated with 10 μg/ml of monoclonal anti-DNase X or control mouse monoclonal antibody for 30 min at 25° C. in serum-free DMEM. Binding, internalization, and infection were determined at 30 min, 2 h and 48 h pi, respectively. HEK293 cells in 24-well plates were transfected with 50 nM DNase X siRNA (Santa Cruz Biotechnology) or scrambled control siRNA using Lipofectamine 2000 (Invitrogen). A second transfection with 50 nM of DNase X and scrambled siRNAs was performed 30 h after the first transfection. An aliquot of cells were harvested at 24 h after the second transfection to determine the protein amount of DNase X by Western blotting and densitometry analysis with anti-DNase X and rabbit anti-actin (Sigma). The other aliquot of cells were incubated with *E. chaffeensis* and incubated for an additional 48 h to evaluate infection. Infection was determined by qPCR of *E. chaffeensis* 16S rRNA gene relative to host cell G3PDH gene [Cheng Z, et al. (2011) Mol Microbiol 82: 1217-1234].

Results

Figures 7A, 7B:
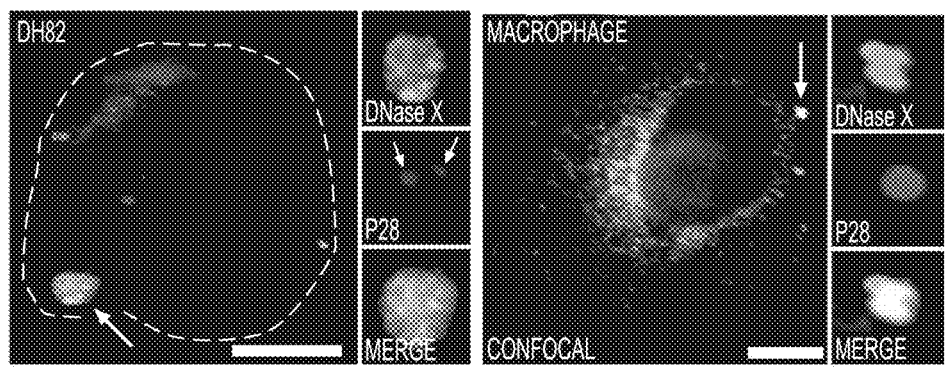
Figures 7C, 7D, 7E:
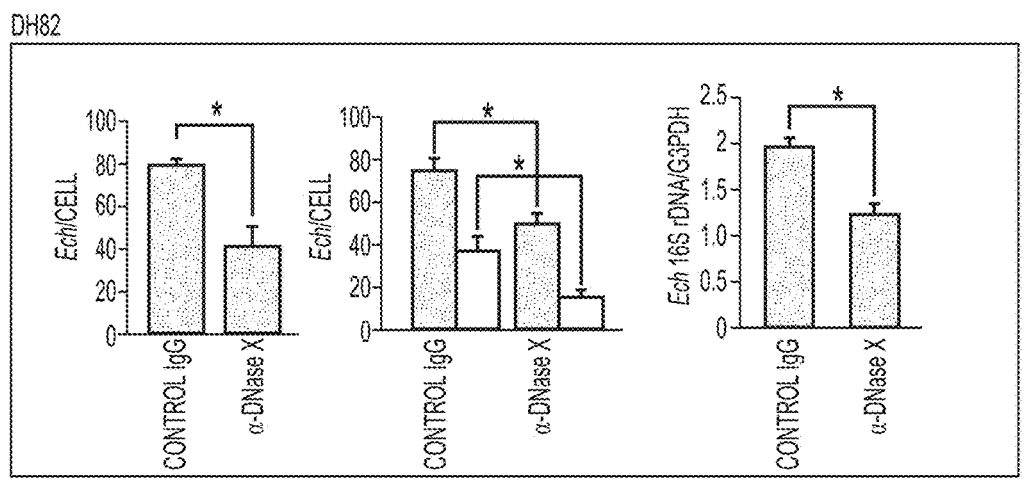
Figure 7J:
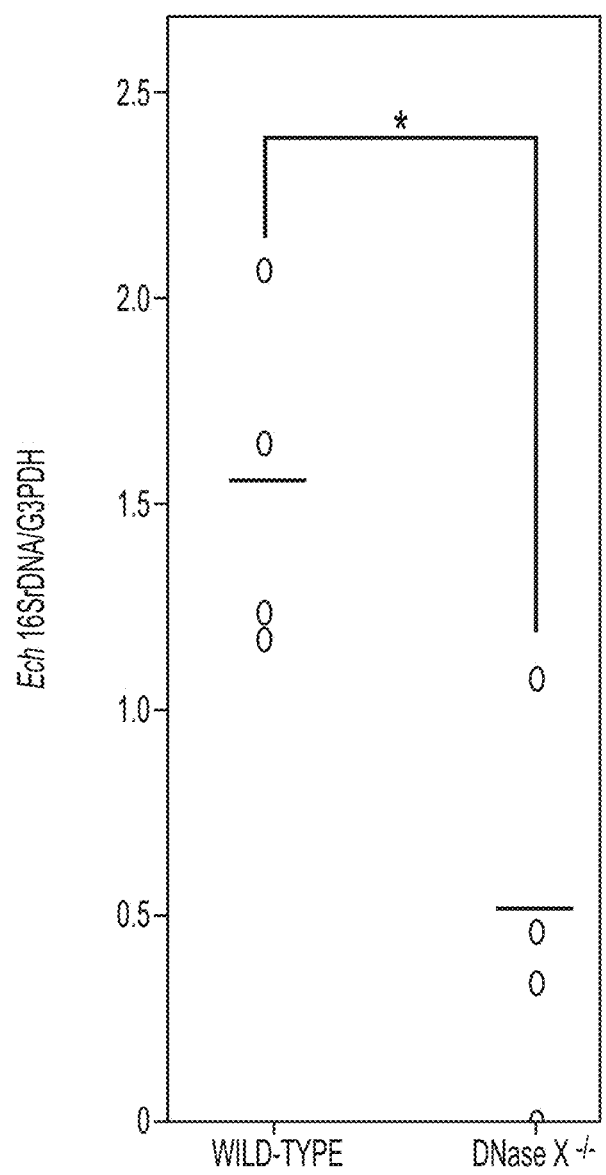
Figure 8:
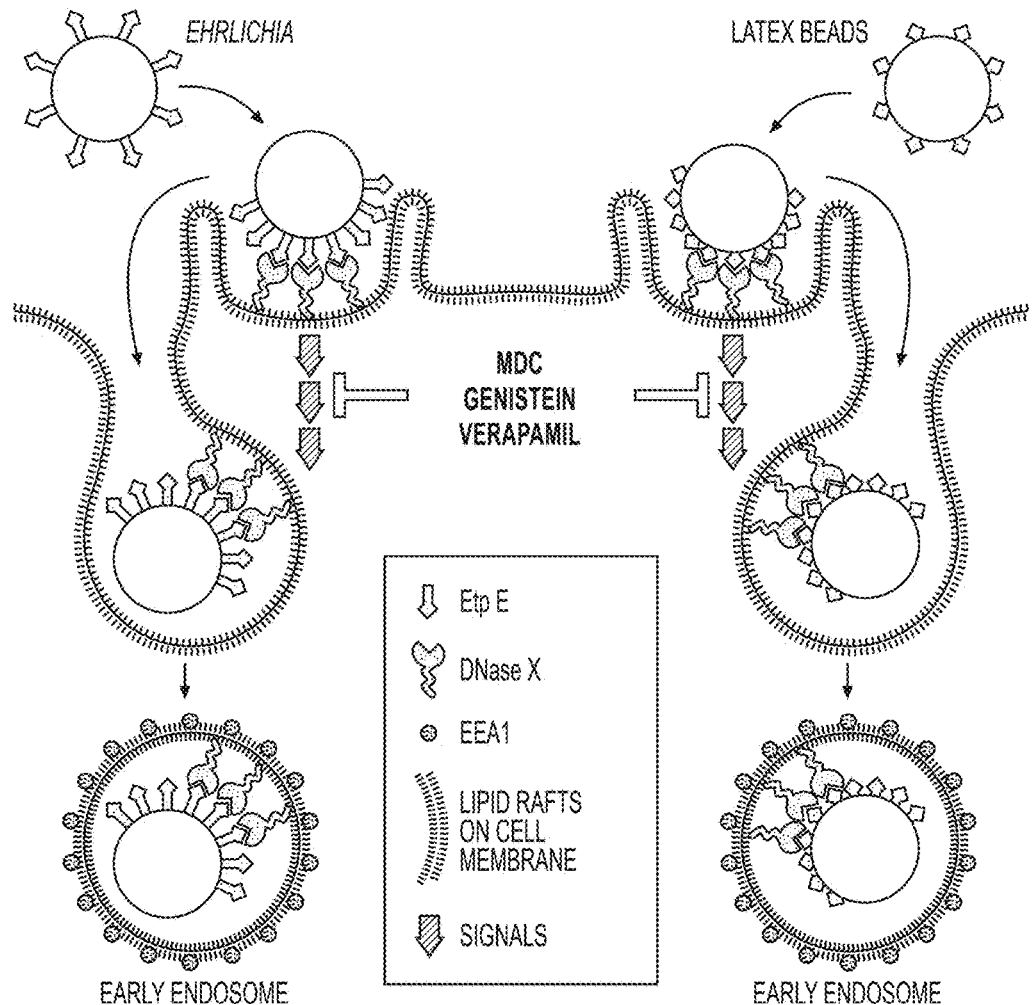
FIG. 8 is a schematic representation of *E. chaffeensis* binding and entry into mammalian cells. DNase X is enriched in the lipid raft domains of the cell membrane. Extracellular *E. chaffeensis* uses its surface protein EtpE C-terminal region to make initial contacts with cell surface DNase X that results in further lateral redistribution and local clustering of DNaseX at the sites of bacterial binding. This binding elicits signals that are relayed down-stream and culminated in host cytoskeletal remodeling, filopodial induction and engulfment of the bound bacteria into an early endosome into the host cell. This receptor-mediated endocytosis can be specifically disrupted by genistein, verapamil or MDC. Latex beads coated with rEtpE-C also bind to cell surface DNase X and follows a similar pattern of entry like that of *E. chaffeensis*.

Since DNase X was localized to EtpE-C-coated bead entry foci, experiments were conducted to determine whether DNase X localizes to the *E. chaffeensis* entry foci as well. Double immunofluorescence labeling of non-permeabilized DH82 cells and primary human macrophages derived from human peripheral blood monocytes showed surface DNase X colocalization with the bound *E. chaffeensis* (FIGS. 7A and 7B). DNase X also localized to the areas of *E. chaffeensis* binding on THP-1 cells. When DH82 cells were pre-incubated with monoclonal anti-DNase X IgG to block the surface-exposed DNase X, *E. chaffeensis* binding, entry, and overall infection were significantly reduced compared with the control mouse IgG-treated DH82 cells (FIGS. 7C-7E). Next, a small interfering RNA (siRNA) against DNase X was used to reduce the expression of endogenous DNase X in HEK293 cells (FIG. 7F). Suppression of DNase X expression significantly reduced *E. chaffeensis* infection in HEK293 cells (FIG. 7G). Moreover, *E. chaffeensis* binding and entry were reduced by 60% in DNase X BMDMs compared to the wild-type BMDMs (FIG. 7H). *E. chaffeensis* load at 56 h pi was significantly lower in DNase X BMDMs compared to the wild-type BMDMs (FIG. 7I). These results demonstrated that effective *E. chaffeensis* binding, entry, and infection depended on DNase X. Importantly, *E. chaffeensis* load in peripheral blood at 5 days pi in DNase $X^{-/-}$ mice was significantly lower than in wild-type mice (FIG. 7J), indicating that effective in vivo infection of *E. chaffeensis* also requires involvement of DNase X.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject with Ehrlichiosis, the method comprising: diagnosing Ehrlichiosis in the subject, wherein said diagnosing comprises assaying a biological sample from the subject for the presence of an antibody that specifically binds a polypeptide comprising SEQ ID NO:7, SEQ ID NO:8, SEQ ID NO:9, or a conservative variant thereof having at least 70% identity to SEQ ID NO:7, SEQ ID NO:8, or SEQ ID NO:9, wherein the presence of the antibody is an indication that the subject has been infected with an *Ehrlichia* sp., and treating the subject diagnosed with Ehrlichiosis accordingly.

2. The method of claim 1, wherein the presence of the antibody is an indication that the subject has been infected with an *Ehrlichia sp.* selected from the group consisting of *Ehrlichia chaffeensis, Ehrlichia canis,* and *Ehrlichia ruminantium*.

3. The method of claim 1, comprising treating the subject with an effective amount and duration of doxycycline.

4. The method of claim 1, wherein the biological sample is a blood, serum, or plasma sample.

* * * * *

SEQUENCE LISTING

```
<160> NUMBER OF SEQ ID NOS: 13

<210> SEQ ID NO 1
<211> LENGTH: 1963
<212> TYPE: PRT
<213> ORGANISM: Ehrlichia chaffeensis

<400> SEQUENCE: 1

Met Lys Val Trp Cys Tyr Lys Asn Ile Gly Leu Tyr Leu Ile Val Leu
1               5                   10                  15

Leu Ser Phe Val Tyr Pro Arg Ala Leu Leu His Ala Lys Ile Asn Ile
            20                  25                  30

His Val Leu Arg Asp Tyr Ala Asn Val His Tyr Asn Thr Tyr Tyr Gly
        35                  40                  45

Leu His Phe Asp Asn Tyr Tyr Lys Pro Val Asp Asn Thr Glu Gly Asn
    50                  55                  60

Leu Asp Ser Val Met Ile Arg Phe Ala Ser His Asp Ser Tyr Arg Tyr
65                  70                  75                  80

Met Ser Phe Met Gln Tyr Val Lys Gly Gln Tyr Gln Asp Val Glu Asn
                85                  90                  95

Leu Asn Val Ser Gly Leu Asp Ile Pro Phe Asn Arg Glu Asp Arg Thr
            100                 105                 110

Phe Asp Asp His Asp Val Met Phe Met Gln Leu Ser Ser Tyr Trp Gly
        115                 120                 125

Lys Val Thr Phe His Ser Leu Pro Ile Gly Gly Cys Lys Val Leu Tyr
    130                 135                 140

Ala Gly Ser Ile Ile Tyr Asp Pro Val Ser Ala Ile Ala Phe Leu Glu
145                 150                 155                 160

Asn Glu Asn Ala Ser Ser Lys Val Cys Ile Cys Phe Val Gly Lys Cys
                165                 170                 175
```

```
Asn Val Lys Pro Glu Arg Asn Ser Cys Asp Lys Lys Ser Ile Arg Cys
            180                 185                 190

Lys Lys Val Thr Val Ala Ile Asn Pro Pro Phe Cys Ser Ile Leu
        195                 200                 205

Asp Ala Ser Ser Ile Val Ser Ile Thr Pro Leu Arg Phe Ser Gln Gln
210                 215                 220

Thr Phe Phe Arg Pro Gly Val Arg Ile His Ile Tyr Ser Gly Ser Gly
225                 230                 235                 240

Asn Pro Tyr Thr Lys Glu Leu Tyr Val Lys Ser His Lys Ile Gly Asp
            245                 250                 255

Lys Thr Ser Tyr Asn Ile Ser His Ala Gly Ile Pro Tyr Glu Phe Gln
            260                 265                 270

Val Tyr Lys Ala Gly Tyr Asp Thr Val Cys Ala Glu Tyr Ser Asn Asn
        275                 280                 285

Gly Glu Lys Gly Lys Lys Val Cys Val Pro Ser Pro Gly Leu Met Arg
        290                 295                 300

Pro Lys Val Thr Ser Asn Ala Asn Gly Val Asn Ile Gln Tyr Gln Asp
305                 310                 315                 320

Cys Gln Gly Leu Ser Ser Cys Ser Val Asp Met Leu Pro Gly Thr Gln
                325                 330                 335

Asp Leu Asp Met Tyr Phe Ser Val Ile Lys Pro Lys Ile Asp Phe Asn
            340                 345                 350

Asn Tyr Thr Leu Leu Ser Arg Tyr Glu Cys Glu Asp Gly Lys Ile Val
            355                 360                 365

Glu Asn Glu Asn Gln Cys Val Asn Gly Ile Gly Gln Arg Leu Gly Tyr
        370                 375                 380

Val His Asp Asn Asn Ser Asn Val Thr Cys Val Val Asp Met Pro Phe
385                 390                 395                 400

Val Pro Met Lys Tyr Ser Ile Lys Lys Asn His Arg Asp Leu Trp Leu
                405                 410                 415

Ser Met His Asp Lys Met Leu Leu Gly Tyr Gly Val Val Gly Lys
            420                 425                 430

Thr Asp Thr Gly Lys Asp Val Glu Arg Tyr Val Gln Cys Asp Gln Lys
        435                 440                 445

Phe Ala Ile Asp Ile Lys Ser Met Thr Gln Glu Gln Leu Asn Lys Ile
450                 455                 460

Thr Arg Ile Arg Gln Asp Ala Phe Phe Asp Ile Gly His Tyr Asn
465                 470                 475                 480

Pro Lys Asn Ala Pro Cys Gln Asp Ser Met Leu Tyr Arg Tyr Glu Asn
            485                 490                 495

Asn Arg Leu Tyr Glu Lys Gly Gly Gln Val Ser Cys Lys Asn Met Val
        500                 505                 510

Glu Leu Asp Tyr Gly Thr Lys Lys Ile Lys Gly Cys Ser Ser Leu Tyr
        515                 520                 525

Met Ser Asp Asp Asp Phe Thr Tyr Phe Phe His Glu Asn Asp Glu Leu
            530                 535                 540

Glu Lys Ile Val Pro Leu Asn Pro Ile Leu Gln Gly Met Cys Val Ser
545                 550                 555                 560

Asn Phe Pro Ser Tyr Glu Tyr Lys Lys Arg Val Leu Val Arg Lys Ile
                565                 570                 575

Leu Pro Asp Ser Tyr Lys Leu Gly Ile Asp Gln Lys Asn Thr Glu Cys
            580                 585                 590
```

```
Asp Phe Leu Lys Ile Glu Ala Trp Gly Gly Ala Ser Gly Ile Ser
            595                 600                 605

Arg Ser Gly Arg Ser Gly Lys Ala Gly Asn Tyr Val Met Gly Leu Leu
        610                 615                 620

Arg Phe Asp Lys Asn Val Val Asn Lys Lys Leu Ile Ile Asp Ile Gly
625                 630                 635                 640

Asp Gly Gly Lys Gly Ala Asn Ser Leu Ser Asn Ser Gly Gly Asp Thr
                645                 650                 655

Thr Val Lys Leu Cys Asp Asp Asp Lys Asn Cys Leu Val Lys Ile
            660                 665                 670

Ile Ala His Gly Gly Asp Glu Gly Gly Asn Tyr Leu Gln Asp Ser Ser
        675                 680                 685

Glu Gly Ile Asp Asn Leu Val His Tyr Arg Phe Ala Pro Gly Leu Gln
        690                 695                 700

Asn Ser Gly Glu Ser Glu Ile Leu Val Pro Tyr Gln Ser Pro Asp Met
705                 710                 715                 720

Pro Tyr Gly Lys Leu Arg Lys Gly Asp Lys Glu Cys Leu Cys Asp Ser
                725                 730                 735

Asn Ile Leu Glu Lys Asn Ser Asn Lys Tyr Trp Gly Ala Gly Gly Cys
            740                 745                 750

Ser Ser Val Tyr Asn Cys Ala Gln Glu Gly Ala Asn Gly Met Val Arg
        755                 760                 765

Ile Thr Cys Glu Lys Trp Ser Gly Asn Val Gly Lys Ile Ser Leu Ile
        770                 775                 780

Asp Glu Asn Ala Cys Ser Asp Phe Leu Val Thr Leu Ile Glu Lys Met
785                 790                 795                 800

His Lys Ser Thr Ser Gly Ile Pro Asn Val Val Lys Glu Phe Leu Gln
                805                 810                 815

Lys Ile Ser Lys Val Ser Phe Cys Arg Gln Ser Lys Ser Phe Pro Asn
            820                 825                 830

Leu Ile Ser Ser Met Ser Lys Tyr Phe Ile Ala Ile Asp Lys Ile Leu
        835                 840                 845

Val Gly Gly Asp Ile Leu Gly His Asn Leu Ser Gly Leu Arg Lys Glu
850                 855                 860

Leu Phe Thr Glu Leu Asn Asn Thr Glu Val Lys Ala Met Leu Ala Lys
865                 870                 875                 880

Leu Gly Ile Asn Glu Ser Pro Glu Thr Leu Leu Leu Tyr Leu Asp Val
                885                 890                 895

Leu Asn Phe Asn Phe Gly Val Asn Ile Ser Asn Pro Pro Ser Gly Leu
            900                 905                 910

Leu Asn Tyr Tyr Val Ser Asp Asn Glu Phe Asp Tyr Asp Leu Ser Lys
        915                 920                 925

His Asp Glu Asp Tyr Asp Lys Leu Ser Asp Asn Glu Ala Met Met Phe
        930                 935                 940

Asn Val Thr Thr Glu Lys Pro Glu Gln Trp Phe Ser Val Glu Leu Lys
945                 950                 955                 960

Asp Pro Glu Phe Val Arg Arg Tyr Arg Asn Phe Ile Asn Met Ile His
                965                 970                 975

Arg Ser Val Ile Thr Asp Glu Gly His Lys Lys Asn Asn Ile Val
            980                 985                 990

Val Ser Trp Met Tyr Thr Phe Phe  Lys Ser Asp Arg Gln  Leu Phe Glu
        995                 1000                1005

Leu Tyr  Ala Ala Pro Phe Val  Glu Leu Met Leu Gly  Met Asp Leu
```

```
            1010                1015                1020

Asn Lys Phe Met Lys Trp Gly Asn Cys Ser Asp Thr His Ile Arg
            1025                1030                1035

Leu Phe Glu Ser Ile Gly Lys Tyr Ser Glu Arg Leu Pro Ser Gln
            1040                1045                1050

Ile Gln Asp Phe Ile Lys Lys Ile Ala Thr Gly Asp Phe Cys Asn
            1055                1060                1065

Thr Phe Ser Lys Met Glu Leu Leu Asn Ser Tyr Gly Val Glu Leu
            1070                1075                1080

Ser Asn Tyr Ala Ile Asp Cys Ala Leu Lys Asn Thr Asp Lys Arg
            1085                1090                1095

Cys Leu Glu Ser Lys Trp Arg Ser Ser Leu Gly Ser Met Ala Lys
            1100                1105                1110

Lys Leu Gln Asp Ala Val Asp Leu Asn Tyr Glu Val Phe Thr Asp
            1115                1120                1125

Ile Gly Ile Ala Ser Asn Arg Lys Glu Ile Ala Leu Leu Ile Asp
            1130                1135                1140

Ala Val Met Leu Asn Tyr Val Met Ser Asp Leu Asn Val Gly Asn
            1145                1150                1155

Ser Asp Ile Thr Ser Thr Leu Ser Leu Leu Asp Pro Ile Ser Ser
            1160                1165                1170

Gln Ala Leu Asp Asn Phe Pro Tyr Asp Thr Ile Val Glu Leu Arg
            1175                1180                1185

Gln Asp Ala Ser Asn Met Lys Tyr Gly Lys Tyr Gly Asp His Arg
            1190                1195                1200

Ala Asn Ile Val Thr Leu Trp Ser Tyr Met Ala Tyr Asn Ser Phe
            1205                1210                1215

Glu Trp Asn Ile Glu Asp Phe Lys Ser Phe Val Lys Leu Leu Leu
            1220                1225                1230

Ala Glu Asp Leu Thr Ser Val Lys Ile Arg Lys Cys Asn Asp Asn
            1235                1240                1245

Leu Arg Tyr Leu Phe Asp Lys Leu Asn Lys Tyr Lys Ser Lys Leu
            1250                1255                1260

Pro Ala Val Leu Gln Asp Phe Leu Asp Lys Ile Ser Lys Glu Ser
            1265                1270                1275

Val Cys Lys Lys Ile Ser Arg Phe Ala Ala Leu Glu Thr Ser Leu
            1280                1285                1290

Val Lys Tyr Glu Glu Asn Leu Leu Asn Glu Leu Arg Gly Gly Asn
            1295                1300                1305

Leu Phe Tyr Phe Ser Ser Leu Tyr Asp Leu Asn Tyr Ala His Arg
            1310                1315                1320

Gly Lys Leu Ser Asn Ile Glu Lys Val Tyr Ser His Ala Ala Asn
            1325                1330                1335

Ile Trp Ser Asp Val Gly Glu Leu Ser Ser Asn Ile Thr Asn Leu
            1340                1345                1350

Leu Asn Asn Pro Glu Ile Tyr Lys Ile Phe Thr Asp Ala Gly Ile
            1355                1360                1365

Thr Ser Ser Lys Glu Glu Ile Ser Leu Ala Phe Asp Ala Val Ile
            1370                1375                1380

Phe Asn Ser Leu Val Ser Glu Ile Lys Ile Asp Gln Lys Lys Leu
            1385                1390                1395

Lys Asn Leu Leu Leu Leu Ile Tyr Asp Asn Ser Leu Ala Leu Asn
            1400                1405                1410
```

```
Asn Ile Arg Leu Glu Arg Ser Lys Gly Ser Gly Gln Ile Gln Gln
1415                1420                1425

Val Thr Ile Asp Gln Asn Arg Tyr Pro Gly Asn Gly Ile Leu Met
1430                1435                1440

Leu Gln Gln Asn Ala Asn Asn Met Glu Tyr Gly Asn Tyr Gly Val
1445                1450                1455

His Arg Ala Asp Ile Ile Ala Leu Trp Ser Tyr Ile Ser Tyr Met
1460                1465                1470

Ser Ser Glu Ser Gly Trp Ser Ile Lys Lys Cys Glu Ser Phe Val
1475                1480                1485

Lys Leu Leu Leu Gly Ile Asp Leu Lys Phe Ile Asp Leu Lys Gly
1490                1495                1500

Cys Asp Asn Asp Val Val Asp Leu Phe Asn Lys Leu Asn Thr Tyr
1505                1510                1515

Gly Asp Lys Leu Pro Leu Ser Leu Arg Asp Phe Leu Lys Lys Ile
1520                1525                1530

Ser Glu Lys Asn Phe Cys Glu Lys Met Ser Leu Phe Pro Glu Leu
1535                1540                1545

Gly Ile Ala Leu Met Asn Tyr Thr Asn Glu Leu Arg Asn Val Leu
1550                1555                1560

Arg Val Gly Ser Val Phe Gln Val Asp Ser Val Ala Asn Ile Val
1565                1570                1575

Asn Gly Arg Val Ser Asn Ile Asn Asp Val Tyr Ser Tyr Leu Gly
1580                1585                1590

Asn Leu Leu Ser Asn Val Arg Gln Leu Ser Ser Asn Ile Ala Asp
1595                1600                1605

Leu Leu Asn Asn Pro Asp Ile Tyr Lys Ile Phe Thr Asp Val Gly
1610                1615                1620

Ile Thr Ser Ser Gln Glu Ala Ile Phe Leu Ser Ile Asp Ala Val
1625                1630                1635

Ile Phe Asn Leu Leu Val Ser Glu Ile Lys Ile Asp Asn Ser Gln
1640                1645                1650

Leu Lys Glu Leu Leu Ser Leu Val Gly Gly His Arg Asn Ala Ser
1655                1660                1665

Ser Asn Asn Ala Asn Asn Gly Arg Ser Leu Ser Gln Gly Ile Arg
1670                1675                1680

Tyr Lys Ile Thr Phe Lys Ile Ser Phe Ala Gln Asn Tyr Phe Pro
1685                1690                1695

Val Asp Glu Ile Ile Lys Leu Gln Gln Asp Ala Asn Asn Met Glu
1700                1705                1710

Tyr Gly Val His Gly Val His Arg Thr Asp Ile Ile Ala Leu Trp
1715                1720                1725

Ser Tyr Ile Ser Tyr Ala Ser Ser Lys Ser Lys Trp Leu Phe Lys
1730                1735                1740

Arg Tyr Gln Ser Phe Ala Gly Leu Leu Phe Glu Ile Gly Ala Trp
1745                1750                1755

Gly Lys Cys Thr Ser Ala Glu Arg Val Phe Phe Thr Ser Met Asn
1760                1765                1770

Arg Tyr Ser Glu Lys Leu Pro Leu Lys Val Tyr Asn Phe Ile Arg
1775                1780                1785

Lys Ile Thr Thr Gly Asp Phe Ala Arg Lys Phe Ser Gly Met Gln
1790                1795                1800
```

```
Ser Leu Tyr Thr Tyr Lys Gln Arg Val Tyr Asp Tyr Val Met His
    1805                1810                1815

Cys Val Leu Arg Gly Gly Leu Gly Gly Glu Cys Ser Asp Met Thr
    1820                1825                1830

Leu Arg Glu Ile Ser Asn Glu Leu His Lys Leu Lys Gln Glu Ile
    1835                1840                1845

Tyr Ser Asn Tyr Asp Val Phe Arg Asp Leu Gly Ile Thr Asn Gly
    1850                1855                1860

Gln Gln Glu Val Leu Leu Ile Asn Val Met Met Leu Asn Tyr
    1865                1870                1875

Ala Met Ser Asp Leu Leu Val Ser Thr Thr Gln Val Asn Ser Met
    1880                1885                1890

Leu Ala Asp Val Arg Ser Ser Leu Ser Arg Thr Ala His Cys Leu
    1895                1900                1905

Pro Tyr Gly Thr Val Ser Gln Leu Gln Arg Ser Val Ser His Met
    1910                1915                1920

Lys Tyr Gly Glu Tyr Ser Asn Tyr Arg Ala Ser Val Val Ala Leu
    1925                1930                1935

Trp Ala Cys Ile Ser Cys Leu Ala Ser Phe Asn Asp Asp Met Glu
    1940                1945                1950

Pro Leu Ile Lys Leu Met Leu Glu Gly Asp
    1955                1960

<210> SEQ ID NO 2
<211> LENGTH: 308
<212> TYPE: PRT
<213> ORGANISM: Ehrlichia chaffeensis

<400> SEQUENCE: 2

Glu Leu Leu Ser Leu Val Gly Gly His Arg Asn Ala Ser Asn Asn
1               5                   10                  15

Ala Asn Asn Gly Arg Ser Leu Ser Gln Gly Ile Arg Tyr Lys Ile Thr
            20                  25                  30

Phe Lys Ile Ser Phe Ala Gln Asn Tyr Phe Pro Val Asp Glu Ile Ile
                35                  40                  45

Lys Leu Gln Gln Asp Ala Asn Asn Met Glu Tyr Gly Val His Gly Val
    50                  55                  60

His Arg Thr Asp Ile Ile Ala Leu Trp Ser Tyr Ile Ser Tyr Ala Ser
65                  70                  75                  80

Ser Lys Ser Lys Trp Leu Phe Lys Arg Tyr Gln Ser Phe Ala Gly Leu
                85                  90                  95

Leu Phe Glu Ile Gly Ala Trp Gly Lys Cys Thr Ser Ala Glu Arg Val
                100                 105                 110

Phe Phe Thr Ser Met Asn Arg Tyr Ser Glu Lys Leu Pro Leu Lys Val
            115                 120                 125

Tyr Asn Phe Ile Arg Lys Ile Thr Thr Gly Asp Phe Ala Arg Lys Phe
    130                 135                 140

Ser Gly Met Gln Ser Leu Tyr Thr Tyr Lys Gln Arg Val Tyr Asp Tyr
145                 150                 155                 160

Val Met His Cys Val Leu Arg Gly Gly Leu Gly Gly Glu Cys Ser Asp
                165                 170                 175

Met Thr Leu Arg Glu Ile Ser Asn Glu Leu His Lys Leu Lys Gln Glu
            180                 185                 190

Ile Tyr Ser Asn Tyr Asp Val Phe Arg Asp Leu Gly Ile Thr Asn Gly
            195                 200                 205
```

```
Gln Gln Glu Val Leu Leu Ile Asn Val Met Met Leu Asn Tyr Ala
    210                 215                 220

Met Ser Asp Leu Leu Val Ser Thr Thr Gln Val Asn Ser Met Leu Ala
225                 230                 235                 240

Asp Val Arg Ser Leu Ser Arg Thr Ala His Cys Leu Pro Tyr Gly
                245                 250                 255

Thr Val Ser Gln Leu Gln Arg Ser Val Ser His Met Lys Tyr Gly Glu
                260                 265                 270

Tyr Ser Asn Tyr Arg Ala Ser Val Val Ala Leu Trp Ala Cys Ile Ser
            275                 280                 285

Cys Leu Ala Ser Phe Asn Asp Asp Met Glu Pro Leu Ile Lys Leu Met
    290                 295                 300

Leu Glu Gly Asp
305

<210> SEQ ID NO 3
<211> LENGTH: 1510
<212> TYPE: PRT
<213> ORGANISM: Ehrlichia canis

<400> SEQUENCE: 3

Met Phe Met Gly Arg Trp Trp Cys Lys Asn Ile Val Leu Tyr Leu Ala
1               5                   10                  15

Val Leu Leu Phe Ser Phe Cys Pro Ala Leu Gly Lys Ser Glu Tyr Val
                20                  25                  30

Thr Pro Glu Lys Leu Glu Met Tyr Phe Ala Met Tyr Asn Gly Lys His
            35                  40                  45

Phe Thr Ser Glu Glu Phe Ile Lys Gly Met Gly Tyr His Arg Val Arg
    50                  55                  60

Phe Thr Asp Tyr Val Gly Phe Phe Tyr Gly Tyr Trp Phe Gly Ile His
65                  70                  75                  80

Phe Ser Asp Tyr Asn Gln Val Phe Asp Tyr Lys Glu Asn Asp Ser Val
                85                  90                  95

Tyr Ile Arg Phe Ala Gly His Asn Gln Ile Arg Thr Pro Ser Phe Asn
            100                 105                 110

Gly Tyr Tyr Asn Gly Trp Tyr Lys Asp Ile Glu Asp Ile Tyr Ala Ala
    115                 120                 125

Gln Leu Gly Ile Asn Pro Asp Lys Asn Ser Arg Thr Val Asn Glu His
130                 135                 140

Asp Ile Met Leu Met Gln Leu Ser Ser Tyr Trp Gly Lys Val Thr Glu
145                 150                 155                 160

His Ala Ile Pro Ile Gly Ser Cys Lys Ser Ile Tyr Lys Ser Lys Asn
                165                 170                 175

Pro Gly Phe Tyr Arg Ser Leu Ser Ala Arg Ala Phe Leu Thr Glu Asn
            180                 185                 190

Gly Val His Lys Met Val Cys Val Cys Leu Ile Asn Asp Cys Asn Pro
    195                 200                 205

Asn Thr His Cys Ile Asn Gly Gln Val Arg Cys Lys Arg Val Lys Lys
210                 215                 220

Ser Val Asp Pro Pro Phe Cys Ser Ile Leu Asp Ser Ala Asn Ile
225                 230                 235                 240

Val Ser Ile Thr Pro Leu Lys Phe Ser Gln Gln Thr Phe Phe Arg Pro
                245                 250                 255

Gly Val Arg Ile His Ile Tyr Ser Gly Ser Gly Lys Pro Tyr Ile Glu
```

-continued

```
                260                 265                 270
Asp Leu Tyr Ala Gln Ser Tyr Lys Ile Gly Asp Lys Thr Ser Tyr Asp
                275                 280                 285
Ile Ser Tyr Ala Gly Ile Pro Tyr Lys Phe Gln Ile Tyr Lys Ala Gly
                290                 295                 300
Tyr Asp Met Val Cys Ala Glu Tyr Leu Asn Asn Gly Val Pro Glu Lys
305                 310                 315                 320
Lys Val Cys Leu Pro Ser Pro Gly Leu Val Arg Pro Lys Val Thr Pro
                325                 330                 335
Ser Ser Gly Gly Val His Ile Gln Tyr Gln Asp Cys Gln Gly Leu Pro
                340                 345                 350
Ser Cys Asp Val Asp Val Ser Pro Gly Thr Lys Asp Ser Asn Met Phe
                355                 360                 365
Phe Ser Val Ile Lys Pro Lys Val Asn Leu Asp Asp Tyr Thr Leu Ile
                370                 375                 380
Ser Gln Tyr Glu Cys Asp Gly Gln Val Val His Asp Ile Ser Lys
385                 390                 395                 400
Cys Ser Gly Lys Ser Ala Lys Asp Leu Gly Tyr Ala Ser Asp Ser Asn
                405                 410                 415
Gly Asn Val Thr Cys Val Val Asp Met Pro Phe Val Arg Met Lys Tyr
                420                 425                 430
Phe Leu Lys Lys Asn Asn Arg Asp Leu Trp Leu Ser Arg Tyr Glu Lys
                435                 440                 445
Met Phe Leu Gly Tyr Gly Val Val Asn Asp Glu Thr Asp Asp Gly Lys
                450                 455                 460
Lys Ser Glu Ser Tyr Val Met Cys Asp Tyr Gly Ser Ala Ile Asn Ile
465                 470                 475                 480
Ala Asn Met Gln Gln Gly Glu Leu Asp Lys Val Lys Ser Val Lys Gln
                485                 490                 495
Asp Leu Phe Phe Asp Ile Ala Gly His Tyr Asn Pro Lys Gly Asn Pro
                500                 505                 510
Cys Val Ser Asn Val Leu Tyr Lys Tyr Asp Ser Thr Arg Phe Tyr Lys
                515                 520                 525
Lys Asp Arg Gly Val Ser Cys Lys Asp Asn Ala Ala Ser Asn Asn Leu
                530                 535                 540
Met Gly Glu Phe Asp Gly Cys Ser Ser Leu Tyr Asp Ser Asp Asp
545                 550                 555                 560
Phe Thr Asn Phe Phe His Glu Gly Asp Glu Leu Asp Lys Ile Lys
                565                 570                 575
Pro Leu Asn Pro Ile Leu Gln Gly Met Cys Val Ser Asn Phe Pro Ser
                580                 585                 590
Tyr Lys Tyr Gly Lys Arg Ser Val Val Arg Asn Val Leu Gln Asn Thr
                595                 600                 605
Tyr Lys Leu Ser Ile Asp Lys Lys Asn Ser Thr Cys Asp Phe Leu Lys
                610                 615                 620
Ile Glu Ala Trp Gly Gly Ala Ser Gly Val Ser Arg Ser Gly Lys
625                 630                 635                 640
Ser Gly Lys Pro Gly Asn Tyr Val Met Gly Ile Leu Lys Phe Asp Lys
                645                 650                 655
Asp Val Val Asp Lys Lys Leu Ile Ile Asp Ile Gly Thr Gly Gly Thr
                660                 665                 670
Gly Ser Ser His Leu Ser Asn Ala Gly Gly Asp Thr Thr Val Lys Leu
                675                 680                 685
```

-continued

Cys Asp Asp Asp Glu Asn Cys Thr Ile Lys Leu Val Ala Asn Gly
690             695                 700

Gly Asp Val Gly Gly Asn Tyr Leu Lys Asp Asn Ser Glu Gly Val Asp
705             710                 715                 720

Lys Leu Val His Tyr Arg Phe Ala Thr Gly Leu Arg Asp Ser Gly Glu
        725                 730                 735

Gly Glu Ile Leu Ile Pro Tyr Gln Ser Pro Asp Glu Pro Tyr Gly Lys
            740                 745                 750

Leu Gln Lys Asp Ser Lys Glu Cys Asn Cys Asn Ser Ser Thr Leu Glu
        755                 760                 765

Lys Asn Ser Asn Lys Tyr Phe Gly Ser Gly Gly Cys Ser Gly Ile Tyr
        770                 775                 780

Asn Cys Ala Gln Glu Gly Ala Asp Gly Met Val Lys Leu Thr Cys Glu
785             790                 795                 800

Lys Trp Ser Gly Ser Val Gly Lys Ile Lys Leu Ile Asp Glu Asn Ser
            805                 810                 815

Cys Asn Asn Val Leu Thr Ala Phe Ile Glu Lys Thr Asn Lys Pro Met
            820                 825                 830

Gly Gly Met Pro Asp Lys Val Lys Lys Phe Leu Asp Lys Ile Ser Asp
        835                 840                 845

Val Thr Phe Cys Arg Lys Val Gln Asn Met Thr Ser Leu Ile Thr Ala
850             855                 860

Leu Tyr Asp Tyr Phe Ser Met Ile Asn Thr Leu Phe Ser Ser Lys Asn
865             870                 875                 880

Met Ser Asn Asp Leu Pro Asn Leu Arg Lys Arg Leu Leu Thr Glu Leu
            885                 890                 895

Ser Asn Glu Lys Val Gln Leu Val Phe Lys Glu Leu Gly Ile Asp Asp
            900                 905                 910

Asn Pro Glu Thr Ile Leu Leu Tyr Ile Asp Ala Ile Asn Phe Asn Tyr
        915                 920                 925

Gly Ile Ser Ile Ser Lys Pro Pro Glu Gly Leu Leu Asn His Tyr Val
        930                 935                 940

Ala Asp Asp Lys Phe Asp Tyr Asp Leu Ser Lys His Ala Val Asp Tyr
945             950                 955                 960

Asn Thr Leu Ser Asp Asp Glu Ala Met Met Phe Asn Val Val Gly Glu
            965                 970                 975

Asp Thr Glu Arg Trp Phe Ser Val Lys Leu Gln Asn Gln Gln Phe Val
            980                 985                 990

Gln Glu Tyr Gly Glu Phe Ile Asp Phe Ile His Lys Asn Val Met Ala
            995                 1000                1005

Asp Lys Asn Gly Tyr Lys Lys Asn Asn Ile Val Val Ser Trp Met
        1010                1015                1020

Tyr Asn Phe Phe Glu Thr Asp Lys Gln Ile Phe Asp Leu Tyr Ala
        1025                1030                1035

Ala Pro Phe Val Glu Leu Met Leu Gly Val Asp Leu Asp Lys Phe
        1040                1045                1050

Met Lys Trp Arg Gln Cys Gly Asp Thr Asn Val Lys Leu Phe Asp
        1055                1060                1065

Ala Ile Ala Leu Tyr Lys Asp Lys Leu Pro Thr Gly Val Gln Glu
        1070                1075                1080

Phe Ile Glu Lys Ile Ser Asn Pro Asn Phe Cys Val Glu Phe Pro
        1085                1090                1095

-continued

| | | | | | | | | | | | |
|---|---|---|---|---|---|---|---|---|---|---|---|
|Gly|Met 1100|Thr|Leu|Leu|Gly 1105|Glu|Tyr|Ile|Ser 1110|Glu|Leu|Glu|Asn|Tyr|
|Met|Ser 1115|Gly|Asn|Leu|Phe 1120|Asn|Ser|Leu|Asn 1125|Lys|Asn|Asp|Ile|Ile|
|Asp|Arg 1130|Gly|Ser|Asp|Lys 1135|Leu|Ser|Asn|Val 1140|Val|Glu|Gln|Leu|Asp|
|Asp|Ser 1145|Val|Gly|Glu|Asn 1150|Tyr|Glu|Val|Phe 1155|His|Asn|Met|Gly|Ile|
|Leu|Glu 1160|Asp|Glu|Thr|Leu 1165|Leu|Ile|Asp|Ala 1170|Val|Val|Phe|Asn|Tyr|
|Val|Met 1175|Ser|Lys|Leu|Asn 1180|Ile|Ser|Ser|Ala 1185|Gln|Ile|Asp|Asn|Val|
|Phe|Ser 1190|Leu|Leu|Asn|Asn 1195|Val|Ser|Val|Arg 1200|Tyr|Thr|Asp|Arg|Leu|
|Pro|Tyr 1205|Asp|Thr|Ile|Leu 1210|Glu|Leu|Leu|Arg 1215|Asn|Ala|Asn|Ser|Met|
|Lys|Tyr 1220|Gly|Gln|Asp|Gly 1225|Val|Phe|Arg|Ala 1230|Asn|Met|Ile|Ala|Leu|
|Trp|Ser 1235|Tyr|Thr|Ser|Tyr 1240|Tyr|Val|Phe|Asp 1245|Val|Arg|Trp|Ser|Val|
|Asn|Tyr 1250|Phe|Arg|Ser|Phe 1255|Val|Lys|Leu|Leu 1260|Leu|Gly|Ile|Asp|Leu|
|Lys|Ser 1265|Ile|Lys|Leu|Arg 1270|Arg|Cys|Asp|Gln 1275|Asp|Leu|Val|Asp|Leu|
|Phe|Lys 1280|Ala|Phe|Arg|Val 1285|Thr|Glu|Tyr|Ser 1290|Leu|Ser|Lys|Thr|Leu|
|Gln|Asp 1295|Phe|Leu|Ile|Asp 1300|Thr|Asn|Asn|Lys 1305|Asp|Phe|Cys|Gln|Lys|
|Met|Leu 1310|Gln|Phe|Pro|Glu 1315|Leu|Gly|Arg|Val 1320|Leu|Ser|Glu|Tyr|Lys|
|Asn|Ile 1325|Leu|Arg|Asp|Ile 1330|Leu|His|Ser|Gly 1335|Asp|Ile|Phe|Asn|Asp|
|Pro|Ser 1340|Ser|Ala|Thr|Val 1345|Asn|Met|Gln|Leu 1350|Ser|Asn|Ile|Met|Lys|
|Leu|Arg 1355|Ser|Arg|Ile|Lys 1360|Tyr|Leu|Leu|Asn 1365|Asp|Pro|Ala|Val|Tyr|
|Ser|Val 1370|Phe|Thr|Asp|Val 1375|Gly|Ile|Thr|Asn 1380|Thr|Gln|Ala|Gln|Ile|
|Pro|Leu 1385|Ile|Ile|Asp|Ala 1390|Val|Met|Leu|Asn 1395|Thr|Leu|Met|Leu|Asp|
|Ala|Asn 1400|Ile|Ser|Ser|Ala 1405|Asn|Leu|Ser|Lys 1410|Leu|Ile|Ser|Phe|Ala|
|Val|Lys 1415|Asp|Arg|Thr|Leu 1420|Ser|Val|Val|Arg 1425|Val|Gly|Asp|Pro|Val|
|Arg|Lys 1430|Gly|Asn|Lys|Ile 1435|Leu|His|Arg|Leu 1440|Arg|Ile|Thr|Lys|Thr|
|Val|Thr 1445|Lys|Phe|Pro|Asp 1450|Asp|Thr|Ile|Leu 1455|Lys|Leu|Gln|Arg|Asn|
|Ala|Asn 1460|Ser|Thr|Gln|Tyr 1465|Gly|Asn|Tyr|Gly 1470|Ser|Tyr|Lys|Thr|Asp|
|Ile|Ile 1475|Val|Met|Trp|Ser 1480|Cys|Met|Leu|Tyr 1485|Leu|Ala|Ser|Lys|Ala|
|Ser|Trp|Ser|Ser|Glu|Glu|Phe|Glu|Ser|Phe|Val|Asn|Leu|Val|Leu|

```
              1490              1495              1500
Glu Ile Asp Val Lys Asn Leu
    1505             1510

<210> SEQ ID NO 4
<211> LENGTH: 103
<212> TYPE: PRT
<213> ORGANISM: Ehrlichia canis

<400> SEQUENCE: 4

Lys Leu Ile Ser Phe Ala Val Lys Asp Arg Thr Leu Ser Val Val Arg
1               5                   10                  15

Val Gly Asp Pro Val Arg Lys Gly Asn Lys Ile Leu His Arg Leu Arg
            20                  25                  30

Ile Thr Lys Thr Val Thr Lys Phe Pro Asp Asp Thr Ile Leu Lys Leu
        35                  40                  45

Gln Arg Asn Ala Asn Ser Thr Gln Tyr Gly Asn Tyr Gly Ser Tyr Lys
    50                  55                  60

Thr Asp Ile Ile Val Met Trp Ser Cys Met Leu Tyr Leu Ala Ser Lys
65                  70                  75                  80

Ala Ser Trp Ser Ser Glu Glu Phe Glu Ser Phe Val Asn Leu Val Leu
                85                  90                  95

Glu Ile Asp Val Lys Asn Leu
            100

<210> SEQ ID NO 5
<211> LENGTH: 1710
<212> TYPE: PRT
<213> ORGANISM: Ehrlichia ruminantium

<400> SEQUENCE: 5

Met Arg Ile Gln His Tyr Ser Ser Val Ile Leu Leu Ile Ile Leu
1               5                   10                  15

Ile Lys Pro Leu Leu Leu Tyr Ala Asp Thr Glu Lys His Ile Gly Gln
            20                  25                  30

Leu Glu Met Gly Phe Tyr Met Val Gly Glu Lys Val Phe Val Gly Asp
        35                  40                  45

Lys Val Phe His Met Ser Tyr Phe Thr Arg Arg Ser Met Ile Asn His
    50                  55                  60

Glu Gly Tyr Tyr Gly Leu His Phe Leu Asp Tyr Tyr Thr Pro Leu Asp
65                  70                  75                  80

Asp Ala Glu Ser Arg Asn Glu Ser Val Thr Ile Arg Phe Ala Gln Tyr
                85                  90                  95

Asn Leu Asp Asn Arg Glu Lys Tyr Tyr Gly Arg Tyr Leu Asn Gly Trp
            100                 105                 110

Tyr Pro Asp Glu Glu Asn Lys Leu Ile Asp Asn Leu Asn Ile Pro Arg
        115                 120                 125

Asp Arg Ser Lys Arg Asn Phe Ala Glu His Glu Val Met Phe Ile Ala
    130                 135                 140

Leu Ser Ser Tyr Trp Gly Asn Val Thr Leu His Thr Leu Pro Val Gly
145                 150                 155                 160

Ser Cys Lys Met Leu Tyr Gly Gly Ser Thr Phe Tyr Asp Ser Ile Ala
                165                 170                 175

Val Ile Thr Phe Asn Glu Met Met Lys Glu His Glu Tyr Val Cys Ile
            180                 185                 190

Cys Phe Val Lys Asn Cys Ser Ser Lys Pro Val Ile Glu Ser Cys Asp
```

```
              195                 200                 205
Phe Lys Ser Leu His Cys Thr Arg Arg Lys Leu Pro Val Asn Pro Pro
210                 215                 220
Pro Phe Cys Glu Met Phe Asp Ile Lys Asn Ile Val Thr Ile Val Pro
225                 230                 235                 240
Leu Ala Phe Ser Ser Gln Thr Phe Phe Lys Ser Gly Ala Arg Val Tyr
                245                 250                 255
Ile Arg Ala Gly Ser Glu Val Pro His Val Ile Asp Leu Tyr Ala Lys
                260                 265                 270
Ser Tyr Lys Ile Gly Glu Lys Ser Thr Tyr Asn Ile Glu Tyr Lys Gly
                275                 280                 285
Val Pro Tyr Val Phe Gln Val Tyr Lys Lys Gly Tyr Asp Thr Val Cys
                290                 295                 300
Val Asp Tyr Thr Asp Asn Gly Ile Pro Glu Lys Thr Val Cys Val Pro
305                 310                 315                 320
Ser Pro Ser Leu Val Arg Pro Lys Ile Ser Phe Ser Asn Asn Ser Val
                325                 330                 335
Asn Ile Lys Tyr Gln Asp Cys Gln Asp Ser Pro Val Cys Asp Val Asn
                340                 345                 350
Val Pro Val Gly Thr His Asp Lys Asp Leu Ser Phe Ser Val Ile Lys
                355                 360                 365
Pro Lys Ile Asn Lys Asp Asp Tyr Thr Leu Leu Thr Glu Tyr Lys Cys
370                 375                 380
Ala Asp Gly Gln Val Val Tyr Asp Ala Asn Lys Cys Pro Asp Ile Asn
385                 390                 395                 400
Ser Val Lys Lys Leu Gly Tyr Ala His Asp Asp Asn Gly Asn Val Thr
                405                 410                 415
Cys Val Ile Asn Met Pro Phe Val Pro Thr Val Tyr Ser Ile Lys Lys
                420                 425                 430
Asn Asn Arg Asp Leu Trp Leu Arg Arg His Glu Asn Met Leu Gln Gly
                435                 440                 445
Tyr Gly Ile Val Ile Glu Lys Thr Val Asp Gly Lys Lys Ser Glu Lys
                450                 455                 460
Tyr Val Gln Cys Asp Tyr Lys Tyr Ala Ile Asp Ile Thr Lys Leu Thr
465                 470                 475                 480
Gln Asp Gln Leu Ala Gln Met Arg Arg Met Lys Ser Val Phe Phe Asn
                485                 490                 495
Ile Pro Gly His Tyr Asn Pro Lys Asp Arg Ala Cys Gln Gly Ser Val
                500                 505                 510
Ile Tyr Lys Tyr Asp Ser Asn Arg Leu Tyr Glu Lys Gly Lys Glu Ile
                515                 520                 525
Ser Cys Lys Asp Val Val Thr Trp Ser Asp Glu Gln Ser Thr Phe Tyr
530                 535                 540
Gly Cys Ser Ser Leu Tyr Phe Asn Asp Asp Phe Thr Asp Phe Phe
545                 550                 555                 560
His Glu Asn Ser Asp Val Gln Asn Ile Lys Pro Leu Asn Pro Ile Leu
                565                 570                 575
Gln Gly Met Cys Val Ser Asn Phe Pro Ser Thr Tyr Arg Ile Arg
                580                 585                 590
Glu Asn Arg Lys Val Leu Pro Thr Ser Tyr Ser Leu Arg Ile Asn Glu
                595                 600                 605
Lys Lys Thr Ser Cys Asp Phe Ile Lys Ile Glu Val Trp Gly Gly Gly
                610                 615                 620
```

```
Glu Ser Gly Ser Val Gly Ser Thr Lys Ser Gly Lys Ala Gly Asn Tyr
625                 630                 635                 640

Ile Met Gly Val Leu Lys Leu Asp Lys Ser Val Met Asp Lys Arg Leu
            645                 650                 655

Ile Ile Asp Ile Gly Ala Gly Lys Gly Asp Arg His Leu Ser Asn
        660                 665                 670

Ala Gly Gly Asn Thr Ser Val Lys Leu Cys Thr Ser Asp Asn Gly Ser
        675                 680                 685

Asp Cys Val Ile Ser Leu Ile Ala Gln Gly Gly Ser Lys Gly Asp Asp
        690                 695             700

Tyr Leu Gln Asp Lys Ser Ser Gly Thr Asn Leu Leu Ala His Tyr Arg
705                 710                 715                 720

Leu Phe Ser Gly His Arg Asn Val Glu Asp Glu Ile Leu Ile Pro
                725                 730                 735

Tyr Gln Asn Pro Asp Leu Phe Glu Gly Lys Ile Ser Lys Gln Ala Glu
            740                 745                 750

Glu Cys Met Tyr Arg Asn Pro Glu Leu Glu Lys Asn Ser Asn Lys Tyr
            755                 760                 765

Pro Gly Ala Gly Gly Cys Ser Ser Val His Thr Asn Gly Gln Glu Gly
770                 775                 780

Ala Asn Gly Ile Val Lys Leu Thr Cys Glu Lys Trp Ser Gly Thr Pro
785                 790                 795                 800

Gly Thr Ile Glu Leu Glu Asp Glu Asn Ala Cys Ser Ala Ala Leu Val
                805                 810                 815

Thr Phe Ile Glu Glu Ile Asn His Ser Lys Asp Tyr Leu Pro Glu Lys
                820                 825                 830

Ile Lys Glu Phe Leu Lys Lys Ile Ser Gln Ile Ser Ile Cys Arg Glu
            835                 840                 845

Leu Lys Ser Leu Pro Lys Leu Val Ser Leu Ser Gly Tyr Phe Met
850                 855                 860

Ser Val Lys Thr Leu Leu Thr Asp Thr Pro Asn Tyr Pro Ala Leu Ile
865                 870                 875                 880

Lys Ser Arg Lys Ser Leu Leu Ala Glu Leu Asn Asp Ser Lys Val Lys
                885                 890                 895

Glu Ala Leu Lys Arg Ile Gly Ile Asp Tyr Ser Pro Asp Met Thr Leu
            900                 905                 910

Leu Tyr Ile Asp Ala Leu Val Phe Asn Phe Gly Ala Asn Val Leu Asn
        915                 920                 925

Lys Pro Gly Gln Tyr Leu Leu Asn Tyr Tyr Val Ala Ala Asn Asp Asp
            930                 935                 940

Ser Ser Val Gly Ile Asp Asp Ser Lys Val Val Pro Asp Glu Leu Ala
945                 950                 955                 960

Phe Ala Met Asn Ala Thr Ser Asn Arg Ser Lys Ser Arg Asp Phe Ser
                965                 970                 975

Val Arg Val Ser Asp Gln Gln Phe Ile Lys Lys Tyr Arg Ser Phe Ile
            980                 985                 990

Glu Ala Met Glu Met Tyr Thr Arg Asp Lys Lys Pro Gly His Ser Lys
            995                 1000                1005

Glu Asn Asn Asn Ile Val Met Ser Trp Met Tyr Ser Phe Phe Lys
            1010            1015                1020

Ala Asp Lys Arg Leu Phe Asp Ile Tyr Ala His Leu Phe Val Glu
            1025            1030                1035
```

-continued

| | | | | | | | | | | | | |
|---|---|---|---|---|---|---|---|---|---|---|---|---|
|Leu|Met|Leu|Gly|Met|Asp|Leu|Ile|Glu|Phe|Ile|Glu|Trp|Tyr|His|
| |1040| | | |1045| | | |1050| | | | | |

Cys Ser Glu Asp Ile Leu Gln Leu Phe Lys Gln Ile Asn Gln Tyr
    1055             1060              1065

Lys Gln Lys Leu Pro Leu Lys Val Gln Asn Phe Ile Thr Lys Ile
    1070             1075              1080

Ser Gly Glu Asp Lys Phe Cys Ser Glu Met Ser Arg Tyr Ile Gln
    1085             1090              1095

Val Asn Gln Leu Leu His His Tyr Ala Asp Asn Met Lys His Phe
    1100             1105              1110

Ile Asn Ser Ile Phe Gln Asp Ile Asn Asn Phe Ser Phe Met
    1115             1120              1125

Met His Asp Met Lys Ser Leu Ile Ser Gln Trp Arg Asp Phe Leu
    1130             1135              1140

Gly Lys Ser Asp Ile Arg Asn Ile Phe Thr Arg Val Gly Val Thr
    1145             1150              1155

Glu Asn Asn Asp Glu Ile Arg Leu Leu Phe Asp Ala Ala Val Leu
    1160             1165              1170

Asn Asn Ile Leu Ser Glu Tyr Asn Ala Ser Glu Gly Ser Ile Leu
    1175             1180              1185

Asp Gln Leu Arg Asn Ser Arg Val Gly Arg Asp Ala Leu Thr Val
    1190             1195              1200

Leu Asp Phe Pro Gly Asp Tyr Leu Phe Met Leu Gln Asp Asn Cys
    1205             1210              1215

Asn Lys Met Glu Cys Gly Asp Asn Gly Ile Tyr Arg Phe Asp Ile
    1220             1225              1230

Val Ser Leu Trp Thr Phe Val Ala Phe Tyr Met Asp Asp Lys Phe
    1235             1240              1245

Asn Asp Lys His Phe Glu Tyr Phe Ile Lys Leu Met Leu Asp Gln
    1250             1255              1260

Asp Leu Gln Lys Leu Ser Ala Ala Ser Lys Lys Ser Thr Glu Gln
    1265             1270              1275

Thr Leu Thr Glu Leu Val Asp Asn Ile Lys Lys Tyr Arg Asn Lys
    1280             1285              1290

Leu Ser Glu Ala Ala Asn Asn Phe Ile Asp Lys Ile Ser Thr His
    1295             1300              1305

Arg Phe Ser Gly Glu Leu Val Gln Phe Pro Glu Leu Val Asp Leu
    1310             1315              1320

Leu His Lys Tyr Glu Met Ser Ile Arg Asp Phe Ile Lys Gly Leu
    1325             1330              1335

Ala Asp Val Ser Asn Ser Asp Val Met Ser Ser Leu Asp Asp Thr
    1340             1345              1350

Ser Lys Val Tyr Lys Glu Leu Gly Asp Ile Leu Asn Lys Glu Asn
    1355             1360              1365

Val Lys Lys Ala Phe Ala Asn Ala Gly Ile Lys Asn Ser Val Asn
    1370             1375              1380

Glu Ile Arg Leu Leu Phe Asp Ala Val Ile Ile Asn Tyr Leu Leu
    1385             1390              1395

Ser Asp Leu Asn Pro Phe Lys Lys Leu Leu Ile Asp Val Lys Thr
    1400             1405              1410

Thr Ser Ser Ile Asp Arg Lys Met Gln Ile Met Lys Ser Ile Gly
    1415             1420              1425

Asn Val Asp Leu Ser Val Leu Lys Gln Asp Val Val Asp Met Ala

```
                1430                1435                1440
Tyr Gly Glu His Ser Asn His Arg Phe Asn Ile Val Val Leu Trp
    1445                1450                1455
Cys Tyr Met Ile Asn Ser Gln Tyr Tyr Tyr Arg Asp Phe Ala Glu
    1460                1465                1470
Arg Tyr Phe Asn Pro Leu Val Lys Leu Val Leu Gly Glu Asn Ile
    1475                1480                1485
Lys Glu Ser Thr Ser Glu Arg Arg Gln Phe Thr Arg Phe Ile Asn
    1490                1495                1500
Lys Ile Ser Lys Tyr Lys Glu Lys Leu Pro Asp Gly Ile Asn Asp
    1505                1510                1515
Phe Ile Ala Lys Ile Ser Thr Lys Glu Phe Tyr Asn Glu Leu Ile
    1520                1525                1530
Gln Leu Pro Glu Leu Ile Gly Leu Leu Asp Lys Glu Glu Thr Leu
    1535                1540                1545
Met Arg Asn Phe Ile Lys Glu Leu Val Asn Leu Ser Asn Asn Gly
    1550                1555                1560
Val Ile Asn Ala Met Asp Asn Ile Ser Gln Met Thr Glu Glu Phe
    1565                1570                1575
Asn Asp Ile Leu Lys Ala Pro Lys Val Lys Lys Ile Phe Ala Asn
    1580                1585                1590
Ile Gly Leu Thr Lys Tyr Gln Glu Val Arg Leu Leu Phe Asp Ala
    1595                1600                1605
Ala Ile Ile Asn Tyr Leu Leu Ala Glu Leu Ser Pro Phe Lys Lys
    1610                1615                1620
Leu Val Ile Asp Ile Asp Lys Thr Pro Tyr Leu Gln Asn Leu Ile
    1625                1630                1635
Ile Asn Ser Met Ile Thr Ile His Gln Ile Asp Leu Gln Ser Phe
    1640                1645                1650
Thr Gln Asn Ile Leu Asn Lys Asp Gly Lys Tyr Asn Glu His Arg
    1655                1660                1665
Phe Asp Ile Ile Val Leu Trp Ser Tyr Met Phe Tyr Arg Ala Tyr
    1670                1675                1680
Tyr Tyr Asp Asp Phe Ala Asn Glu Tyr Phe Asn Pro Leu Leu Glu
    1685                1690                1695
Phe Val Leu Gly Asp Arg Val Pro Asn Leu Arg Lys
    1700                1705                1710

<210> SEQ ID NO 6
<211> LENGTH: 301
<212> TYPE: PRT
<213> ORGANISM: Ehrlichia ruminantium

<400> SEQUENCE: 6

Asp Val Lys Thr Thr Ser Ser Ile Asp Arg Lys Met Gln Ile Met Lys
1               5                   10                  15

Ser Ile Gly Asn Val Asp Leu Ser Val Leu Lys Gln Asp Val Val Asp
            20                  25                  30

Met Ala Tyr Gly Glu His Ser Asn His Arg Phe Asn Ile Val Val Leu
        35                  40                  45

Trp Cys Tyr Met Ile Asn Ser Gln Tyr Tyr Tyr Arg Asp Phe Ala Glu
    50                  55                  60

Arg Tyr Phe Asn Pro Leu Val Lys Leu Val Leu Gly Glu Asn Ile Lys
65                  70                  75                  80
```

-continued

Glu Ser Thr Ser Glu Arg Arg Gln Phe Thr Arg Phe Ile Asn Lys Ile
            85                  90                  95

Ser Lys Tyr Lys Glu Lys Leu Pro Asp Gly Ile Asn Asp Phe Ile Ala
        100                 105                 110

Lys Ile Ser Thr Lys Glu Phe Tyr Asn Glu Leu Ile Gln Leu Pro Glu
        115                 120                 125

Leu Ile Gly Leu Leu Asp Lys Glu Thr Leu Met Arg Asn Phe Ile
130                 135                 140

Lys Glu Leu Val Asn Leu Ser Asn Asn Gly Val Ile Asn Ala Met Asp
145                 150                 155                 160

Asn Ile Ser Gln Met Thr Glu Glu Phe Asn Asp Ile Leu Lys Ala Pro
                165                 170                 175

Lys Val Lys Lys Ile Phe Ala Asn Ile Gly Leu Thr Lys Tyr Gln Glu
            180                 185                 190

Val Arg Leu Leu Phe Asp Ala Ala Ile Ile Asn Tyr Leu Leu Ala Glu
        195                 200                 205

Leu Ser Pro Phe Lys Lys Leu Val Ile Asp Ile Asp Lys Thr Pro Tyr
    210                 215                 220

Leu Gln Asn Leu Ile Ile Asn Ser Met Ile Thr Ile His Gln Ile Asp
225                 230                 235                 240

Leu Gln Ser Phe Thr Gln Asn Ile Leu Asn Lys Asp Gly Lys Tyr Asn
                245                 250                 255

Glu His Arg Phe Asp Ile Ile Val Leu Trp Ser Tyr Met Phe Tyr Arg
            260                 265                 270

Ala Tyr Tyr Tyr Asp Asp Phe Ala Asn Glu Tyr Phe Asn Pro Leu Leu
        275                 280                 285

Glu Phe Val Leu Gly Asp Arg Val Pro Asn Leu Arg Lys
    290                 295                 300

<210> SEQ ID NO 7
<211> LENGTH: 680
<212> TYPE: PRT
<213> ORGANISM: Ehrlichia chaffeensis

<400> SEQUENCE: 7

Lys Ile Asn Ile His Val Leu Arg Asp Tyr Ala Asn Val His Tyr Asn
1               5                   10                  15

Thr Tyr Tyr Gly Leu His Phe Asp Asn Tyr Tyr Lys Pro Val Asp Asn
            20                  25                  30

Thr Glu Gly Asn Leu Asp Ser Val Met Ile Arg Phe Ala Ser His Asp
        35                  40                  45

Ser Tyr Arg Tyr Met Ser Phe Met Gln Tyr Val Lys Gly Gln Tyr Gln
    50                  55                  60

Asp Val Glu Asn Leu Asn Val Ser Gly Leu Asp Ile Pro Phe Asn Arg
65                  70                  75                  80

Glu Asp Arg Thr Phe Asp Asp His Asp Val Met Phe Met Gln Leu Ser
            85                  90                  95

Ser Tyr Trp Gly Lys Val Thr Phe His Ser Leu Pro Ile Gly Gly Cys
        100                 105                 110

Lys Val Leu Tyr Ala Gly Ser Ile Ile Tyr Asp Pro Val Ser Ala Ile
        115                 120                 125

Ala Phe Leu Glu Asn Glu Asn Ala Ser Ser Lys Val Cys Ile Cys Phe
    130                 135                 140

Val Gly Lys Cys Asn Val Lys Pro Glu Arg Asn Ser Cys Asp Lys Lys
145                 150                 155                 160

```
Ser Ile Arg Cys Lys Val Thr Val Ala Ile Asn Pro Pro Phe
            165                 170             175

Cys Ser Ile Leu Asp Ala Ser Ser Ile Val Ser Ile Thr Pro Leu Arg
                180                 185                 190

Phe Ser Gln Gln Thr Phe Phe Arg Pro Gly Val Arg Ile His Ile Tyr
            195                 200                 205

Ser Gly Ser Gly Asn Pro Tyr Thr Lys Glu Leu Tyr Val Lys Ser His
    210                 215                 220

Lys Ile Gly Asp Lys Thr Ser Tyr Asn Ile Ser His Ala Gly Ile Pro
225                 230                 235                 240

Tyr Glu Phe Gln Val Tyr Lys Ala Gly Tyr Asp Thr Val Cys Ala Glu
                245                 250                 255

Tyr Ser Asn Asn Gly Glu Lys Gly Lys Lys Val Cys Val Pro Ser Pro
            260                 265                 270

Gly Leu Met Arg Pro Lys Val Thr Ser Asn Ala Asn Gly Val Asn Ile
            275                 280                 285

Gln Tyr Gln Asp Cys Gln Gly Leu Ser Ser Cys Ser Val Asp Met Leu
    290                 295                 300

Pro Gly Thr Gln Asp Leu Asp Met Tyr Phe Ser Val Ile Lys Pro Lys
305                 310                 315                 320

Ile Asp Phe Asn Asn Tyr Thr Leu Leu Ser Arg Tyr Glu Cys Glu Asp
                325                 330                 335

Gly Lys Ile Val Glu Asn Glu Asn Gln Cys Val Asn Gly Ile Gly Gln
            340                 345                 350

Arg Leu Gly Tyr Val His Asp Asn Ser Asn Val Thr Cys Val Val
    355                 360                 365

Asp Met Pro Phe Val Pro Met Lys Tyr Ser Ile Lys Lys Asn His Arg
370                 375                 380

Asp Leu Trp Leu Ser Met His Asp Lys Met Leu Leu Gly Tyr Gly Val
385                 390                 395                 400

Val Val Gly Lys Thr Asp Thr Gly Lys Asp Val Glu Arg Tyr Val Gln
                405                 410                 415

Cys Asp Gln Lys Phe Ala Ile Asp Ile Lys Ser Met Thr Gln Glu Gln
            420                 425                 430

Leu Asn Lys Ile Thr Arg Ile Arg Gln Asp Ala Phe Phe Asp Ile Gly
            435                 440                 445

Gly His Tyr Asn Pro Lys Asn Ala Pro Cys Gln Asp Ser Met Leu Tyr
    450                 455                 460

Arg Tyr Glu Asn Asn Arg Leu Tyr Glu Lys Gly Gln Val Ser Cys
465                 470                 475                 480

Lys Asn Met Val Glu Leu Asp Tyr Gly Thr Lys Lys Ile Lys Gly Cys
                485                 490                 495

Ser Ser Leu Tyr Met Ser Asp Asp Phe Thr Tyr Phe His Glu
            500                 505                 510

Asn Asp Glu Leu Glu Lys Ile Val Pro Leu Asn Pro Ile Leu Gln Gly
            515                 520                 525

Met Cys Val Ser Asn Phe Pro Ser Tyr Glu Tyr Lys Lys Arg Val Leu
530                 535                 540

Val Arg Lys Ile Leu Pro Asp Ser Tyr Lys Leu Gly Ile Asp Gln Lys
545                 550                 555                 560

Asn Thr Glu Cys Asp Phe Leu Lys Ile Glu Ala Trp Gly Gly Gly Ala
                565                 570                 575
```

```
Ser Gly Ile Ser Arg Ser Gly Arg Ser Gly Lys Ala Gly Asn Tyr Val
            580                 585                 590

Met Gly Leu Leu Arg Phe Asp Lys Asn Val Val Asn Lys Lys Leu Ile
    595                 600                 605

Ile Asp Ile Gly Asp Gly Lys Gly Ala Asn Ser Leu Ser Asn Ser
    610                 615                 620

Gly Gly Asp Thr Thr Val Lys Leu Cys Asp Asp Asp Lys Asn Cys
625                 630                 635                 640

Leu Val Lys Ile Ile Ala His Gly Gly Asp Glu Gly Gly Asn Tyr Leu
                645                 650                 655

Gln Asp Ser Ser Glu Gly Ile Asp Asn Leu Val His Tyr Arg Phe Ala
            660                 665                 670

Pro Gly Leu Gln Asn Ser Gly Glu
        675                 680

<210> SEQ ID NO 8
<211> LENGTH: 694
<212> TYPE: PRT
<213> ORGANISM: Ehrlichia canis

<400> SEQUENCE: 8

Met Tyr Asn Gly Lys His Phe Thr Ser Glu Glu Phe Ile Lys Gly Met
1               5                   10                  15

Gly Tyr His Arg Val Arg Phe Thr Asp Tyr Val Gly Phe Phe Tyr Gly
            20                  25                  30

Tyr Trp Phe Gly Ile His Phe Ser Asp Tyr Asn Gln Val Phe Asp Tyr
        35                  40                  45

Lys Glu Asn Asp Ser Val Tyr Ile Arg Phe Ala Gly His Asn Gln Ile
    50                  55                  60

Arg Thr Pro Ser Phe Asn Gly Tyr Tyr Asn Gly Trp Tyr Lys Asp Ile
65                  70                  75                  80

Glu Asp Ile Tyr Ala Ala Gln Leu Gly Ile Asn Pro Asp Lys Asn Ser
                85                  90                  95

Arg Thr Val Asn Glu His Asp Ile Met Leu Met Gln Leu Ser Ser Tyr
            100                 105                 110

Trp Gly Lys Val Thr Glu His Ala Ile Pro Ile Gly Ser Cys Lys Ser
        115                 120                 125

Ile Tyr Lys Ser Lys Asn Pro Gly Phe Tyr Arg Ser Leu Ser Ala Arg
    130                 135                 140

Ala Phe Leu Thr Glu Asn Gly Val His Lys Met Val Cys Val Cys Leu
145                 150                 155                 160

Ile Asn Asp Cys Asn Pro Asn Thr His Cys Ile Asn Gly Gln Val Arg
                165                 170                 175

Cys Lys Arg Val Lys Lys Ser Val Asp Pro Pro Phe Cys Ser Ile
            180                 185                 190

Leu Asp Ser Ala Asn Ile Val Ser Ile Thr Pro Leu Lys Phe Ser Gln
        195                 200                 205

Gln Thr Phe Phe Arg Pro Gly Val Arg Ile His Ile Tyr Ser Gly Ser
    210                 215                 220

Gly Lys Pro Tyr Ile Glu Asp Leu Tyr Ala Gln Ser Tyr Lys Ile Gly
225                 230                 235                 240

Asp Lys Thr Ser Tyr Asp Ile Ser Tyr Ala Gly Ile Pro Tyr Lys Phe
                245                 250                 255

Gln Ile Tyr Lys Ala Gly Tyr Asp Met Val Cys Ala Glu Tyr Leu Asn
            260                 265                 270
```

```
Asn Gly Val Pro Glu Lys Lys Val Cys Leu Pro Ser Pro Gly Leu Val
        275                 280                 285

Arg Pro Lys Val Thr Pro Ser Ser Gly Val His Ile Gln Tyr Gln
        290                 295                 300

Asp Cys Gln Gly Leu Pro Ser Cys Asp Val Asp Val Ser Pro Gly Thr
305                 310                 315                 320

Lys Asp Ser Asn Met Phe Phe Ser Val Ile Lys Pro Lys Val Asn Leu
                325                 330                 335

Asp Asp Tyr Thr Leu Ile Ser Gln Tyr Glu Cys Asp Gly Gly Gln Val
                340                 345                 350

Val His Asp Ile Ser Lys Cys Ser Gly Lys Ser Ala Lys Asp Leu Gly
                355                 360                 365

Tyr Ala Ser Asp Ser Asn Gly Asn Val Thr Cys Val Val Asp Met Pro
        370                 375                 380

Phe Val Arg Met Lys Tyr Phe Leu Lys Asn Asn Arg Asp Leu Trp
385                 390                 395                 400

Leu Ser Arg Tyr Glu Lys Met Phe Leu Gly Tyr Gly Val Val Asn Asp
                405                 410                 415

Glu Thr Asp Asp Gly Lys Lys Ser Glu Ser Tyr Val Met Cys Asp Tyr
                420                 425                 430

Gly Ser Ala Ile Asn Ile Ala Asn Met Gln Gln Gly Glu Leu Asp Lys
        435                 440                 445

Val Lys Ser Val Lys Gln Asp Leu Phe Phe Asp Ile Ala Gly His Tyr
        450                 455                 460

Asn Pro Lys Gly Asn Pro Cys Val Ser Asn Val Leu Tyr Lys Tyr Asp
465                 470                 475                 480

Ser Thr Arg Phe Tyr Lys Lys Asp Arg Gly Val Ser Cys Lys Asp Asn
                485                 490                 495

Ala Ala Ser Asn Asn Leu Met Gly Glu Phe Asp Gly Cys Ser Ser Leu
                500                 505                 510

Tyr Asp Ser Asp Asp Phe Thr Asn Phe Phe His Glu Gly Asp Asp
        515                 520                 525

Glu Leu Asp Lys Ile Lys Pro Leu Asn Pro Ile Leu Gln Gly Met Cys
        530                 535                 540

Val Ser Asn Phe Pro Ser Tyr Lys Tyr Gly Lys Arg Ser Val Val Arg
545                 550                 555                 560

Asn Val Leu Gln Asn Thr Tyr Lys Leu Ser Ile Asp Lys Lys Asn Ser
                565                 570                 575

Thr Cys Asp Phe Leu Lys Ile Glu Ala Trp Gly Gly Ala Ser Gly
                580                 585                 590

Val Ser Arg Ser Gly Lys Ser Gly Lys Pro Gly Asn Tyr Val Met Gly
        595                 600                 605

Ile Leu Lys Phe Asp Lys Asp Val Val Asp Lys Lys Leu Ile Ile Asp
        610                 615                 620

Ile Gly Thr Gly Gly Thr Gly Ser Ser His Leu Ser Asn Ala Gly Gly
625                 630                 635                 640

Asp Thr Thr Val Lys Leu Cys Asp Asp Asp Glu Asn Cys Thr Ile
                645                 650                 655

Lys Leu Val Ala Asn Gly Gly Asp Val Gly Gly Asn Tyr Leu Lys Asp
                660                 665                 670

Asn Ser Glu Gly Val Asp Lys Leu Val His Tyr Arg Phe Ala Thr Gly
                675                 680                 685
```

Leu Arg Asp Ser Gly Glu
    690

<210> SEQ ID NO 9
<211> LENGTH: 692
<212> TYPE: PRT
<213> ORGANISM: Ehrlichia ruminantium

<400> SEQUENCE: 9

Met Val Gly Glu Lys Val Phe Val Gly Asp Lys Val Phe His Met Ser
1               5                   10                  15

Tyr Phe Thr Arg Arg Ser Met Ile Asn His Glu Gly Tyr Tyr Gly Leu
            20                  25                  30

His Phe Leu Asp Tyr Tyr Thr Pro Leu Asp Asp Ala Glu Ser Arg Asn
        35                  40                  45

Glu Ser Val Thr Ile Arg Phe Ala Gln Tyr Asn Leu Asp Asn Arg Glu
    50                  55                  60

Lys Tyr Tyr Gly Arg Tyr Leu Asn Gly Trp Tyr Pro Asp Glu Glu Asn
65                  70                  75                  80

Lys Leu Ile Asp Asn Leu Asn Ile Pro Arg Asp Arg Ser Lys Arg Asn
                85                  90                  95

Phe Ala Glu His Glu Val Met Phe Ile Ala Leu Ser Ser Tyr Trp Gly
            100                 105                 110

Asn Val Thr Leu His Thr Leu Pro Val Gly Ser Cys Lys Met Leu Tyr
        115                 120                 125

Gly Gly Ser Thr Phe Tyr Asp Ser Ile Ala Val Ile Thr Phe Asn Glu
    130                 135                 140

Met Met Lys Glu His Glu Tyr Val Cys Ile Cys Phe Val Lys Asn Cys
145                 150                 155                 160

Ser Ser Lys Pro Val Ile Glu Ser Cys Asp Phe Lys Ser Leu His Cys
                165                 170                 175

Thr Arg Arg Lys Leu Pro Val Asn Pro Pro Phe Cys Glu Met Phe
            180                 185                 190

Asp Ile Lys Asn Ile Val Thr Ile Val Pro Leu Ala Phe Ser Ser Gln
        195                 200                 205

Thr Phe Phe Lys Ser Gly Ala Arg Val Tyr Ile Arg Ala Gly Ser Glu
    210                 215                 220

Val Pro His Val Ile Asp Leu Tyr Ala Lys Ser Tyr Lys Ile Gly Glu
225                 230                 235                 240

Lys Ser Thr Tyr Asn Ile Glu Tyr Lys Gly Val Pro Tyr Val Phe Gln
                245                 250                 255

Val Tyr Lys Lys Gly Tyr Asp Thr Val Cys Val Asp Tyr Thr Asp Asn
            260                 265                 270

Gly Ile Pro Glu Lys Thr Val Cys Val Pro Ser Pro Ser Leu Val Arg
        275                 280                 285

Pro Lys Ile Ser Phe Ser Asn Asn Ser Val Asn Ile Lys Tyr Gln Asp
    290                 295                 300

Cys Gln Asp Ser Pro Val Cys Asp Val Asn Val Pro Val Gly Thr His
305                 310                 315                 320

Asp Lys Asp Leu Ser Phe Ser Val Ile Lys Pro Lys Ile Asn Lys Asp
                325                 330                 335

Asp Tyr Thr Leu Leu Thr Glu Tyr Lys Cys Ala Asp Gly Gln Val Val
            340                 345                 350

Tyr Asp Ala Asn Lys Cys Pro Asp Ile Asn Ser Val Lys Lys Leu Gly
        355                 360                 365

Tyr Ala His Asp Asp Asn Gly Asn Val Thr Cys Val Ile Asn Met Pro
            370                 375                 380

Phe Val Pro Thr Val Tyr Ser Ile Lys Lys Asn Asn Arg Asp Leu Trp
385                 390                 395                 400

Leu Arg Arg His Glu Asn Met Leu Gln Gly Tyr Gly Ile Val Ile Glu
                405                 410                 415

Lys Thr Val Asp Gly Lys Lys Ser Glu Lys Tyr Val Gln Cys Asp Tyr
            420                 425                 430

Lys Tyr Ala Ile Asp Ile Thr Lys Leu Thr Gln Asp Gln Leu Ala Gln
            435                 440                 445

Met Arg Arg Met Lys Ser Val Phe Phe Asn Ile Pro Gly His Tyr Asn
450                 455                 460

Pro Lys Asp Arg Ala Cys Gln Gly Ser Val Ile Tyr Lys Tyr Asp Ser
465                 470                 475                 480

Asn Arg Leu Tyr Glu Lys Gly Lys Glu Ile Ser Cys Lys Asp Val Val
                485                 490                 495

Thr Trp Ser Asp Glu Gln Ser Thr Phe Tyr Gly Cys Ser Ser Leu Tyr
            500                 505                 510

Phe Asn Asp Asp Asp Phe Thr Asp Phe His Glu Asn Ser Asp Val
            515                 520                 525

Gln Asn Ile Lys Pro Leu Asn Pro Ile Leu Gln Gly Met Cys Val Ser
530                 535                 540

Asn Phe Pro Ser Asn Thr Tyr Arg Ile Arg Glu Asn Arg Lys Val Leu
545                 550                 555                 560

Pro Thr Ser Tyr Ser Leu Arg Ile Asn Glu Lys Lys Thr Ser Cys Asp
                565                 570                 575

Phe Ile Lys Ile Glu Val Trp Gly Gly Gly Glu Ser Gly Ser Val Gly
            580                 585                 590

Ser Thr Lys Ser Gly Lys Ala Gly Asn Tyr Ile Met Gly Val Leu Lys
            595                 600                 605

Leu Asp Lys Ser Val Met Asp Lys Arg Leu Ile Ile Asp Ile Gly Ala
610                 615                 620

Gly Gly Lys Gly Asp Arg His Leu Ser Asn Ala Gly Asn Thr Ser
625                 630                 635                 640

Val Lys Leu Cys Thr Ser Asp Asn Gly Ser Asp Cys Val Ile Ser Leu
                645                 650                 655

Ile Ala Gln Gly Gly Ser Lys Gly Asp Asp Tyr Leu Gln Asp Lys Ser
            660                 665                 670

Ser Gly Thr Asn Leu Leu Ala His Tyr Arg Leu Phe Ser Gly His Arg
            675                 680                 685

Asn Val Glu Glu
        690

<210> SEQ ID NO 10
<211> LENGTH: 1976
<212> TYPE: PRT
<213> ORGANISM: Ehrlichia chaffeensis

<400> SEQUENCE: 10

Met Lys Val Trp Cys Tyr Lys Asn Ile Gly Leu Tyr Leu Ile Val Leu
1               5                   10                  15

Leu Ser Phe Val Tyr Pro Arg Ala Leu Leu His Ala Lys Ile Asn Ile
            20                  25                  30

His Val Leu Arg Asp Tyr Ala Asn Val His Tyr Asn Thr Tyr Tyr Gly

```
            35                  40                  45
Leu His Phe Asp Asn Tyr Tyr Lys Pro Val Asp Asn Thr Glu Gly Asn
 50                  55                  60

Leu Asp Ser Val Met Ile Arg Phe Ala Ser His Asp Ser Tyr Arg Tyr
 65                  70                  75                  80

Met Ser Phe Met Gln Tyr Val Lys Gly Gln Tyr Gln Asp Val Glu Asn
                 85                  90                  95

Leu Asn Val Ser Gly Leu Asp Ile Pro Phe Asn Arg Glu Asp Arg Thr
                100                 105                 110

Phe Asp Asp His Asp Val Met Phe Met Gln Leu Ser Ser Tyr Trp Gly
                115                 120                 125

Lys Val Thr Phe His Ser Leu Pro Ile Gly Gly Cys Lys Val Leu Tyr
                130                 135                 140

Ala Gly Ser Ile Ile Tyr Asp Pro Val Ser Ala Ile Ala Phe Leu Glu
145                 150                 155                 160

Asn Glu Asn Ala Ser Ser Lys Val Cys Ile Cys Phe Val Gly Lys Cys
                165                 170                 175

Asn Val Lys Pro Glu Arg Asn Ser Cys Asp Lys Lys Ser Ile Arg Cys
                180                 185                 190

Lys Lys Val Thr Val Ala Ile Asn Pro Pro Phe Cys Ser Ile Leu
                195                 200                 205

Asp Ala Ser Ser Ile Val Ser Ile Thr Pro Leu Arg Phe Ser Gln Gln
210                 215                 220

Thr Phe Phe Arg Pro Gly Val Arg Ile His Ile Tyr Ser Gly Ser Gly
225                 230                 235                 240

Asn Pro Tyr Thr Lys Glu Leu Tyr Val Lys Ser His Lys Ile Gly Asp
                245                 250                 255

Lys Thr Ser Tyr Asn Ile Ser His Ala Gly Ile Pro Tyr Glu Phe Gln
                260                 265                 270

Val Tyr Lys Ala Gly Tyr Asp Thr Val Cys Ala Glu Tyr Ser Asn Asn
                275                 280                 285

Gly Glu Lys Gly Lys Lys Val Cys Val Pro Ser Pro Glu Leu Met Arg
                290                 295                 300

Pro Lys Val Thr Ser Asn Ala Asn Gly Val Asn Ile Gln Tyr Gln Asp
305                 310                 315                 320

Cys Gln Gly Leu Ser Ser Cys Ser Val Asp Met Leu Pro Gly Thr Gln
                325                 330                 335

Asp Leu Asp Met Tyr Phe Ser Val Ile Lys Pro Lys Ile Asp Phe Asn
                340                 345                 350

Asn Tyr Thr Leu Leu Ser Arg Tyr Glu Cys Glu Asp Gly Lys Ile Val
                355                 360                 365

Glu Asn Glu Asn Gln Cys Val Asn Gly Ile Gly Gln Arg Leu Gly Tyr
                370                 375                 380

Val His Asp Asn Asn Ser Asn Val Thr Cys Val Val Asp Met Pro Phe
385                 390                 395                 400

Val Pro Met Lys Tyr Ser Ile Lys Lys Asn His Arg Asp Leu Trp Leu
                405                 410                 415

Ser Met His Asp Lys Met Leu Leu Gly Tyr Gly Val Val Gly Lys
                420                 425                 430

Thr Asp Thr Gly Lys Asp Val Glu Arg Tyr Val Gln Cys Asp Gln Lys
                435                 440                 445

Phe Ala Ile Asp Ile Lys Ser Met Thr Gln Glu Gln Leu Asn Lys Ile
450                 455                 460
```

-continued

Thr Arg Ile Arg Gln Asp Ala Phe Phe Asp Ile Gly His Tyr Asn
465                 470                 475                 480

Pro Lys Asn Ala Pro Cys Gln Asp Ser Met Leu Tyr Arg Tyr Glu Asn
            485                 490                 495

Asn Arg Leu Tyr Glu Lys Gly Gly Gln Val Ser Cys Lys Asn Met Val
                500                 505                 510

Glu Leu Asp Tyr Gly Thr Lys Lys Ile Lys Gly Cys Ser Ser Leu Tyr
                515                 520                 525

Ile Ser Asp Asp Asp Phe Thr Tyr Phe Phe His Glu Asn Asp Glu Leu
        530                 535                 540

Glu Lys Ile Val Pro Leu Asn Pro Ile Leu Gln Gly Met Cys Val Ser
545                 550                 555                 560

Asn Phe Pro Ser Tyr Glu Tyr Lys Lys Arg Val Leu Val Arg Lys Ile
                565                 570                 575

Leu Pro Asp Ser Tyr Lys Leu Gly Ile Asp Gln Lys Asn Thr Glu Cys
                580                 585                 590

Asp Phe Leu Lys Ile Glu Ala Trp Gly Gly Ala Ser Gly Ile Ser
        595                 600                 605

Arg Ser Gly Arg Ser Gly Lys Ala Gly Asn Tyr Val Met Gly Leu Leu
610                 615                 620

Arg Phe Asp Lys Asn Val Val Asn Lys Lys Leu Ile Ile Asp Ile Gly
625                 630                 635                 640

Asp Gly Gly Lys Gly Ala Asn Ser Leu Ser Asn Ser Gly Gly Asp Thr
                645                 650                 655

Thr Val Lys Leu Cys Asp Asp Asp Lys Asn Cys Leu Val Lys Ile
                660                 665                 670

Ile Ala His Gly Gly Asp Glu Gly Asn Tyr Leu Gln Asp Ser Ser
        675                 680                 685

Glu Gly Ile Asp Asn Leu Val His Tyr Arg Phe Ala Pro Gly Leu Gln
        690                 695                 700

Asn Ser Gly Glu Asp Glu Ile Leu Val Pro Tyr Gln Asn Pro Asp Met
705                 710                 715                 720

Pro Tyr Gly Lys Leu His Lys Gly Asp Lys Glu Cys Ser Cys Asn Ser
                725                 730                 735

Asp Leu Leu Glu Lys Asn Ser Asn Lys Tyr Trp Gly Ala Gly Gly Cys
            740                 745                 750

Ser Ser Ile Tyr Asn Cys Ala Gln Glu Gly Ala Asp Gly Met Val Arg
        755                 760                 765

Ile Thr Cys Glu Lys Trp Ser Gly Asn Val Gly Lys Ile Ser Leu Ile
        770                 775                 780

Asp Glu Asn Ala Cys Ser Asp Leu Phe Val Thr Leu Ile Glu Lys Met
785                 790                 795                 800

His Lys Ser Thr Ser Gly Ile Pro Asp Val Val Lys Glu Phe Leu Gln
                805                 810                 815

Lys Ile Ser Lys Val Ser Phe Cys Arg Gln Ser Lys Ser Phe Pro Asn
                820                 825                 830

Leu Ile Ser Ser Met Ser Lys Tyr Phe Thr Ala Ile Asp Glu Ile Leu
                835                 840                 845

Ala Ser Gly Asp Ile Leu Gly His Asn Leu Ser Gly Leu Arg Lys Glu
                850                 855                 860

Leu Phe Thr Glu Leu Ser Asn Thr Glu Val Lys Ala Met Leu Ala Lys
865                 870                 875                 880

```
Leu Gly Ile Asn Glu Ser Pro Glu Thr Leu Leu Tyr Leu Asp Val
                885                 890                 895

Leu Asn Phe Asn Phe Gly Val Asn Ile Ser Asn Pro Pro Ser Gly Leu
            900                 905                 910

Leu Asn Tyr Tyr Ile Ser Asp Asn Glu Phe Asp Tyr Asp Leu Leu Lys
            915                 920                 925

Arg Asp Val Asp Tyr Asp Lys Leu Ser Asp Asn Glu Ala Met Met Phe
            930                 935                 940

Asn Val Thr Thr Glu Lys Pro Glu Gln Trp Leu Ser Val Glu Leu Lys
945                 950                 955                 960

Asp Gln Glu Phe Ala Arg Arg Tyr Gly Asn Phe Ile Asn Met Ile His
            965                 970                 975

Arg Ser Val Val Thr Asp Glu Glu Gly His Lys Lys Asn Asn Ile Val
            980                 985                 990

Val Ser Trp Met Tyr Thr Phe Phe Lys Ser Asp Lys Gln Leu Phe Glu
            995                 1000                1005

Leu Tyr Ala Ala Pro Phe Val Lys Leu Met Leu Gly Met Asp Leu
    1010                1015                1020

Asp Lys Phe Met Lys Trp Gly Ser Cys Ser Asp Thr His Ile Lys
    1025                1030                1035

Leu Phe Glu Ser Ile Asp Lys Tyr Ser Glu Lys Leu Pro Ser Arg
    1040                1045                1050

Met Gln Asp Phe Ile Lys Lys Ile Ala Thr Gly Asp Phe Cys Asn
    1055                1060                1065

Thr Phe Ser Lys Met Glu Leu Leu Asn Ser Tyr Gly Val Glu Leu
    1070                1075                1080

Ser Asn Tyr Ala Val Gly Cys Ala Leu Lys Asn Ala Asn Lys Ser
    1085                1090                1095

Cys Leu Glu Ser Lys Trp Arg Ser Ser Leu Gly Ser Met Ala Lys
    1100                1105                1110

Lys Leu Gln Asp Ala Val Asp Leu Asn Tyr Glu Val Phe Thr Asn
    1115                1120                1125

Ile Gly Ile Ala Ser Asn Arg Lys Glu Ile Ala Leu Leu Ile Asp
    1130                1135                1140

Ala Val Met Leu Asn Tyr Val Met Ser Asp Leu Asn Val Gly Asn
    1145                1150                1155

Ser Asp Ile Thr Ser Thr Leu Ser Leu Leu Asp Pro Ile Ser Ser
    1160                1165                1170

Gln Ala Leu Asp Asn Phe Pro Tyr Asp Thr Ile Val Glu Leu Arg
    1175                1180                1185

Gln Asp Ala Ser Asn Met Lys Tyr Gly Lys Tyr Gly Asp His Arg
    1190                1195                1200

Ala Asn Ile Val Thr Leu Trp Ser Tyr Met Ala Tyr Asn Ser Phe
    1205                1210                1215

Glu Trp Asn Val Glu Asp Phe Lys Ser Phe Val Lys Leu Leu Leu
    1220                1225                1230

Ala Glu Asp Leu Thr Ser Val Lys Ile Arg Lys Cys Ser Gly Ser
    1235                1240                1245

Leu Arg Tyr Leu Phe Asp Lys Leu Ser Gln Tyr Lys Asn Lys Leu
    1250                1255                1260

Pro Ala Val Leu Gln Asp Phe Leu Asp Lys Ile Ser Lys Glu Ser
    1265                1270                1275

Val Cys Arg Arg Met Ser Arg Phe Pro Ala Leu Glu Thr Leu Leu
```

-continued

```
                1280                1285                1290
Val Glu Tyr Ile Glu Glu Leu Leu Ser Lys Leu His Ala Gly Asn
    1295                1300                1305
Leu Phe Ser Phe Ser Ser Leu Tyr Asp Leu Asn Tyr Ala His Arg
    1310                1315                1320
Gly Lys Leu Pro Tyr Ser His Val Glu Arg Met Tyr Tyr His Ala
    1325                1330                1335
Ile Asn Val Trp Ser Asp Val Gly Lys Leu Ser Asn Ile Thr
    1340                1345                1350
Asn Leu Leu Asn Asp Pro Glu Val Tyr Lys Ile Phe Thr Asp Ala
    1355                1360                1365
Gly Ile Thr Ser Ser Gln Glu Glu Ile Ser Leu Ala Phe Asp Ala
    1370                1375                1380
Val Ile Phe Asn Leu Leu Leu Ser Glu Met Glu Ile Asp Gln Gln
    1385                1390                1395
Lys Met Arg Asn Leu Leu Leu Leu Ile Tyr Asp Asn Asn Leu Thr
    1400                1405                1410
Leu Ser Asp Ile Arg Leu Glu Arg Ser Lys Gly Ser Gly Gln Val
    1415                1420                1425
Gln Gln Val Met Val Asp Gln Asn Arg Phe Pro Gly Asn Ser Ile
    1430                1435                1440
Leu Met Leu Gln Gln Asn Ala Asn Asn Ile Lys Tyr Gly Asn Tyr
    1445                1450                1455
Gly Val His Arg Ala Asp Ile Ile Ala Leu Trp Ser Tyr Ile Ser
    1460                1465                1470
Tyr Ile Ser Ser Glu Ser Gly Trp Ser Ile Lys Lys Tyr Glu Ser
    1475                1480                1485
Phe Ile Lys Leu Leu Leu Gly Ile Asp Leu Lys Phe Ala Asp Leu
    1490                1495                1500
Lys Gly Cys Asp Asn Asp Ile Ile Asp Leu Phe Asn Arg Leu Asn
    1505                1510                1515
Ala Tyr Gly Asp Lys Leu Pro Leu Ser Leu Arg Asp Phe Leu Thr
    1520                1525                1530
Lys Ile Ser Glu Arg Asn Phe Cys Lys Glu Met Ser Leu Phe Pro
    1535                1540                1545
Glu Leu Glu Leu Ala Leu Met Ser Tyr Val Asn Gly Leu Ser Asp
    1550                1555                1560
Ile Leu Arg Val Gly Asp Val Phe Lys Val Asn Ser Val Ala Asn
    1565                1570                1575
Ile Val Asn Gly Arg Val Ser Asn Ile Asn Asp Val Tyr Ser Tyr
    1580                1585                1590
Leu Gly Asn Leu Leu Ser Asp Val Arg Glu Leu Ser Ser Asn Ile
    1595                1600                1605
Ala Asp Leu Leu Asn Asn Pro Asp Val Tyr Lys Ile Phe Thr Asp
    1610                1615                1620
Val Gly Ile Thr Ser Ser Lys Glu Asp Ile Leu Leu Ser Ile Asp
    1625                1630                1635
Ala Ile Ile Phe Asn Leu Leu Val Ser Glu Ile Lys Ile Asp Asn
    1640                1645                1650
Ser Gln Leu Glu Glu Leu Leu Leu Leu Val Gly Gly His Arg Asn
    1655                1660                1665
Ala Ser Ser Asn Asn Ala Asn Asn Ser Arg Ser Leu Pro Gln Gly
    1670                1675                1680
```

-continued

```
Ser Ala Asn Ser Asn Asn Phe Gln Gly Ile Arg Gln Arg Tyr Lys
1685               1690                1695

Val Thr Phe Lys Ile Ser Phe Ala Pro Asn Tyr Phe Pro Val Asp
    1700                1705                1710

Glu Ile Ile Lys Leu Gln Gln Asp Ala Asn Asn Met Glu Tyr Gly
    1715                1720                1725

Val His Gly Val His Arg Thr Asp Ile Ile Ala Leu Trp Ser Tyr
    1730                1735                1740

Ile Ser Tyr Ala Ser Ser Lys Ser Lys Trp Leu Phe Lys Arg Tyr
    1745                1750                1755

Gln Ser Phe Ala Gly Leu Leu Phe Glu Ile Gly Ala Trp Gly Lys
    1760                1765                1770

Cys Thr Ser Ala Glu Arg Val Phe Phe Thr Ser Met Asn Arg Tyr
    1775                1780                1785

Ser Glu Lys Leu Pro Leu Lys Val Tyr Asn Phe Ile Arg Lys Ile
    1790                1795                1800

Thr Thr Gly Asp Phe Ala Arg Lys Phe Ser Gly Met Gln Ser Leu
    1805                1810                1815

Tyr Thr Tyr Lys Gln Arg Val Tyr Asp Tyr Val Met His Cys Val
    1820                1825                1830

Leu Arg Gly Gly Leu Gly Gly Glu Cys Ser Asp Met Thr Leu Arg
    1835                1840                1845

Glu Ile Ser Asn Glu Leu His Lys Leu Lys Gln Glu Ile Tyr Ser
    1850                1855                1860

Asn Tyr Asp Val Phe Arg Asp Leu Gly Ile Thr Asn Gly Gln Gln
    1865                1870                1875

Glu Val Leu Leu Leu Ile Asn Val Met Met Leu Asn Tyr Ala Met
    1880                1885                1890

Ser Asp Leu Leu Val Ser Thr Thr Gln Val Asn Ser Met Leu Ala
    1895                1900                1905

Asp Val Arg Ser Ser Leu Ser Arg Thr Ala His Cys Leu Pro Tyr
    1910                1915                1920

Gly Thr Val Ser Gln Leu Gln Arg Ser Val Ser His Met Lys Tyr
    1925                1930                1935

Gly Glu Tyr Ser Asn Tyr Arg Ala Ser Val Val Ala Leu Trp Ala
    1940                1945                1950

Cys Ile Ser Cys Leu Ala Ser Phe Asn Asp Asp Met Glu Pro Leu
    1955                1960                1965

Ile Lys Leu Met Leu Glu Gly Asp
    1970                1975

<210> SEQ ID NO 11
<211> LENGTH: 643
<212> TYPE: DNA
<213> ORGANISM: Ehrlichia chaffeensis
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
```

```
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (195)..(197)
<223> OTHER INFORMATION: n is a, c, g, or t
<220> FEATURE:
<221> NAME/KEY: misc_feature
<222> LOCATION: (202)..(203)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
```

-continued

```
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (481)..(481)
```

```
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t

<400> SEQUENCE: 11
mggwtnntrk ykdkhknvvn trgyshkdwa vnthkcvtcn tdsdsavskd adcdagsgrt     60
khakvrdsgv gacdrnntnn addcysdvds nasnkdvyak vnvatymrgs hakrtnhsnh    120
dvaktshtta attrtvsana ahhvdkraan yntysstswt ygssvvtrty agyassrasd    180
saarhnvtnh trydnnnhtt gnntvvyarh shgvngasya ttmsttwtng kkrtkhkkyr    240
tdrrndnkat vrwgnvvdcv dskdarwtrt akmrgyartr kcyrnrsnrm nsasaaydva    300
gcsakgtras vvvvnrrdnt ynrrranmrt gssvtgdgns ryvstadvma tvnvdavsss    360
yadvhmdtvn tnrgsaasmr tdsrnrtsdt rrhatrhnst yrrgarcvhv gtmrdgsyrr    420
rhssstgraa yynhnrntrt gthhvasknn sdyanvshtr rssvdsvvvs dvddtraayy    480
nhrrnttsgv saratgmnsy grtsyrrcss ttcvvddrgh tdsdnratyy nhrrdttstt    540
gvyhvravnm nadyngtsyt rhsgttssng rsrrsgrsan dsrashrrrs gddsmmaddg    600
rntcsttsdt staagatatg gaddddntss thvssathhg asr                     643

<210> SEQ ID NO 12
<211> LENGTH: 37
<212> TYPE: DNA
<213> ORGANISM: Artificial Sequence
<220> FEATURE:
<223> OTHER INFORMATION: Synthetic Construct

<400> SEQUENCE: 12
```

```
aatccatgga attgttgtca ttagttggtg ggcatcg                              37

<210> SEQ ID NO 13
<211> LENGTH: 42
<212> TYPE: DNA
<213> ORGANISM: Artificial Sequence
<220> FEATURE:
<223> OTHER INFORMATION: Synthetic Construct

<400> SEQUENCE: 13
tcgacggatc caatcccctt ccagcattaa ttttatcaaa gg                        42
```

UNITED STATES PATENT AND TRADEMARK OFFICE
CERTIFICATE OF CORRECTION

PATENT NO. : 10,179,166 B2  
APPLICATION NO. : 15/362137  
DATED : January 15, 2019  
INVENTOR(S) : Yasuko Rikihisa and Dipu Mohan-Kumar Page 1 of 1

It is certified that error appears in the above-identified patent and that said Letters Patent is hereby corrected as shown below:

In the Specification

Column 1, Lines 19-22 replace the Government Support Clause with:
--This invention was made with government support under grant number AI047885 awarded by National Institutes of Health. The government has certain rights in the invention.--

Signed and Sealed this  
Sixth Day of October, 2020

Andrei Iancu  
*Director of the United States Patent and Trademark Office*